US012258416B1

(12) United States Patent
Laursen et al.

(10) Patent No.: US 12,258,416 B1
(45) Date of Patent: *Mar. 25, 2025

(54) BISPECIFIC CONSTRUCTS FOR TARGET AND COMPLEMENT ENGAGEMENT

(71) Applicant: Aarhus Universitet, Aarhus C (DK)

(72) Inventors: Nick Stub Laursen, Aarhus C (DK); Dennis Vestergaard Pedersen, Aarhus C (DK); Gregers Rom Andersen, Brabrand (DK); Steffen Thiel, Risskov (DK); Alessandra Zarantonello, Aarhus C (DK); Rasmus Kjeldsen Jensen, Aarhus C (DK); Henrik Pedersen, Aarhus C (DK)

(73) Assignee: Aarhus Universitet, Aarhus C (DK)

( * ) Notice: Subject to any disclaimer, the term of this patent is extended or adjusted under 35 U.S.C. 154(b) by 0 days.

This patent is subject to a terminal disclaimer.

(21) Appl. No.: 18/618,626

(22) Filed: Mar. 27, 2024

Related U.S. Application Data

(63) Continuation of application No. 17/251,023, filed as application No. PCT/EP2019/065206 on Jun. 11, 2019, now Pat. No. 12,110,321.

(30) Foreign Application Priority Data

Jun. 11, 2018 (EP) ..................... 18176954

(51) Int. Cl.
*A61K 39/395* (2006.01)
*A61K 9/00* (2006.01)
*C07K 16/28* (2006.01)
*A61K 39/00* (2006.01)

(52) U.S. Cl.
CPC ........ *C07K 16/2896* (2013.01); *A61K 9/0019* (2013.01); *C07K 16/2863* (2013.01); *A61K 2039/505* (2013.01); *C07K 2317/31* (2013.01); *C07K 2317/52* (2013.01); *C07K 2317/569* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 2005/0019326 A1* | 1/2005 | Stahl | G01N 33/564 530/388.25 |
| 2010/0291106 A1 | 11/2010 | Etemad-Gilbertson | |
| 2011/0081345 A1 | 4/2011 | Moore | |
| 2011/0104156 A1 | 5/2011 | Christadoss | |
| 2013/0209355 A1 | 8/2013 | De Weers | |
| 2015/0174268 A1* | 6/2015 | Li | A61K 31/4745 536/23.1 |
| 2017/0212130 A1 | 7/2017 | Rout | |

FOREIGN PATENT DOCUMENTS

| | | | |
|---|---|---|---|
| CA | 2862999 A1 | | 7/2013 |
| WO | WO/2006/008548 | * | 1/2006 |
| WO | 2006079372 A1 | | 8/2006 |
| WO | 2008154251 A2 | | 12/2008 |
| WO | 2010136311 A2 | | 12/2010 |
| WO | 2014028560 A2 | | 2/2014 |
| WO | 2015006504 A1 | | 1/2015 |

OTHER PUBLICATIONS

Van Audenhove, Isabel, and Jan Gettemans. "Nanobodies as versatile tools to understand, diagnose, visualize and treat cancer." EBioMedicine 8 (Apr. 2016): 40-48.

Afonine, Pavel V., et al.: "Towards automated crystallographic structure refinement with phenix. refine", Acta Crystallogr D Biol Crystallogr. Apr. 2012;68(Pt 4):352-67.

Brown, McKay, et al. "Tolerance of single, but not multiple, amino acid replacements in antibody VH CDR 2: a means of minimizing B cell wastage from somatic hypermutation?" Journal of immunology (Baltimore, Md.: 1950) 156.9 (1996): 3285-3291.

Cruz, Jonathan W. et al:; "A novel bispecific antibody platform to direct complement activity for efficient lysis of target cells"; Scientific Reports; Published Aug. 19, 2019.

Emsley et al.: "Features and development of Coot", Acta Crystallogr D Biol Crystallogr. Apr. 2010; 66(Pt 4):486-501.

Fryer, Jonathan P. et al; "Synthetic Peptides which inhibit the interaction between C1q and Immunoglubulin and progong Xenograft Survival"; Transplantation, vol. 70, 828-836, No. 5; Sep. 15, 2000.

Hee Young Hwang et al.; Highly specific inhibition of C1q globular-head binding to human IgG: A novel approach to control and regulate the classical complement pathway using an engineered single chain antibody variable fragment; Molecular Immunology; vol. 45, Issue 9, May 2008, pp. 2570-2580.

Hsiung et al; "A Monoclonal Antibody which can distinguish between the two Isotypes of Human C4"; Molecular Immunology, vol. 24, No. 1, pp. 91-96; 1987.

International Search Report issued Nov. 14, 2019 in PCT/EP2019/065206.

Jensen, Rasmus K. et el; "A Potent complement factor C3 specific nanobody inhibiting multiple functions in the alternative pathway of human and murine complement"; J. Biol. Chem. (2018) 293(17) 6269-6281.

Kabsch, W. "Integration, scaling, space-group assignment and post-refinement", Acta Crystallogr. D Biol. Crystallogr. 66, 133-144, 2010. ISSN 0907-4449, doi:10.1107/S0907444909047374.

(Continued)

*Primary Examiner* — Meera Natarajan
(74) *Attorney, Agent, or Firm* — Greenberg Traurig, LLP

(57) ABSTRACT

Single domain antibodies are provided, which are capable of specifically binding to an epitope of a human complement factor selected from the group consisting of C1q, C3, C4 and/or the proteolytic derivatives C3b and C4b. Further the use of the antibodies are provided for methods in modulating the activity of the complement system as well as methods of treating disorders associated with complement activation.

19 Claims, 25 Drawing Sheets

Specification includes a Sequence Listing.

(56) References Cited

OTHER PUBLICATIONS

Katschke; K. et al; "Structural and Functional Analysis of a C3b-specific Antibody That Selectively Inhibits the Alternative Pathway of Complement"; The Journal of Biological Chemistry, vol. 284, No. 16, 00 10473-10479, Apr. 17, 2009.

Kontermann et al.: "Complement recruitment using bispecific diabodies", Nature Biotechnology vol. 15, Jul. 1997, 629-31. doi: 10.1038/nbt0797-629.

Laursen, Nick S., et al. "Functional and structural characterization of a potent C1q inhibitor targeting the classical pathway of the complement system." Frontiers in immunology 11 (2020): 1504.

McCoy et al.: "Phaser crystallographic software", Journal of Applied Crystallography, Aug. 1, 2007;40(Pt4):658-674. Epub Jul. 13, 2007. doi: 10.1107/S0021889807021206.

Moreau et al.: "Structural and Functional Characterization of a Single-Chain Form of the Recognition Domain of Complement Protein C1q", Frontiers in Immunology Mar. 2, 2016; vol. 7, Article 79, doi: 10.3389/fimmu.2016.00079.

Pardon, Els et al; "A general protocol for the generation of Nanobodies for structural biology"; Nature Protocols; vol. 9 No. 3, Feb. 27, 2017.

Pilely, Katrine at al; A specific assay for quantification of human C4c by use of an anti-C4c monoclonal antibody; Journal of Immunological Methods; 405, 2014; 87-96.

Romäo, Ema et al; "Identification of useful Nanobodies by Phage Display of Immuni Single Domain Libraries Derived from Camelid Heavy Chain Antibodies"; Current Pharmaceutical Design; 2016; 22,6500-6518.

Rossotti et al.: "Increasing the potency of neutralizing single-domain antibodies by functionalization with a CD11b/CD18 binding domain", MAbs. Sep.-Oct. 2015; vol. 7 Issue 5: 820-828, doi: 10.1080/19420862.2015.1068491.

Scheres, S.H: "RELION: implementation of a Bayesian approach to cryo-EM structure determination", Journal of Structural Biology Dec. 2012;180(3):519-30, doi: 10.1016/j.jsb.2012.09.006.

Suloway, C. et al.: "Automated molecular microscopy: the new Leginon system", Journal of Structural Biology 151, (2005) 41-60.

Tenner, Andrea J., P. H. Lesavre, and N. R. Cooper. "Purification and radiolabeling of human C1q." Journal of immunology (Baltimore, Md.: 1950) 127.2 (1981): 648-653.

Vajdos, Felix F., et al. "Comprehensive functional maps of the antigen-binding site of an anti-ErbB2 antibody obtained with shotgun scanning mutagenesis." Journal of molecular biology 320.2 (2002): 415-428.

Voss, et al.: (2009) "DoG Picker and TiltPicker: software tools to facilitate particle selection in single particle electron microscopy", Journal of Structural Biology, 166, 205-213. doi: 10.1016/j.jsb.2009.01.004.

Zarantonello, Alessandra et al; Two potent C4 and C4b nanobodies inhibiting the classical pathway of the complement system; Molecular Immunology 102, 2018, pp. 129-235.

\* cited by examiner

Figure 2C
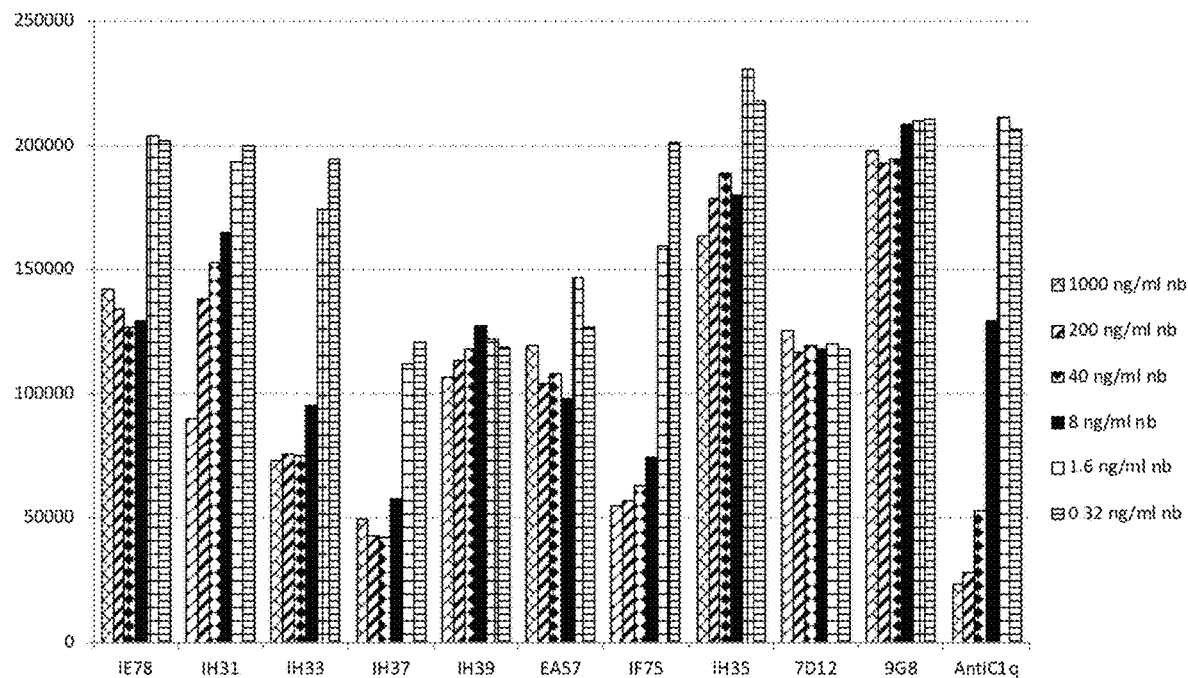
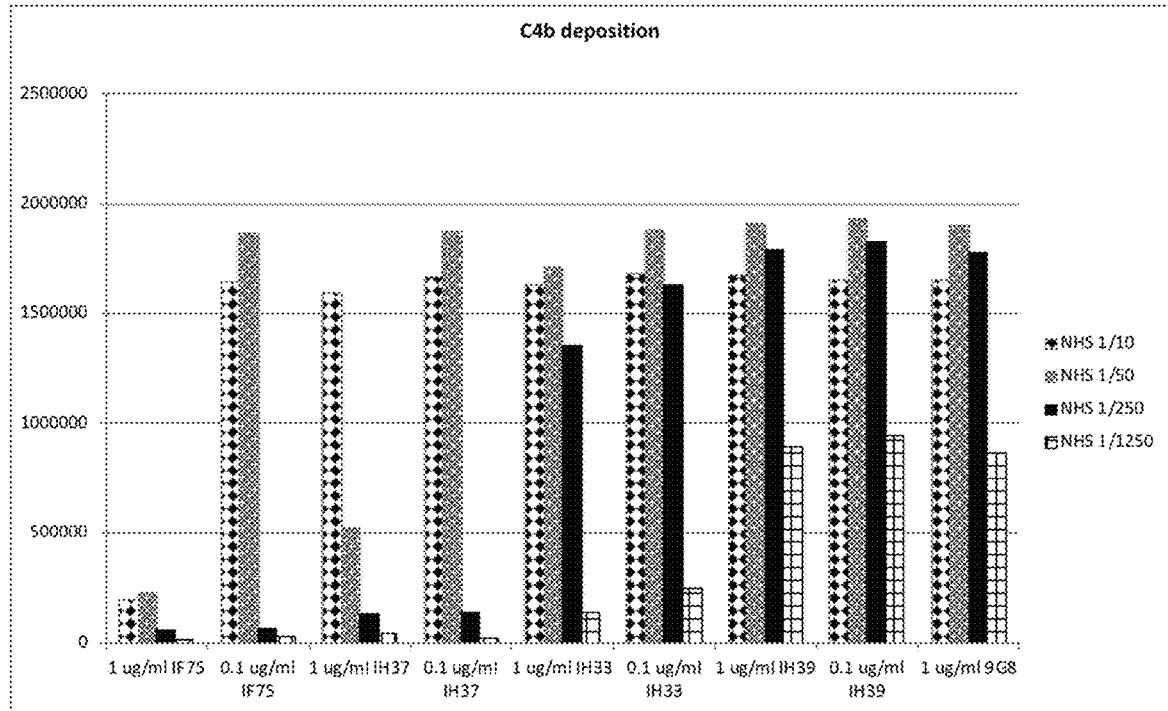
Figure 2D

Figure 4A
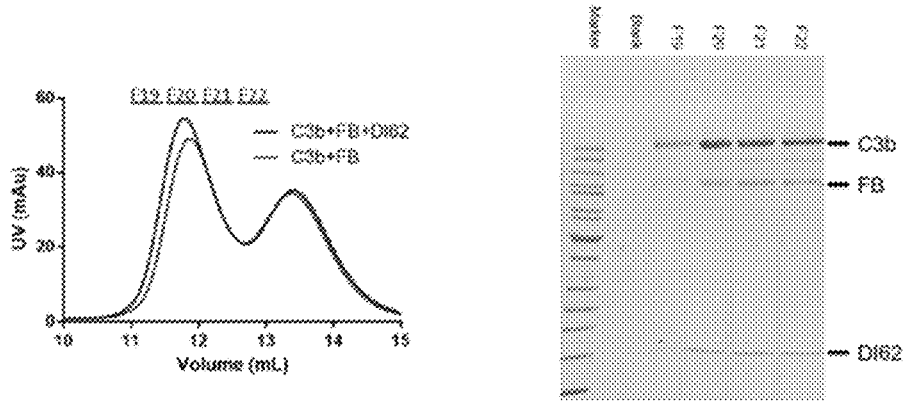
Figure 4B
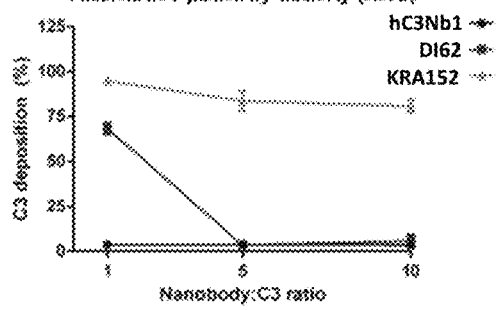
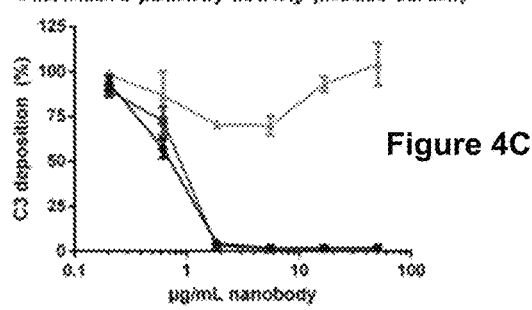
Figure 4C
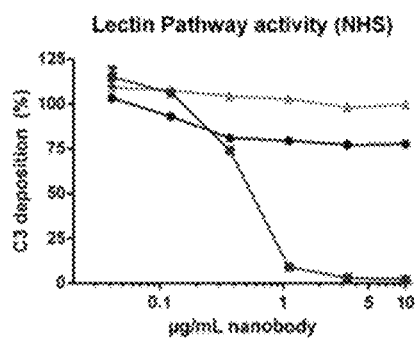
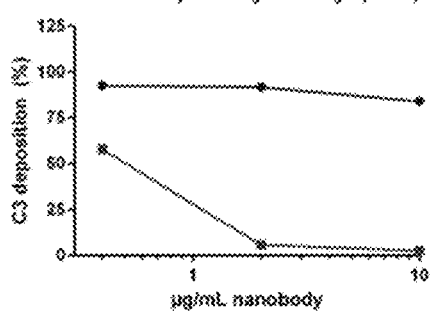
Figure 4D
Figure 4E

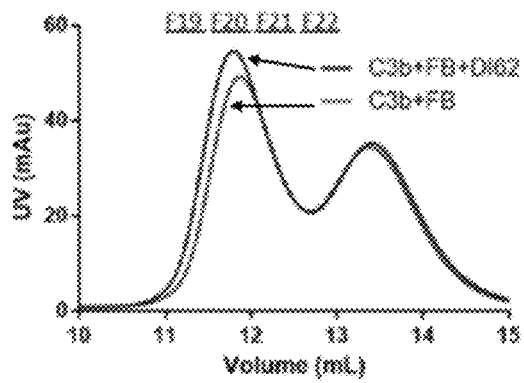
Figure 4F
Figure 5A
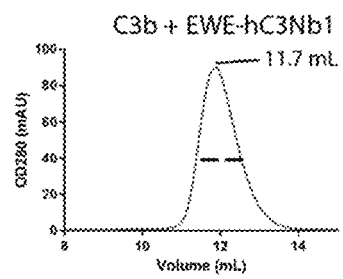
Figure 5B
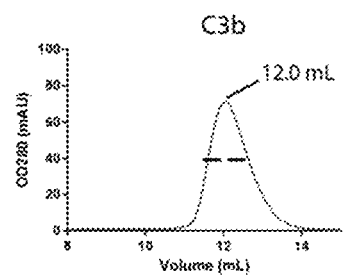
Figure 5C
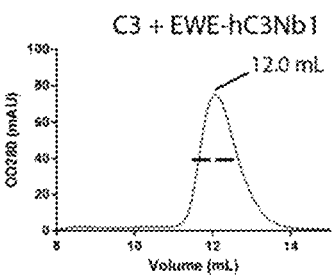
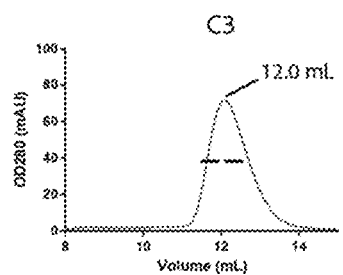
Figure 5D
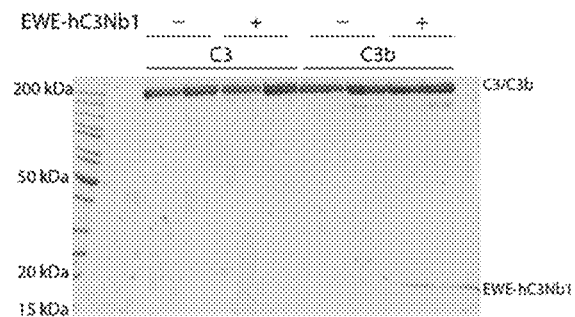
Figure 5E

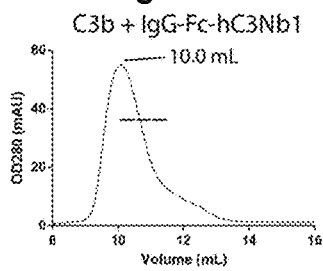
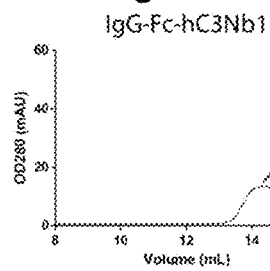
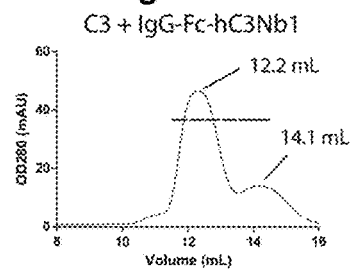
Figure 6A     Figure 6B     Figure 6C
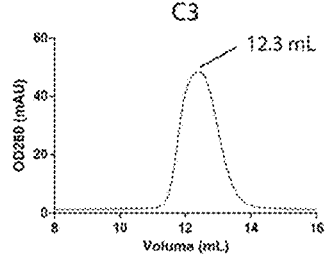
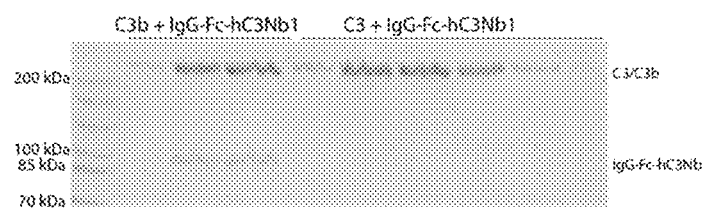
Figure 6D     Figure 6E
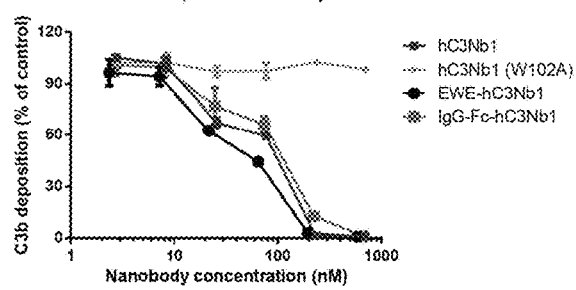
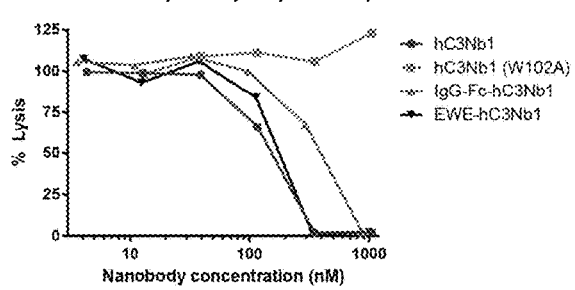
Figure 7A     Figure 7B

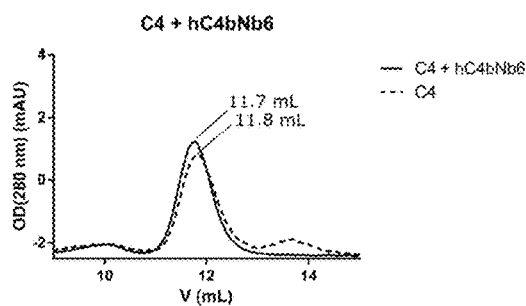
Figure 8A
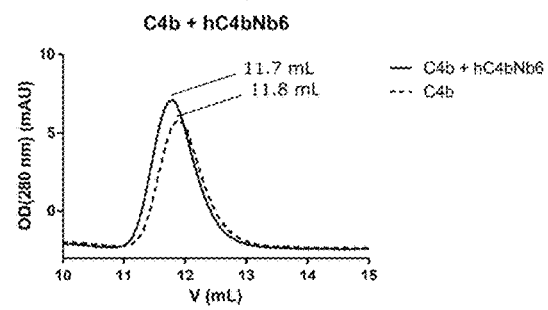
Figure 8B
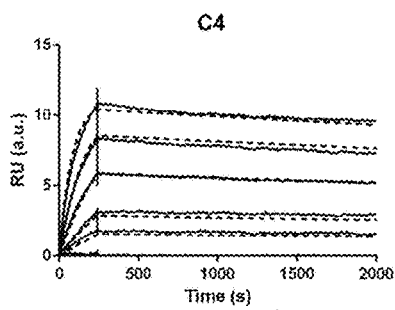
Figure 8C
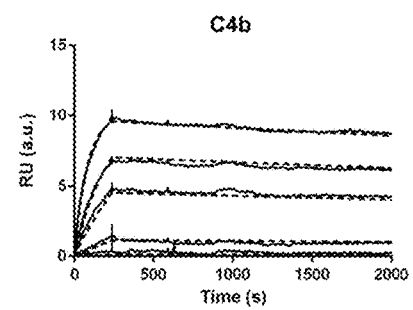
Figure 8D
| Analyte | $k_a$ (1/Ms) | $k_d$ (1/s) | $K_D$ (M) |
|---|---|---|---|
| C4 | $1.23 \cdot 10^6 \pm 0.03 \cdot 10^6$ | $5.7 \cdot 10^{-5} \pm 0.4 \cdot 10^{-5}$ | $4.6 \cdot 10^{-11} \pm 0.2 \cdot 10^{-11}$ |
| C4b | $5.3 \cdot 10^6 \pm 0.4 \cdot 10^6$ | $6.1 \cdot 10^{-5} \pm 0.6 \cdot 10^{-5}$ | $1.2 \cdot 10^{-11} \pm 0.2 \cdot 10^{-11}$ |
Figure 8E

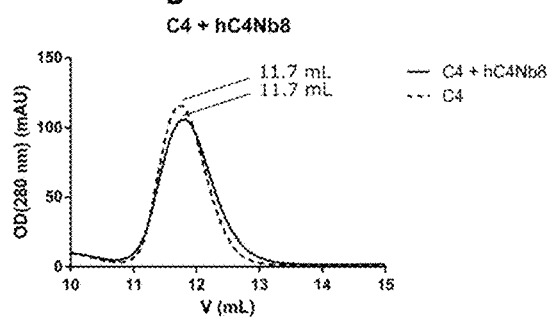
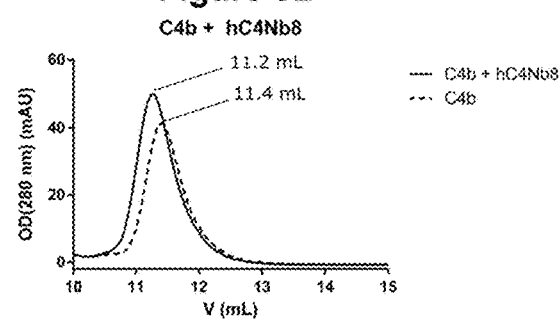
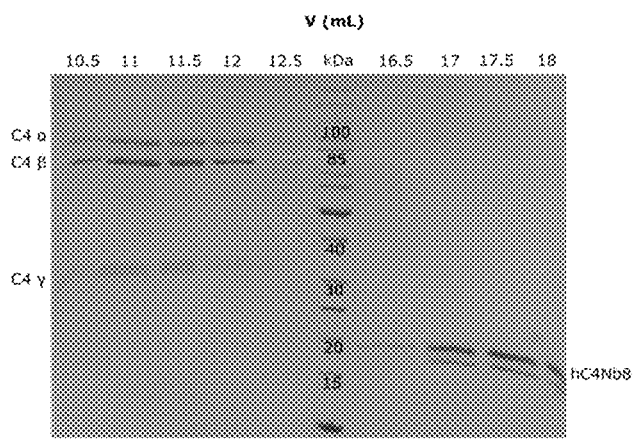
Figure 9C

Figure 12A
| Name | N-terminal | C-terminal |
|---|---|---|
| BiCE161 | IF75 | MU1053 |
| DF85 | IF75 | 7D12 |
| DH38 | IH31 | 7D12 |
| DF90 | IH35 | 7D12 |
| IA74 | EA57 | 7D12 |
| BiCE128 | DF85 | 9G8 |
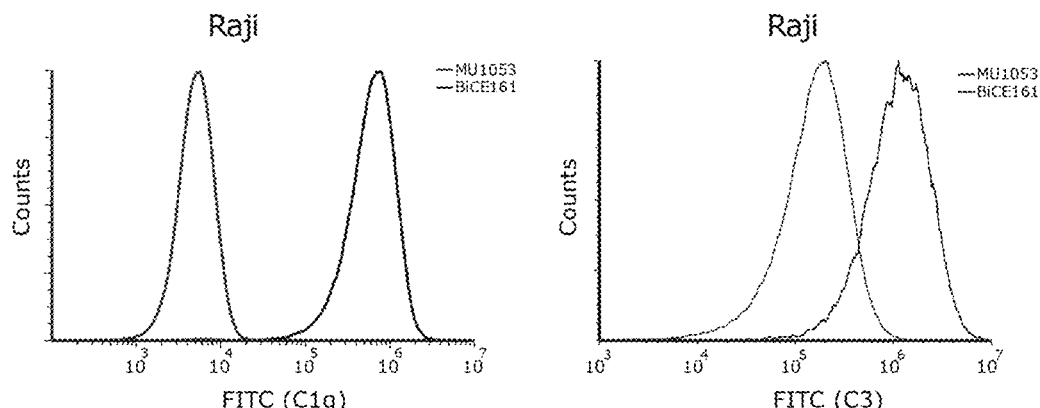
Figure 12B
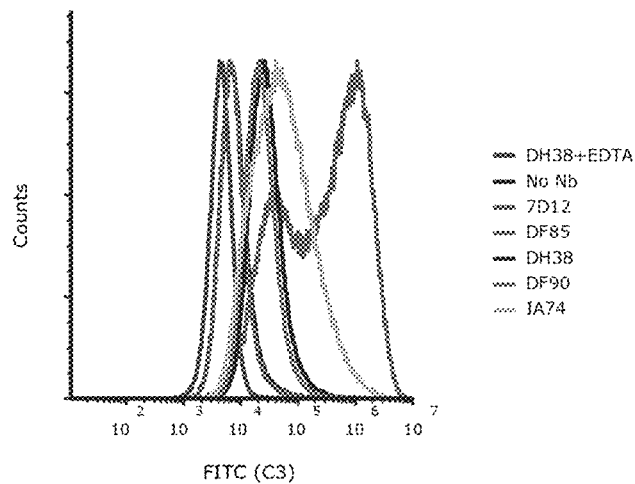
Figure 12C Figure 12D
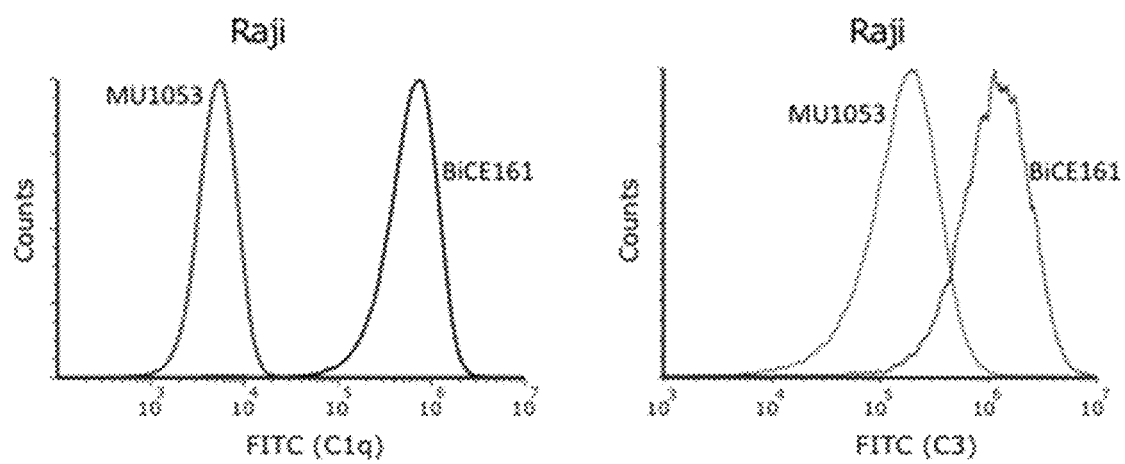
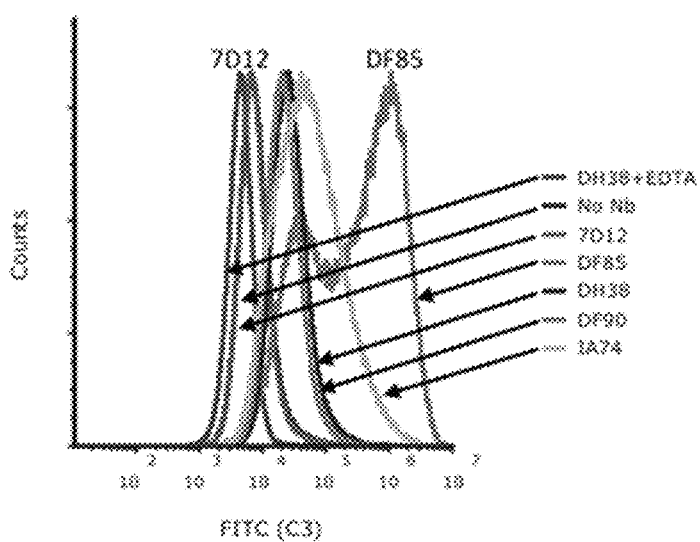
Figure 12E

Figure 13E
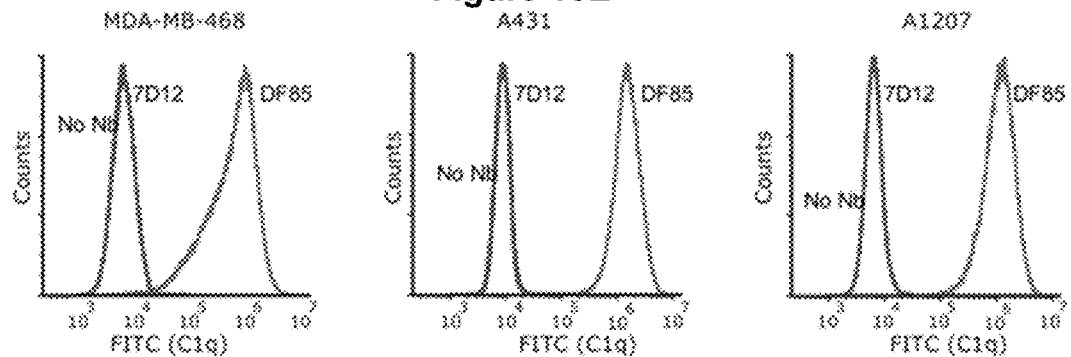
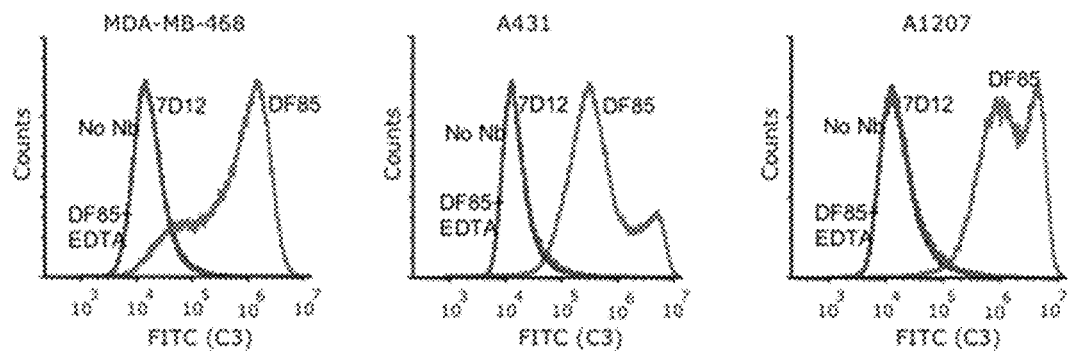
Figure 13F
Figure 13G
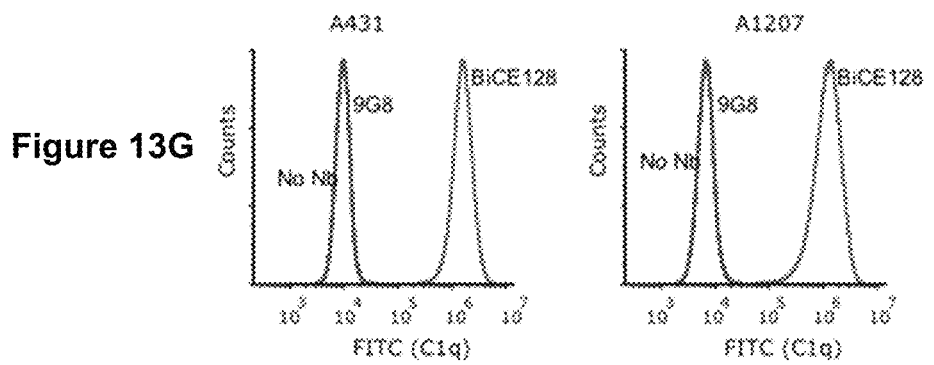
Figure 13H
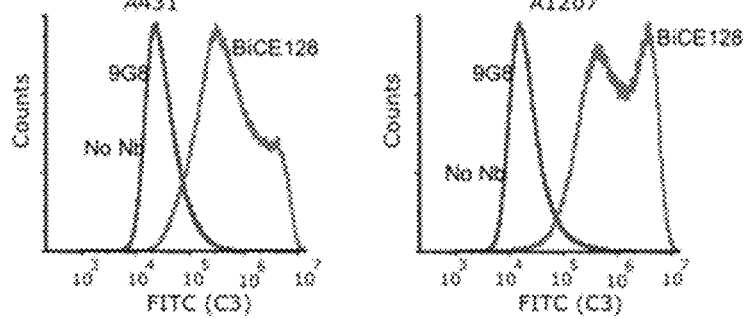

SEQUENCE LISTING

Sequence total quantity: 85
SEQ ID NO: 1             moltype = AA  length = 1641
FEATURE                  Location/Qualifiers
source                   1..1641
                         mol_type = protein
                         organism = Homo sapiens
SEQUENCE: 1
SPMYSIITPN ILRLESEETM VLEAHDAQGD VPVTVTVHDF PGKKLVLSSE KTVLTPATNH    60
MGNVTFTIPA NREFKSEKGR NKFVTVQATF GTQVVEKVVL VSLQSGYLFI QTDKTIYTPG   120
STVLYRIFTV NHKLLPVGRT VMVNIENPEG IPVKQDSLSS QNQLGVLPLS WDIPELVNMG   180
QWKIRAYYEN SPQQVFSTEF EVKEYVLPSF EVIVEPTEKF YYIYNEKGLE VTITARFLYG   240
KKVEGTAFVI FGIQDGEQRI SLPESLKRIP IEDGSGEVVL SRKVLLDGVQ NPRAEDLVGK   300
SLYVSATVIL HSGSDMVQAE RSGIPIVTSP YQIHFTKTPK YFKPGMPFDL MVFVTNPDGS   360
PAYRVPVAVQ GEDTVQSLTQ GDGVAKLSIN THPSQKPLSI TVRTKKQELS EAEQATRTMQ   420
ALPYSTVGNS NNYLHLSVLR TELRPGETLN VNFLLRMDRA HEAKIRYYTY LIMNKGRLLK   480
AGRQVREPGQ DLVVLPLSIT TDFIPSFRLV AYYTLIGASG QREVVADSVW VDVKDSCVGS   540
LVVKSGQSED RQPVPGQQMT LKIEGDHGAR VVLVAVDKGV FVLNKKNKLT QSKIWDVVEK   600
ADIGCTPGSG KDYAGVFSDA GLTFTSSSGQ QTAQRAELQC PQPAARRRRS VQLTEKRMDK   660
VGKYPKELRK CCEDGMRENP MRFSCQRRTR FISLGEACKK VFLDCCNYIT ELRRQHARAS   720
HLGLARSNLD EDIIAEENIV SRSEFPESWL WNVEDLKEPP KNGISTKLMN IFLKDSITTW   780
EILAVSMSDK KGICVADPFE VTVMQDFFID LRLPYSVVRN EQVEIRAVLY NYRQNQELKV   840
RVELLHNPAF CSLATTKRRH QQTVTIPPKS SLSVPYVIVP LKTGLQEVEV KAAVYHHFIS   900
DGVRKSLKVV PEGIRMNKTV AVRTLDPERL GREGVQKEDI PPADLSDQVP DTESETRILL   960
QGTPVAQMTE DAVDAERLKH LIVTPSGCGE QNMIGMTPTV IAVHYLDETE QWEKFGLEKR  1020
QGALELIKKG YTQQLAFRQP SSAFAAFVKR APSTWLTAYV VKVFSLAVNL IAIDSQVLCG  1080
AVKWLILEKQ KPDGVFQEDA PVIHQEMIGG LRNNNEKDMA LTAFVLISLQ EAKDICEEQV  1140
NSLPGSITKA GDFLEANYMN LQRSYTVAIA GYALAQMGRL KGPLLNKFLT TAKDKNRWED  1200
PGKQLYNVEA TSYALLALLQ LKDFDFVPPV VRWLNEQRYY GGGYGSTQAT FMVFQALAQY  1260
QKDAPDHQEL NLDVSLQLPS RSSKITHRIH WESASLLRSE ETKENEGFTV TAEGKGQGTL  1320
SVVTMYHAKA KDQLTCNKFD LKVTIKPAPE TEKRPQDAKN TMILEICTRY RGDQATMSI   1380
LDISMMTGFA PDTDDLKQLA NGVDRYISKY ELDKAFSDRN TLIIYLDKVS HSEDDCLAFK  1440
VHQYFNVELI QPGAVKVYAY YNLEESCTRF YHPEKEDGKL NKLCRDELCR CAEENCFIQK  1500
SDDKVTLEER LDKACEPGVD YVYKTRLVKV QLSNDFDEYI MAIEQTIKSG SDEVQVGQQR  1560
TFISPIKCRE ALKLEEKKHY LMWGLSSDFW GEKPNLSYII GKDTWVEHWP EEDECQDEEN  1620
QKQCQDLGAF TESMVVFGCP N                                           1641

SEQ ID NO: 2             moltype = AA  length = 1635
FEATURE                  Location/Qualifiers
source                   1..1635
                         mol_type = protein
                         organism = Mus musculus
SEQUENCE: 2
IPMYSIITPN VLRLESEETI VLEAHDAQGD IPVTVTVQDF LKRQVLTSEK TVLTGASGHL    60
RSVSIKIPAS KEFNSDKEGH KYVTVVANFG ETVVEKAVMV SFQSGYLFIQ TDKTIYTPGS   120
TVLYRIFTVD NNLLPVGKTV VILIETPDGI PVKRDILSSN NQHGILPLSW NIPELVNMGQ   180
WKIRAFYEHA PKQIFSAEFE VKEYVLPSFE VRVEPTETFY YIDDPNGLEV SIIAKFLYGK   240
NVDGTAFVIF GVQDGKKIS LAHSLTRVVI EDGVGDAVLT RKVLMEGVRP SNADALVGKS   300
LYVSVTVILH SGSDMVEAER SGIPIVTSPY QIHFTKTPKF FKPAMPFDLM VFVTNPDGSP   360
ASKVLVVTQG SNAKALTQDD GVAKLSINTP NSRQPLTITV RTKKDTLPES RQATKTMEAH   420

```
PYSTMHNSNN YLHLSVSRME LKPGDNLNVN FHLRTDPGHE AKIRYYTLYLV MNKGKLLKAG  480
RQVREPGQDL VVLSLPITPE FIPSFRLVAY YTLIGASGQR EVVADSVWVD VKDSCIGTLV  540
VKGDPRDNHL APGQQTTLRI EGNQGARVGL VAVDKGVFVL NKKNKLTQSK IWDVVEKADI  600
GCTPGSGKNY AGVFMDAGLA FKTSQGLQTE QRADLECTKP AASVQLMERR MDKAGQYTDK  660
GLRKCCEDGM RDIPMRYSCQ RRARLITQGE NCIKAFIFKI NHITKLREQH RRDHVLGLAR  720
SELEEDIIPE EDIISRSHFP QSWLWTIEEL KEPEKNGIST KVMNIFLKDS ITTWEILAVS  780
LSDKKGICVA DPYEIRVMQD FFIDLRLPYS VVRNEQVEIR AVLFNYREQE ELKVRVELLH  840
NPAFCSMATA KNRYFQTIKI PPKSSVAVPY VIVPLKIGQQ EVEVKAAVFN HFISDGVKKT  900
LKVVPEGMRI NKTVAIHTLD PEKLGQGGVQ KVDVPAADLS DQVPDTDSET RIILQGSPVV  960
QMAEDAVDGE RLKHLIVTPA GCGEQNMIGM TPTVIAVHYL DQTEQWEKFG IEKRQEALEL 1020
IKKGYTQQLA FKQPSSAYAA FNNRPPSTWL TAYVVKVFSL AANLIAIDSH VLCGAVKWLI 1080
LEKQKPDGVF QEDGPVIHQE MIGGFRNAKE ADVSLTAFVL IALQEARDIC EGQVNSLPGS 1140
INKAGEYIEA SYMNLQRPYT VAIAGYALAL MNKLEEPYLG KFLNTAKDRN RWEEPDQQLY 1200
NVEATSYALL ALLLLKDFDS VPPVVRWLNE QRYYGGGYGS TQATFMVFQA LAQYQTDVPD 1260
HKDLNMDVSF HLPSRSSATT FRLLWENGNL LRSEETKQNE AFSLTAKGKG RGTLSVVAVY 1320
HAKLKSKVTC KKFDLRVSIR PAPETAKKPE EAKNTMFLEI CTKYLGDVDA TMSILDISMM 1380
TGFAPDTKDL ELLASGVDRY ISKYEMNKAF SNKNTLIIYL EKISHTEEDC LTFKVHQYFN 1440
VGLIQPGSVK VYSYYNLEES CTRFYHPEKD DGMLSKLCHS EMCRCAEENC FMQQSQEKIN 1500
LNVRLDKACE PGVDYVYKTE LTNIELLDDF DEYTMTIQQV IKSGSDEVQA GQQRKFISHI 1560
KCRNALKLQK GKKYLMWGLS SDLWGEKPNT SYIIGKDTWV EHWPEAEECQ DQKYQKQCEE 1620
LGAFTESMVV YGCPN                                                 1635

SEQ ID NO: 3              moltype = AA   length = 223
FEATURE                   Location/Qualifiers
source                    1..223
                          mol_type = protein
                          organism = Homo sapiens
SEQUENCE: 3
EDLCRAPDGK KGEAGRPGRR GRPGLKGEQG EPGAPGIRTG IQGLKGDQGE PGPSGNPGKV   60
GYPGPSGPLG ARGIPGIKGT KGSPGNIKDQ PRPAFSAIRN NPPMGGNVVI FDTVITNGEN  120
PYQNHSGRFV CTVPGYYYFT FQVLSQWEIC LSIVSSSRGQ VRRSLGFCDT TNKGLFQVVS  180
GGMVLQLQQG DQVWVEKDPK KGHIYQGSEA DSVFSGFLIF PSA                   223

SEQ ID NO: 4              moltype = AA   length = 226
FEATURE                   Location/Qualifiers
source                    1..226
                          mol_type = protein
                          organism = Homo sapiens
SEQUENCE: 4
QLSCTGPPAI PGIPGIPGTP GPDGQPGTPG IKGEKGLPGL AGDHGEFGEK GDPGIPGNPG   60
KVGPKGPMGP KGGPGAPGAP GPKGESGDYK ATQKIAFSAT RTINVPLRRD QTIRFDHVIT  120
NMNNNYEPRS GKFTCKVPGL YYFTYHASSR GNLCVNLMRG RERAQKVVTF CDYAYNTFQV  180
TTGGMVLKLE QGENVFLQAT DKNSLLGMEG ANSIFSGFLL FPDMEA                226

SEQ ID NO: 5              moltype = AA   length = 217
FEATURE                   Location/Qualifiers
source                    1..217
                          mol_type = protein
                          organism = Homo sapiens
SEQUENCE: 5
NTGCYGIPGM PGLPGAPGKD GYDGLPGPKG EPGIPAIPGI RGPKGQKGEP GLPGHPGKNG   60
PMGPPGMPGV PGPMGIPGEP GEEGRYKQKF QSVFTVTRQT HQPPAPNSLI RFNAVLTNPQ  120
GDYDTSTGKF TCKVPGLYYF VYHASHTANL CVLLYRSGVK VVTFCGHTSK TNQVNSGGVL  180
LRLQVGEEVW LAVNDYYDMV GIQGSDSVFS GFLLFPD                          217

SEQ ID NO: 6              moltype = AA   length = 767
FEATURE                   Location/Qualifiers
source                    1..767
                          mol_type = protein
                          organism = Homo sapiens
SEQUENCE: 6
NVNFQKAINE KLGQYASPTA KRCCQDGVTR LPMMRSCEQR AARVQQPDCR EPFLSCCQFA   60
ESLRKKSRDK GQAGLQRALE ILQEEDLIDE DDIPVRSFFP ENWLWRVETV DRFQILTLWL  120
PDSLTTWEIH GLSLSKTKGL CVATPVQLRV FREFHLHLRL PMSVRRFEQL ELRPVLYNYL  180
DKNLTVSVHV SPVEGLCLAG GGGLAQQVLV PAGSARPVAF SVVPTAAAAV SLKVVARGSF  240
EFPVGDAVSK VLQIEKEGAI HREELVYELN PLDHRGRTLE IPGNSDPNMI PDGDFNSYVR  300
VTASDPLDTL GSEGALSPGG VASLLRLPRG CGEQTMIYLA PTLAASRYLD KTEQWSTLPP  360
ETKDHAVDLI QKGYMRIQQF RKADGSYAAW LSRDSSTWLT AFVLKVLSLA QEQVGGSPEK  420
LQETSNWLLS QQQADGSFQD PCPVLDRSMQ GGLVGNDETV ALTAFVTIAL HHGLAVFQDE  480
GAEPLKQRVE ASISKANSFL GEKASAGLLG AHAAAITAYA LTLTKAPVDL LGVAHNNLMA  540
MAQETGDNLY WGSVTGSQSN AVSPTPAPRN PSDPMPQAPA LWIETTAYAL LHLLLHEGKA  600
EMADQASAWL TRQGSFQGGF RSTQDTVIAL DALSAYWIAS HTTEERGLNV TLSSTGRNGF  660
KSHALQLNNR QIRGLEEELQ FSLGSKINVK VGGNSKGTLK VLRTYNVLDM KNTTCQDLQI  720
EVTVKGHVEY TMEANEDYED YEYDELPAKD DPDAPLQPVT PLQLFEG               767

SEQ ID NO: 7              moltype = AA   length = 656
FEATURE                   Location/Qualifiers
source                    1..656
                          mol_type = protein
```

```
                        organism = Homo sapiens
SEQUENCE: 7
KPRLLLFSPS VVHLGVPLSV GVQLQDVPRG QVVKGSVFLR NPSRNNVPCS PKVDFTLSSE    60
RDFALLSLQV PLKDAKSCGL HQLLRGPEVQ LVAHSPWLKD SLSRTTNIQG INLLFSSRRG   120
HLFLQTDQPI YNPGQRVRYR VFALDQKMRP STDTITVMVE NSHGLRVRKK EVYMPSSIFQ   180
DDFVIPDISE PGTWKISARF SDGLESNSST QFEVKKYVLP NFEVKITPGK PYILTVPGHL   240
DEMQLDIQAR YIYGKPVQGV AYVRFGLLDE DGKKTFFRGL ESQTKLVNGQ SHISLSKAEF   300
QDALEKLNMG ITDLQGLRLY VAAAIIESPG GEMEEAELTS WYFVSSPFSL DLSKTKRHLV   360
PGAPFLLQAL VREMSGSPAS GIPVKVSATV SSPGSVPEVQ DIQQNTDGSG QVSIPIIIPQ   420
TISELQLSVS AGSPHPAIAR LTVAAPPSGG PGFLSIERPD SRPPRVGDTL NLNLRAVGSG   480
ATFSHYYYMI LSRGQIVFMN REPKRTLTSV SVFVDHHLAP SFYFVAFYYH GDHPVANSLR   540
VDVQAGACEG KLELSVDGAK QYRNGESVKL HLETDSLALV ALGALDTALY AAGSKSHKPL   600
NMGKVFEAMN SYDLGCGPGG GDSALQVFQA AGLAFSDGDQ WTLSRKRLSC PKEKTT       656

SEQ ID NO: 8             moltype = AA  length = 291
FEATURE                  Location/Qualifiers
source                   1..291
                         mol_type = protein
                         organism = Homo sapiens
SEQUENCE: 8
EAPKVVEEQE SRVHYTVCIW RNGKVGLSGM AIADVTLLSG FHALRADLEK LTSLSDRYVS    60
HFETEGPHVL LYFDSVPTSR ECVGFEAVQE VPVGLVQPAS ATLYDYYNPE RRCSVFYGAP   120
SKSRLLATLC SAEVCQCAEG KCPRQRRALE RGLQDEDGYR MKFACYYPRV EYGFQVKVLR   180
EDSRAAFRLF ETKITQVLHF TKDVKAAANQ MRNFLVRASC RLRLEPGKEY LIMGLDGATY   240
DLEGHPQYLL DSNSWIEEMP SERLCRSTRQ RAACAQLNDF LQEYGTQGCQ V            291

SEQ ID NO: 9             moltype = AA  length = 129
FEATURE                  Location/Qualifiers
source                   1..129
                         mol_type = protein
                         organism = Homo sapiens
SEQUENCE: 9
QVQLVESGGG LVQPGGSLRL SCAASGFTLN QYAIGWFRQA PGKEREGVSC ISNSDGGLYY    60
ADSVKGRFTI SRDNAKNTVY LQMNSLKPED TAVYYCATDP GGPTMYGSRW CDSRLFYSWG   120
QGTQVTVSS                                                           129

SEQ ID NO: 10            moltype = AA  length = 10
FEATURE                  Location/Qualifiers
REGION                   1..10
                         note = Artificial sequence/unknown
REGION                   1..10
                         note = MISC_FEATURE - CDR1
source                   1..10
                         mol_type = protein
                         organism = unidentified
SEQUENCE: 10
GFTLNQYAIG                                                           10

SEQ ID NO: 11            moltype = AA  length = 10
FEATURE                  Location/Qualifiers
REGION                   1..10
                         note = Artificial sequence/unknown
REGION                   1..10
                         note = MISC_FEATURE - CDR2
source                   1..10
                         mol_type = protein
                         organism = unidentified
SEQUENCE: 11
CISNSDGGLY                                                           10

SEQ ID NO: 12            moltype = AA  length = 20
FEATURE                  Location/Qualifiers
REGION                   1..20
                         note = Artificial sequence/unknown
REGION                   1..20
                         note = MISC_FEATURE - CDR3
source                   1..20
                         mol_type = protein
                         organism = unidentified
SEQUENCE: 12
DPGGPTMYGS RWCDSRLFYS                                                20

SEQ ID NO: 13            moltype = AA  length = 125
FEATURE                  Location/Qualifiers
REGION                   1..125
                         note = Artificial sequence/unknown
REGION                   1..125
                         note = MISC_FEATURE - IF75
source                   1..125
```

-continued

```
                              mol_type = protein
                              organism = unidentified
SEQUENCE: 13
QVQLVETGGG LVQAGGSLRL SCAASGRTFN NDVMAWFRQA PGTEREFVAL ITAGGGTHYA    60
DSVKGRFVIS RDNDKNMAYL QMNSLKSEDT AIYYCGADEN PPGWPSRWSS AYDYWGQGTQ   120
VTVSS                                                               125

SEQ ID NO: 14              moltype = AA  length = 10
FEATURE                    Location/Qualifiers
REGION                     1..10
                           note = Artificial sequence/unknown
REGION                     1..10
                           note = MISC_FEATURE - CDR1
source                     1..10
                           mol_type = protein
                           organism = unidentified
SEQUENCE: 14
GRTFNNDVMA                                                           10

SEQ ID NO: 15              moltype = AA  length = 9
FEATURE                    Location/Qualifiers
REGION                     1..9
                           note = Artificial sequence/unknown
REGION                     1..9
                           note = MISC_FEATURE - CDR2
source                     1..9
                           mol_type = protein
                           organism = unidentified
SEQUENCE: 15
LITAGGGTH                                                             9

SEQ ID NO: 16              moltype = AA  length = 17
FEATURE                    Location/Qualifiers
REGION                     1..17
                           note = Artificial sequence/unknown
REGION                     1..17
                           note = MISC_FEATURE - CDR3
source                     1..17
                           mol_type = protein
                           organism = unidentified
SEQUENCE: 16
DENPPGWPSR WSSAYDY                                                   17

SEQ ID NO: 17              moltype = AA  length = 128
FEATURE                    Location/Qualifiers
REGION                     1..128
                           note = Artificial sequence/unknown
REGION                     1..128
                           note = MISC_FEATURE - IF78
source                     1..128
                           mol_type = protein
                           organism = unidentified
SEQUENCE: 17
QVQLVESGGG LVQDGDSLRL SCAGSGWTFR DSMYNMGWFR QAPGKEREFV AAISWRGGST    60
LYADSVKGRF TISRDNAKNT VYLQMNSLKP EDTAVYQCAA DTSARAALYS TGYEYDHWGQ   120
GTQVTVSS                                                            128

SEQ ID NO: 18              moltype = AA  length = 12
FEATURE                    Location/Qualifiers
REGION                     1..12
                           note = Artificial sequence/unknown
REGION                     1..12
                           note = MISC_FEATURE - CDR1
source                     1..12
                           mol_type = protein
                           organism = unidentified
SEQUENCE: 18
GWTFRDSMYN MG                                                        12

SEQ ID NO: 19              moltype = AA  length = 11
FEATURE                    Location/Qualifiers
REGION                     1..11
                           note = Artificial sequence/unknown
REGION                     1..11
                           note = MISC_FEATURE - CDR2
source                     1..11
                           mol_type = protein
                           organism = unidentified
SEQUENCE: 19
```

```
AISWRGGSTL Y                                                                    11

SEQ ID NO: 20           moltype = AA   length = 17
FEATURE                 Location/Qualifiers
REGION                  1..17
                        note = Artificial sequence/unknown
REGION                  1..17
                        note = MISC_FEATURE - CDR3
source                  1..17
                        mol_type = protein
                        organism = unidentified
SEQUENCE: 20
DTSARAALYS TGYEYDH                                                              17

SEQ ID NO: 21           moltype = AA   length = 127
FEATURE                 Location/Qualifiers
REGION                  1..127
                        note = Artificial sequence/unknown
REGION                  1..127
                        note = MISC_FEATURE - IH31
source                  1..127
                        mol_type = protein
                        organism = unidentified
SEQUENCE: 21
QVQLVESGGG LVQAGGSLRL SCAASGRTSS DHITAWFRQA PGKEREFVAS INWSGSRAYY               60
ADSDKRRFTI SRDNAKNTVS LQTNSLKPED TAVYYCAVKF ADISDAYYHH QTDYDYWGQG              120
TQVTVSS                                                                        127

SEQ ID NO: 22           moltype = AA   length = 10
FEATURE                 Location/Qualifiers
REGION                  1..10
                        note = Artificial sequence/unknown
REGION                  1..10
                        note = MISC_FEATURE - CDR1
source                  1..10
                        mol_type = protein
                        organism = unidentified
SEQUENCE: 22
GRTSSDHITA                                                                      10

SEQ ID NO: 23           moltype = AA   length = 10
FEATURE                 Location/Qualifiers
REGION                  1..10
                        note = Artificial sequence/unknown
REGION                  1..10
                        note = MISC_FEATURE - CDR2
source                  1..10
                        mol_type = protein
                        organism = unidentified
SEQUENCE: 23
SINWSGSRAY                                                                      10

SEQ ID NO: 24           moltype = AA   length = 18
FEATURE                 Location/Qualifiers
REGION                  1..18
                        note = Artificial sequence/unknown
REGION                  1..18
                        note = MISC_FEATURE - CDR3
source                  1..18
                        mol_type = protein
                        organism = unidentified
SEQUENCE: 24
KFADISDAYY HHQTDYDY                                                             18

SEQ ID NO: 25           moltype = AA   length = 119
FEATURE                 Location/Qualifiers
REGION                  1..119
                        note = Artificial sequence/unknown
REGION                  1..119
                        note = MISC_FEATURE - IH33
source                  1..119
                        mol_type = protein
                        organism = unidentified
SEQUENCE: 25
QVQLVETGGG LVQTGGSLRL SCAASGSTDS IAAIIWYRQT PENEREFVAG ITSGVNTNYA               60
APVKGRFTIS RDNAKNTVYL QMNSLKPEDT GVYYCKAAVV MGPSTTDYWG QGTQVTVSS               119

SEQ ID NO: 26           moltype = AA   length = 10
FEATURE                 Location/Qualifiers
```

```
REGION                  1..10
                        note = Artificial sequence/unknown
REGION                  1..10
                        note = MISC_FEATURE - CDR1
source                  1..10
                        mol_type = protein
                        organism = unidentified
SEQUENCE: 26
GSTDSIAAII                                                                      10

SEQ ID NO: 27           moltype = AA  length = 7
FEATURE                 Location/Qualifiers
REGION                  1..7
                        note = Artificial sequence/unknown
REGION                  1..7
                        note = MISC_FEATURE - CDR2
source                  1..7
                        mol_type = protein
                        organism = unidentified
SEQUENCE: 27
GITSGVN                                                                          7

SEQ ID NO: 28           moltype = AA  length = 11
FEATURE                 Location/Qualifiers
REGION                  1..11
                        note = Artificial sequence/unknown
REGION                  1..11
                        note = MISC_FEATURE - CDR3
source                  1..11
                        mol_type = protein
                        organism = unidentified
SEQUENCE: 28
AVVMGPSTTD Y                                                                    11

SEQ ID NO: 29           moltype = AA  length = 124
FEATURE                 Location/Qualifiers
REGION                  1..124
                        note = Artificial sequence/unknown
REGION                  1..124
                        note = MISC_FEATURE - IH35
source                  1..124
                        mol_type = protein
                        organism = unidentified
SEQUENCE: 29
QVQLVETGGG VAQAGGSLRL SCAASGFSFD DYAIGWLRQA PGKEREGVSC ISAGDGSPQY               60
ADSVKGRFTI SSDNAKNTVY LQMNSLKPED TAVYYCAVSR WSNCAWDYYG MDPWGKGTLV              120
TVSS                                                                           124

SEQ ID NO: 30           moltype = AA  length = 10
FEATURE                 Location/Qualifiers
REGION                  1..10
                        note = Artificial sequence/unknown
REGION                  1..10
                        note = MISC_FEATURE - CDR1
source                  1..10
                        mol_type = protein
                        organism = unidentified
SEQUENCE: 30
GFSFDDYAIG                                                                      10

SEQ ID NO: 31           moltype = AA  length = 10
FEATURE                 Location/Qualifiers
REGION                  1..10
                        note = Artificial sequence/unknown
REGION                  1..10
                        note = MISC_FEATURE - CDR2
source                  1..10
                        mol_type = protein
                        organism = unidentified
SEQUENCE: 31
CISAGDGSPQ                                                                      10

SEQ ID NO: 32           moltype = AA  length = 15
FEATURE                 Location/Qualifiers
REGION                  1..15
                        note = Artificial sequence/unknown
REGION                  1..15
                        note = MISC_FEATURE - CDR3
source                  1..15
```

```
                              mol_type = protein
                              organism = unidentified
SEQUENCE: 32
SRWSNCAWDY YGMDP                                                    15

SEQ ID NO: 33           moltype = AA  length = 125
FEATURE                 Location/Qualifiers
REGION                  1..125
                        note = Artificial sequence/unknown
REGION                  1..125
                        note = MISC_FEATURE - IH37
source                  1..125
                        mol_type = protein
                        organism = unidentified
SEQUENCE: 33
QVQLVESGGG LAQAGGSLRL SCQGSGRTFN NDVLAWFRQA PGKEREYVAM ITSGGNPFYA    60
DSVKGRFVIS RDNDKNTVYL QMNSLKSEDT AIYYCAADEN PPGWPSRWSS AYDYWGQGTQ   120
VTVSS                                                              125

SEQ ID NO: 34           moltype = AA  length = 10
FEATURE                 Location/Qualifiers
REGION                  1..10
                        note = Artificial sequence/unknown
REGION                  1..10
                        note = MISC_FEATURE - CDR1
source                  1..10
                        mol_type = protein
                        organism = unidentified
SEQUENCE: 34
GRTFNNDVLA                                                          10

SEQ ID NO: 35           moltype = AA  length = 9
FEATURE                 Location/Qualifiers
REGION                  1..9
                        note = Artificial sequence/unknown
REGION                  1..9
                        note = MISC_FEATURE - CDR2
source                  1..9
                        mol_type = protein
                        organism = unidentified
SEQUENCE: 35
MITSGGNPF                                                            9

SEQ ID NO: 36           moltype = AA  length = 17
FEATURE                 Location/Qualifiers
REGION                  1..17
                        note = Artificial sequence/unknown
REGION                  1..17
                        note = MISC_FEATURE - CDR3
source                  1..17
                        mol_type = protein
                        organism = unidentified
SEQUENCE: 36
DENPPGWPSR WSSAYDY                                                  17

SEQ ID NO: 37           moltype = AA  length = 124
FEATURE                 Location/Qualifiers
REGION                  1..124
                        note = Artificial sequence/unknown
REGION                  1..124
                        note = MISC_FEATURE - IH39
source                  1..124
                        mol_type = protein
                        organism = unidentified
SEQUENCE: 37
QVQLVESGGG LVQAGGSLRL SCVAYGVASV TTVMGWFRQS PGKEREFVAA IGPSGGTHYG    60
DSAKGRFTIS RDNAKNTVYL QMNSLKPEDT AVYDCAADLR GGGMWASSGR YEYWGQGTQV   120
TVSS                                                               124

SEQ ID NO: 38           moltype = AA  length = 10
FEATURE                 Location/Qualifiers
REGION                  1..10
                        note = Artificial sequence/unknown
REGION                  1..10
                        note = MISC_FEATURE - CDR1
source                  1..10
                        mol_type = protein
                        organism = unidentified
SEQUENCE: 38
```

```
GVASVTTVMG                                                                              10

SEQ ID NO: 39          moltype = AA   length = 9
FEATURE                Location/Qualifiers
REGION                 1..9
                       note = Artificial sequence/unknown
REGION                 1..9
                       note = MISC_FEATURE - CDR2
source                 1..9
                       mol_type = protein
                       organism = unidentified
SEQUENCE: 39
AIGPSGGTH                                                                               9

SEQ ID NO: 40          moltype = AA   length = 16
FEATURE                Location/Qualifiers
REGION                 1..16
                       note = Artificial sequence/unknown
REGION                 1..16
                       note = MISC_FEATURE - CDR3
source                 1..16
                       mol_type = protein
                       organism = unidentified
SEQUENCE: 40
DLRGGGMWAS SGRYEY                                                                       16

SEQ ID NO: 41          moltype = AA   length = 124
FEATURE                Location/Qualifiers
REGION                 1..124
                       note = Artificial sequence/unknown
REGION                 1..124
                       note = MISC_FEATURE - hC4bNb6
source                 1..124
                       mol_type = protein
                       organism = unidentified
SEQUENCE: 41
QVQLVETGGG VVRAGGSLRL SCAASGRTLG RYSMAWFRQA PGKERQFVAA INWSGGSTYY                        60
PDFAKDRFTI SRDSAKNMVY LQMNSLKPED TAVYYCAAGG MDIEITRANE YDYWGQGTQV                        120
TVSS                                                                                    124

SEQ ID NO: 42          moltype = AA   length = 10
FEATURE                Location/Qualifiers
REGION                 1..10
                       note = Artificial sequence/unknown
REGION                 1..10
                       note = MISC_FEATURE - CDR1
source                 1..10
                       mol_type = protein
                       organism = unidentified
SEQUENCE: 42
GRTLGRYSMA                                                                              10

SEQ ID NO: 43          moltype = AA   length = 10
FEATURE                Location/Qualifiers
REGION                 1..10
                       note = Artificial sequence/unknown
REGION                 1..10
                       note = MISC_FEATURE - CDR2
source                 1..10
                       mol_type = protein
                       organism = unidentified
SEQUENCE: 43
AINWSGGSTY                                                                              10

SEQ ID NO: 44          moltype = AA   length = 15
FEATURE                Location/Qualifiers
REGION                 1..15
                       note = Artificial sequence/unknown
REGION                 1..15
                       note = MISC_FEATURE - CDR3
source                 1..15
                       mol_type = protein
                       organism = unidentified
SEQUENCE: 44
GGMDIEITRA NEYDY                                                                        15

SEQ ID NO: 45          moltype = AA   length = 124
FEATURE                Location/Qualifiers
REGION                 1..124
```

```
                                 note = Artificial sequence/unknown
REGION                           1..124
                                 note = MISC_FEATURE - hC4Nb8
source                           1..124
                                 mol_type = protein
                                 organism = unidentified
SEQUENCE: 45
QVQLVESGGG LVQTGDSLRL SCAASGRTFS RYAMGWFRQA PGKERELVAA INWSGGSTYY    60
ADFAKGRFTI SRDNAKNMLY LRMSSLKPED TAVYYCAAGG PEVEITRANE YDYWGQGTQV   120
TVSS                                                                124

SEQ ID NO: 46            moltype = AA  length = 10
FEATURE                  Location/Qualifiers
REGION                   1..10
                         note = Artificial sequence/unknown
REGION                   1..10
                         note = MISC_FEATURE - CDR1
source                   1..10
                         mol_type = protein
                         organism = unidentified
SEQUENCE: 46
GRTFSRYAMG                                                           10

SEQ ID NO: 47            moltype = AA  length = 10
FEATURE                  Location/Qualifiers
REGION                   1..10
                         note = Artificial sequence/unknown
REGION                   1..10
                         note = MISC_FEATURE - CDR2
source                   1..10
                         mol_type = protein
                         organism = unidentified
SEQUENCE: 47
AINWSGGSTY                                                           10

SEQ ID NO: 48            moltype = AA  length = 15
FEATURE                  Location/Qualifiers
REGION                   1..15
                         note = Artificial sequence/unknown
REGION                   1..15
                         note = MISC_FEATURE - CDR3
source                   1..15
                         mol_type = protein
                         organism = unidentified
SEQUENCE: 48
GGPEVEITRA NEYDY                                                     15

SEQ ID NO: 49            moltype = AA  length = 118
FEATURE                  Location/Qualifiers
REGION                   1..118
                         note = Artificial sequence/unknown
REGION                   1..118
                         note = MISC_FEATURE - D121
source                   1..118
                         mol_type = protein
                         organism = unidentified
SEQUENCE: 49
QVQLVESGGG LVQAGGSLRL SCVVSGSTFS DYAMGWYRQA AGEQRELVAA IYSTGRTNYI    60
DSVKGRFTIS RDNAKTTVYL QMNSLKPEDT AVYYCNLLGA TTMINTKWGQ GTQVTVSS     118

SEQ ID NO: 50            moltype = AA  length = 11
FEATURE                  Location/Qualifiers
REGION                   1..11
                         note = Artificial sequence/unknown
REGION                   1..11
                         note = MISC_FEATURE - CDR1
source                   1..11
                         mol_type = protein
                         organism = unidentified
SEQUENCE: 50
SGSTFSDYAM G                                                         11

SEQ ID NO: 51            moltype = AA  length = 9
FEATURE                  Location/Qualifiers
REGION                   1..9
                         note = Artificial sequence/unknown
REGION                   1..9
                         note = MISC_FEATURE - CDR2
source                   1..9
```

-continued

```
                        mol_type = protein
                        organism = unidentified
SEQUENCE: 51
AIYSTGRTN                                                                    9

SEQ ID NO: 52           moltype = AA   length = 10
FEATURE                 Location/Qualifiers
REGION                  1..10
                        note = Artificial sequence/unknown
REGION                  1..10
                        note = MISC_FEATURE - CDR3
source                  1..10
                        mol_type = protein
                        organism = unidentified
SEQUENCE: 52
LGATTMINTK                                                                  10

SEQ ID NO: 53           moltype = AA   length = 128
FEATURE                 Location/Qualifiers
REGION                  1..128
                        note = Artificial sequence/unknown
REGION                  1..128
                        note = MISC_FEATURE - DI62
source                  1..128
                        mol_type = protein
                        organism = unidentified
SEQUENCE: 53
QVQLVESGGG LVQAGGSLRL SCAASGRTFS DYTMGWFRQA PGKEREFVAG LSTGGSFTRY           60
AASVEGRFTI SRDNAKTTVY LQMNNLQPED TAVYYCAADF TPYGTNWSRF REARDHYWGQ          120
GTQVTVSS                                                                   128

SEQ ID NO: 54           moltype = AA   length = 11
FEATURE                 Location/Qualifiers
REGION                  1..11
                        note = Artificial sequence/unknown
REGION                  1..11
                        note = MISC_FEATURE - CDR1
source                  1..11
                        mol_type = protein
                        organism = unidentified
SEQUENCE: 54
SGRTFSDYTM G                                                                11

SEQ ID NO: 55           moltype = AA   length = 10
FEATURE                 Location/Qualifiers
REGION                  1..10
                        note = Artificial sequence/unknown
REGION                  1..10
                        note = MISC_FEATURE - CDR2
source                  1..10
                        mol_type = protein
                        organism = unidentified
SEQUENCE: 55
GLSTGGSFTR                                                                  10

SEQ ID NO: 56           moltype = AA   length = 19
FEATURE                 Location/Qualifiers
REGION                  1..19
                        note = Artificial sequence/unknown
REGION                  1..19
                        note = MISC_FEATURE - CDR3
source                  1..19
                        mol_type = protein
                        organism = unidentified
SEQUENCE: 56
DFTPYGTNWS RFREARDHY                                                        19

SEQ ID NO: 57           moltype = AA   length = 127
FEATURE                 Location/Qualifiers
REGION                  1..127
                        note = Artificial sequence/unknown
REGION                  1..127
                        note = MISC_FEATURE - EWE-hC3Nb1
source                  1..127
                        mol_type = protein
                        organism = unidentified
SEQUENCE: 57
MEWEQVQLVE TGGGLVQAGG SLRLSCAASG SIFSINAMGW FRQAPGKERE FVATINRSGG           60
RTYYADSVKG RFTISRDNGK NMVYLQMHSL KPEDTAIYYC AAGTGWSPQT DNEYNYWGQG          120
```

```
TQVTVSS                                                                   127

SEQ ID NO: 58           moltype = AA  length = 11
FEATURE                 Location/Qualifiers
REGION                  1..11
                        note = Artificial sequence/unknown
REGION                  1..11
                        note = MISC_FEATURE - CDR1
source                  1..11
                        mol_type = protein
                        organism = unidentified
SEQUENCE: 58
SGSIFSINAM G                                                              11

SEQ ID NO: 59           moltype = AA  length = 10
FEATURE                 Location/Qualifiers
REGION                  1..10
                        note = Artificial sequence/unknown
REGION                  1..10
                        note = MISC_FEATURE - CDR2
source                  1..10
                        mol_type = protein
                        organism = unidentified
SEQUENCE: 59
TINRSGGRTY                                                                10

SEQ ID NO: 60           moltype = AA  length = 14
FEATURE                 Location/Qualifiers
REGION                  1..14
                        note = Artificial sequence/unknown
REGION                  1..14
                        note = MISC_FEATURE - CDR3
source                  1..14
                        mol_type = protein
                        organism = unidentified
SEQUENCE: 60
GTGWSPQTDN EYNY                                                           14

SEQ ID NO: 61           moltype = AA  length = 358
FEATURE                 Location/Qualifiers
REGION                  1..358
                        note = Artificial sequence/unknown
REGION                  1..358
                        note = MISC_FEATURE - IgG-Fc-hC3Nb1
source                  1..358
                        mol_type = protein
                        organism = unidentified
SEQUENCE: 61
APLEPKSSDK THTCPPCPAP ELLGGPSVFL FPPKPKDTLM ISRTPEVTCV VVDVSHEDPE          60
VKFNWYVDGV EVHNAKTKPR EEQYNSTYRV VSVLTVLHQD WLNGKEYKCK VSNKALPAPI         120
EKTISKAKGQ PREPQVYTLP PSREEMTKNQ VSLTCLVKGF YPSDIAVEWE SNGQPENNYK         180
TTPPVLDSDG SFFLYSKLTV DKSRWQQGNV FSCSVMHEAL HNHYTQKSLS LSPGAQVQLV         240
ETGGGLVQAG GSLRLSCAAS GSIFSINAMG WFRQAPGKER EFVATINRSG GRTYADSVK         300
GRFTISRDNG KNMVYLQMHS LKPEDTAIYY CAAGTGWSPQ TDNEYNYWGQ GTQVTVSS          358

SEQ ID NO: 62           moltype = AA  length = 11
FEATURE                 Location/Qualifiers
REGION                  1..11
                        note = Artificial sequence/unknown
REGION                  1..11
                        note = MISC_FEATURE - CDR1
source                  1..11
                        mol_type = protein
                        organism = unidentified
SEQUENCE: 62
SGSIFSINAM G                                                              11

SEQ ID NO: 63           moltype = AA  length = 10
FEATURE                 Location/Qualifiers
REGION                  1..10
                        note = Artificial sequence/unknown
REGION                  1..10
                        note = MISC_FEATURE - CDR2
source                  1..10
                        mol_type = protein
                        organism = unidentified
SEQUENCE: 63
TINRSGGRTY                                                                10
```

```
SEQ ID NO: 64            moltype = AA  length = 14
FEATURE                  Location/Qualifiers
REGION                   1..14
                         note = Artificial sequence/unknown
REGION                   1..14
                         note = MISC_FEATURE - CDR3
source                   1..14
                         mol_type = protein
                         organism = unidentified
SEQUENCE: 64
GTGWSPQTDN EYNY                                                        14

SEQ ID NO: 65            moltype = AA  length = 10
FEATURE                  Location/Qualifiers
REGION                   1..10
                         note = Artificial sequence/unknown
REGION                   1..10
                         note = MISC_FEATURE - polypeptide linker
source                   1..10
                         mol_type = protein
                         organism = synthetic construct
SEQUENCE: 65
GGGGSGGGGS                                                             10

SEQ ID NO: 66            moltype = AA  length = 129
FEATURE                  Location/Qualifiers
REGION                   1..129
                         note = Artificial sequence/unknown
REGION                   1..129
                         note = MISC_FEATURE - hC4Nb5
source                   1..129
                         mol_type = protein
                         organism = unidentified
SEQUENCE: 66
QVQLVETGGG LVQPGGSLRL SCAASGRTFN KNPMAWFRQP PGQERDLVAA ISWSGDSTNY       60
ANSVQGRFTI SRNNAQRTVS LSMNNLKPED TAVYYCAAVG RTDYSPNSLA LTAQNYDYWG      120
QGTQVTVSS                                                             129

SEQ ID NO: 67            moltype = AA  length = 10
FEATURE                  Location/Qualifiers
REGION                   1..10
                         note = Artificial sequence/unknown
REGION                   1..10
                         note = MISC_FEATURE - CDR1
source                   1..10
                         mol_type = protein
                         organism = unidentified
SEQUENCE: 67
GRTFNKNPMA                                                             10

SEQ ID NO: 68            moltype = AA  length = 10
FEATURE                  Location/Qualifiers
REGION                   1..10
                         note = Artificial sequence/unknown
REGION                   1..10
                         note = MISC_FEATURE - CDR2
source                   1..10
                         mol_type = protein
                         organism = unidentified
SEQUENCE: 68
AISWSGDSTN                                                             10

SEQ ID NO: 69            moltype = AA  length = 19
FEATURE                  Location/Qualifiers
REGION                   1..19
                         note = Artificial sequence/unknown
REGION                   1..19
                         note = MISC_FEATURE - CDR3
source                   1..19
                         mol_type = protein
                         organism = unidentified
SEQUENCE: 69
VGRTDYSPNS LALTAQNYD                                                   19

SEQ ID NO: 70            moltype = AA  length = 124
FEATURE                  Location/Qualifiers
REGION                   1..124
                         note = Artificial sequence/unknown
REGION                   1..124
```

```
                        note = MISC_FEATURE - hC4Nb4
source                  1..124
                        mol_type = protein
                        organism = unidentified
SEQUENCE: 70
QVQLVETGGG LVEAGGSLRI SCAASGRYAM GWFRQAPGNE RDFVAAISRS GDSANYADTA    60
WGRFTISRDN AQNTMTLQMN SLKPEDTAVY YCAAKAGLYS LNSLFLRSQE YTYWGQGTQV   120
TVSS                                                                124

SEQ ID NO: 71           moltype = AA   length = 6
FEATURE                 Location/Qualifiers
REGION                  1..6
                        note = Artificial sequence/unknown
REGION                  1..6
                        note = MISC_FEATURE - CDR1
source                  1..6
                        mol_type = protein
                        organism = unidentified
SEQUENCE: 71
GRYAMG                                                               6

SEQ ID NO: 72           moltype = AA   length = 10
FEATURE                 Location/Qualifiers
REGION                  1..10
                        note = Artificial sequence/unknown
REGION                  1..10
                        note = MISC_FEATURE - CDR2
source                  1..10
                        mol_type = protein
                        organism = unidentified
SEQUENCE: 72
AISRSGDSAN                                                          10

SEQ ID NO: 73           moltype = AA   length = 19
FEATURE                 Location/Qualifiers
REGION                  1..19
                        note = Artificial sequence/unknown
REGION                  1..19
                        note = MISC_FEATURE - CDR3
source                  1..19
                        mol_type = protein
                        organism = unidentified
SEQUENCE: 73
KAGLYSLNSL FLRSQEYTY                                                19

SEQ ID NO: 74           moltype = AA   length = 148
FEATURE                 Location/Qualifiers
source                  1..148
                        mol_type = protein
                        organism = Mus musculus
SEQUENCE: 74
ENCFMQQSQE KINLNVRLDK ACEPGVDYVY KTELTNIELL DDFDEYTMTI QQVIKSGSDE    60
VQAGQQRKFI SHIKCRNALK LQKGKKYLMW GLSSDLWGEK PNTSYIIGKD TWVEHWPEAE   120
ECQDQKYQKQ CEELGAFTES MVVYGCPN                                     148

SEQ ID NO: 75           moltype = AA   length = 45
FEATURE                 Location/Qualifiers
source                  1..45
                        mol_type = protein
                        organism = Mus musculus
SEQUENCE: 75
EKINLNVRLD KACPEAEECQ DQKYQKQCEE LGAFTESMVV YGCPN                   45

SEQ ID NO: 76           moltype = AA   length = 126
FEATURE                 Location/Qualifiers
REGION                  1..126
                        note = Artificial sequence/unknown
REGION                  1..126
                        note = MISC_FEATURE - pNSL270
source                  1..126
                        mol_type = protein
                        organism = unidentified
SEQUENCE: 76
QVQLVESGGG LVQAGGSLRL SCVASASTLD IYTYAMAWFR QAPGKRREFV AAISRNGYST    60
YYADSVKGRF TISKLNAKNT LYLQMNSLEP EDTAAYYCAA DRTTEVVDRE DDYGYWGQGT   120
QVTVSS                                                              126

SEQ ID NO: 77           moltype = AA   length = 12
FEATURE                 Location/Qualifiers
```

```
REGION                    1..12
                          note = Artificial sequence/unknown
REGION                    1..12
                          note = MISC_FEATURE - CDR1
source                    1..12
                          mol_type = protein
                          organism = unidentified
SEQUENCE: 77
ASTLDIYTYA MA                                                              12

SEQ ID NO: 78             moltype = AA   length = 10
FEATURE                   Location/Qualifiers
REGION                    1..10
                          note = Artificial sequence/unknown
REGION                    1..10
                          note = MISC_FEATURE - CDR2
source                    1..10
                          mol_type = protein
                          organism = unidentified
SEQUENCE: 78
AISRNGYSTY                                                                 10

SEQ ID NO: 79             moltype = AA   length = 15
FEATURE                   Location/Qualifiers
REGION                    1..15
                          note = Artificial sequence/unknown
REGION                    1..15
                          note = MISC_FEATURE - CDR3
source                    1..15
                          mol_type = protein
                          organism = unidentified
SEQUENCE: 79
DRTTEVVDRE DDYGY                                                           15

SEQ ID NO: 80             moltype = AA   length = 767
FEATURE                   Location/Qualifiers
source                    1..767
                          mol_type = protein
                          organism = Homo sapiens
SEQUENCE: 80
NVNFQKAINE KLGQYASPTA KRCCQDGVTR LPMMRSCEQR AARVQQPDCR EPFLSCCQFA           60
ESLRKKSRDK GQAGLQRALE ILQEEDLIDE DDIPVRSFFP ENWLWRVETV DRFQILTLWL          120
PDSLTTWEIH GLSLSKTKGL CVATPVQLRV FREFHLHLRL PMSVRRFEQL ELRPVLYNYL          180
DKNLTVSVHV SPVEGLCLAG GGGLAQQVLV PAGSARPVAF SVVPTAATAV SLKVVARGSF          240
EFPVGDAVSK VLQIEKEGAI HREELVYELN PLDHRGRTLE IPGNSDPNMI PDGDFNSYVR          300
VTASDPLDTL GSEGALSPGG VASLLRLPRG CGEQTMIYLA PTLAASRYLD KTEQWSTLPP          360
ETKDHAVDLI QKGYMRIQQF RKADGSYAAW LSRGSSTWLT AFVLKVLSLA QEQVGGSPEK          420
LQETSNWLLS QQQADGSFQD LSPVIHRSMQ GGLVGNDETV ALTAFVTIAL HHGLAVFQDE          480
GAEPLKQRVE ASISKASSFL GEKASAGLLG AHAAAITAYA LTLTKAPADL RGVAHNNLMA          540
MAQETGDNLY WGSVTGSQSN AVSPTPAPRN PSDPMPQAPA LWIETTAYAL LHLLLHEGKA          600
EMADQAAAWL TRQGSFQGGF RSTQDTVIAL DALSAYWIAS HTTEERGLNV TLSSTGRNGF          660
KSHALQLNNR QIRGLEEELQ FSLGSKINVK VGGNSKGTLK VLRTYNVLDM KNTTCQDLQI          720
EVTVKGHVEY TMEANEDYED YEYDELPAKD DPDAPLQPVT PLQLFEG                       767

SEQ ID NO: 81             moltype = AA   length = 690
FEATURE                   Location/Qualifiers
source                    1..690
                          mol_type = protein
                          organism = Homo sapiens
SEQUENCE: 81
ALEILQEEDL IDEDDIPVRS FFPENWLWRV ETVDRFQILT LWLPDSLTTW EIHGLSLSKT           60
KGLCVATPVQ LRVFREFHLH LRLPMSVRRF EQLELRPVLY NYLDKNLTVS VHVSPVEGLC          120
LAGGGGLAQQ VLVPAGSARP VAFSVVPTAA AAVSLKVVAR GSFEFPVGDA VSKVLQIEKE          180
GAIHREELVY ELNPLDHRGR TLEIPGNSDP NMIPDGDFNS YVRVTASDPL DTLGSEGALS          240
PGGVASLLRL PRGCGEQTMI YLAPTLAASR YLDKTEQWST LPPETKDHAV DLIQKGYMRI          300
QQFRKADGSY AAWLSRDSST WLTAFVLKVL SLAQEQVGGS PEKLQETSNW LLSQQQADGS          360
FQDPCPVLDR SMQGGLVGND ETVALTAFVT IALHHGLAVF QDEGAEPLKQ RVEASISKAN          420
SFLGEKASAG LLGAHAAAIT AYALTLTKAP VDLLGVAHNN LMAMAQETGD NLYWGSVTGS          480
QSNAVSPTPA PRNPSDPMPQ APALWIETTA YALLHLLLHE GKAEMADQAS AWLTRQGSFQ          540
GGFRSTQDTV IALDALSAYW IASHTTEERG LNVTLSSTGR NGFKSHALQL NNRQIRGLEE          600
ELQFSLGSKI NVKVGGNSKG TLKVLRTYNV LDMKNTTCQD LQIEVTVKGH VEYTMEANED          660
YEDYEYDELP AKDDPDAPLQ PVTPLQLFEG                                          690

SEQ ID NO: 82             moltype = AA   length = 690
FEATURE                   Location/Qualifiers
source                    1..690
                          mol_type = protein
                          organism = Homo sapiens
SEQUENCE: 82
```

```
ALEILQEEDL IDEDDIPVRS FFPENWLWRV ETVDRFQILT LWLPDSLTTW EIHGLSLSKT  60
KGLCVATPVQ LRVFREFHLH LRLPMSVRRF EQLELRPVLY NYLDKNLTVS VHVSPVEGLC 120
LAGGGGLAQQ VLVPAGSARP VAFSVVPTAA TAVSLKVVAR GSFEFPVGDA VSKVLQIEKE 180
GAIHREELVY ELNPLDHRGR TLEIPGNSDP NMIPDGDFNS YVRVTASDPL DTLGSEGALS 240
PGGVASLLRL PRGCGEQTMI YLAPTLAASR YLDKTEQWST LPPETKDHAV DLIQKGYMRI 300
QQFRKADGSY AAWLSRGSST WLTAFVLKVL SLAQEQVGGS PEKLQETSNW LLSQQQADGS 360
FQDLSPVIHR SMQGGLVGND ETVALTAFVT IALHHGLAVF QDEGAEPLKQ RVEASISKAS 420
SFLGEKASAG LLGAHAAAIT AYALTLTKAP ADLRGVAHNN LMAMAQETGD NLYWGSVTGS 480
QSNAVSPTPA PRNPSDPMPQ APALWIETTA YALLHLLLHE GKAEMADQAA AWLTRQGSFQ 540
GGFRSTQDTV IALDALSAYW IASHTTEERG LNVTLSSTGR NGFKSHALQL NNRQIRGLEE 600
ELQFSLGSKI NVKVGGNSKG TLKVLRTYNV LDMKNTTCQD LQIEVTVKGH VEYTMEANED 660
YEDYEYDELP AKDDPDAPLQ PVTPLQLFEG                                 690

SEQ ID NO: 83          moltype = AA  length = 654
FEATURE                Location/Qualifiers
source                 1..654
                       mol_type = protein
                       organism = Mus musculus
SEQUENCE: 83
KPRLLLFSPS VVNLGTPLSV GVQLLDAPPG QEVKGSVFLR NPKGGSCSPK KDFKLSSGDD  60
FVLLSLEVPL EDVRSCGLFD LRRAPHIQLV AQSPWLRNTA FKATETQGVN LLFSSRRGHI 120
FVQTDQPIYN PGQRVRYRVF ALDQKMRPST DFLTITVENS HGLRVLKKEI FTSTSIFQDA 180
FTIPDISEPG TWKISARFSD GLESNRSTHF EVKKYVLPNF EVKITPWKPY ILMVPSNSDE 240
IQLDIQARYI YGKPVQGVAY TRFALMDEQG KRTFLRGLET QAKLVEGRTH ISISKDQFQA 300
ALDKINIGVR DLEGLRLYAA TAVIESPGGE MEEAELTSWR FVSSAFSLDL SRTKRHLVPG 360
AHFLLQALVQ EMSGSEASNV PVKVSATLVS GSDSQVLDIQ QSTNGIGQVS ISFPIPPTVT 420
ELRLLVSAGS LYPAIARLTV QAPPSRGTGF LSIEPLDPRS PSVGDTFILN LQPVGIPAPT 480
FSHYYYMIIS RGQIMAMGRE PRKTVTSVSV LVDHQLAPSF YFVAYFYHQG HPVANSLLIN 540
IQSRDCEGKL QLKVDGAKEY RNADMMKLRI QTDSKALVAL GAVDMALYAV GGRSHKPLDM 600
SKVFEVINSY NVGCGPGGGD DALQVFQDAG LAFSDGDRLT QTREDLSCPK EKKS       654

SEQ ID NO: 84          moltype = AA  length = 766
FEATURE                Location/Qualifiers
source                 1..766
                       mol_type = protein
                       organism = Mus musculus
SEQUENCE: 84
NVNFQKAVSE KLGQYSSPDA KRCCQDGMTK LPMKRTCEQR AARVPQQACR EPFLSCCKFA  60
EDLRRNQTRS QAHLARNNHN MLQEEDLIDE DDILVRTSFP ENWLWRVEPV DSSKLLTVWL 120
PDSMTTWEIH GVSLSKSKGL CVAKPTRVRV FRKFHLHLRL PISIRRFEQF ELRPVLYNYL 180
NDDVAVSVHV TPVEGLCLAG GGMMAQQVTV PAGSARPVAF SVVPTAAANV PLKVVARGVF 240
DLGDAVSKIL QIEKEGAIHR EELVYNLDPL NNLGRTLEIP GSSDPNIVPD GDFSSLVRVT 300
ASEPLETMGS EGALSPGGVA SLLRLPQGCA EQTMIYLAPT LTASNYLDRT EQWSKLSPET 360
KDHAVDLIQK GYMRIQQFRK NDGSFGAWLH RDSSTWLTAF VLKILSLAQE QVGNSPEKLQ 420
ETASWLLAQQ LGDGSFHDPC PVIHRAMQGG LVGSDETVAL TAFVVIALHH GLDVFQDDDA 480
KQLKNRVEAS ITKANSFLGQ KASAGLLGAH AAAITAYALT LTKASEDLRN VAHNSLMAMA 540
EETGEHLYWG LVLGSQDKVV LRPTAPRSPT EPVPQAPALW IETTAYALLH LLLREGKGKM 600
ADKAASWLTH QGSFHGAFRS TQDTVVTLDA LSAYWIASHT TEEKALNVTL SSMGRNGLKT 660
HGLHLNNHQV KGLEEELKFS LGSTISVKVE GNSKGTLKIL RTYNVLDMKN TTCQDLQIEV 720
KVTGAVEYAW DANEDYEDYY DMPAADDPSV PLQPVTPLQL FEGRRS                766

SEQ ID NO: 85          moltype = AA  length = 291
FEATURE                Location/Qualifiers
source                 1..291
                       mol_type = protein
                       organism = Mus musculus
SEQUENCE: 85
EAPKVVEEQE SRVQYTVCIW RNGKLGLSGM AIADITLLSG FHALRADLEK LTSLSDRYVS  60
HFETDGPHVL LYFDSVPTTR ECVGFGASQE VVVGLVQPSS AVLYDYYSPD HKCSVFYAAP 120
TKSQLLATLC SGDVCQCAEG KCPRLLRSLE RRVEDKDGYR MRFACYYPRV EYGFTVKVLR 180
EDGRAAFRLF ESKITQVLHF RKDTMASIGQ TRNFLSRASC RLRLEPNKEY LIMGMDGETS 240
DNKGDPQYLL DSNTWIEEMP SEQMCKSTRH RAACFQLKDF LMEFSSRGCQ V          291
```

BISPECIFIC CONSTRUCTS FOR TARGET AND COMPLEMENT ENGAGEMENT

SEQUENCE LISTING

The instant application contains a Sequence Listing which has been submitted electronically in XML format and is hereby incorporated by reference in its entirety. Said XML copy, created on Mar. 8, 2024, is named 222237-701301-SL and is 137,893 bytes in size.

TECHNICAL FIELD

The present invention relates to macromolecules containing single domain antibodies capable of regulating one or more complement pathways by specific binding to human complement factors.

BACKGROUND

The complement system is part of the innate immune system and plays an important role in protection against invading microorganisms and in maintenance of homoeostasis. Uncontrolled activation or lack of proper regulation of complement is involved in a range of diseases and pharmacological inhibition of complement is believed to represent an attractive strategy to ameliorate disease outcome. This is exemplified by the clinical use of the monoclonal antibody eculizumab which reacts with complement factor C5.

The complement system is activated by three different proteolytic pathways: The classical pathway (CP), the lectin pathway (LP) and the alternative pathway (AP) (FIG. 1).

Therapeutic antibodies used in cancer treatment often rely on activating different parts of the immune system for optimal efficiency. However, only a subset of currently licensed antibodies activates the complement system and complement thus represents a severely underexploited mechanism for clearance of cancer cells but also pathogenic microorganisms.

A new single domain antibody based technology is therefore provided herein below, which potently and specifically modulate the complement system on target cells.

SUMMARY

The main object of the present disclosure is to describe single domain antibodies, also termed nanobodies, which are capable of modulating complement activity by specifically targeting epitopes of human complement factors.

In one aspect, single domain antibodies are provided, which are capable of specifically binding to an epitope of a human complement factor selected from the group consisting of C1q, C3, C4 and/or the proteolytic derivatives C3b and C4b.

In another aspect, a composition is provided, in particular a pharmaceutical composition, comprising a single domain antibody as defined above.

In a third aspect, a single domain antibody or a composition as defined above is provided for use as a medicament.

Another aspect provides a method of modulating the activity of the complement system, said method comprising
a) providing a composition comprising a human complement factor selected from the group consisting of C1q, C3, C4 and/or the proteolytic derivatives C3b and C4b,
b) contacting said composition with a single domain antibody as defined above.

In yet another aspect, a method is provided of treating a disorder associated with complement activation, said method comprising administering a therapeutically effective amount of a single domain antibody or composition as defined above.

In a further aspect, a method is provided of producing a single domain antibody, said method comprising immunizing a camelid with polypeptide comprising an epitope of a human complement factor selected from the group consisting of the human C1q, C3, C4 and/or the proteolytic derivatives C3b and C4b.

In a final aspect, a method is provided of detecting the presence of a complement factor selected from the group consisting of the human C1q, C3, C4 and/or the proteolytic derivatives C3b and C4b, wherein a single domain antibody as defined in any of the preceding claims is used as a detection agent.

DESCRIPTION OF DRAWINGS

FIGS. 2A-2D. (FIG. 2A) Binding of C1q to IgG immune complexes in the presence of different Nbs. (FIG. 2B) A subset of these Nbs prevent C4b deposition, and thus CP activation, in a concentration dependent manner. The assay measures C4b deposition in serial dilutions of normal human serum (NHS). (FIG. 2C) Updated comprehensive version of FIG. 2A. (FIG. 2D) Updated comprehensive version of FIG. 2B.

(FIG. 3A) Reconstruction based on electron microscopy, of the complex formed between C3b and the Nb D121, asterix marks the position of D121, and the epitope is the C3b C345c domain. (FIG. 3B) The crystal structure of the C-terminal domain of C3b in complex with D121 confirms this epitope mapping. (FIG. 3C) Size exclusion chromatography (SEC) analysis of the binding of C3b to FB in the presence of D121. (FIG. 3D) SDS-PAGE of fractions from SEC analysis of C3b+FB+D121. (FIG. 3E) Updated comprehensive version of FIG. 3C.

FIGS. 4A-4F. (FIG. 4A) SEC shows that DI62 does not prevent binding of C3b to FB suggesting that it acts by preventing binding of the substrate C3 to both the CP and the AP C3 convertases. Panels B-E compare the ability of DI62 and hC3Nb1 to inhibit the AP (FIG. 4B+FIG. 4C), LP (FIG. 4D) and CP (FIG. 4E). DI62 is able to inhibit both AP, LP and CP. (FIG. 4F) Updated comprehensive version of FIG. 4A.

FIGS. 5A-5E. (FIG. 5A) SEC analysis of the binding of EWE-hC3Nb1 to C3b. (FIG. 5B) SEC analysis of C3b. (FIG. 5C) SEC analysis of the binding of EWE-hC3Nb1 to C3. (FIG. 5D) SEC analysis of C3. (FIG. 5E) SDS-PAGE analysis of peak fractions from the indicated chromatograms shown in A and C.

FIGS. 6A-6E. (FIG. 6A) SEC analysis of the binding of IgG-Fc-hC3Nb1 to C3b. (FIG. 6B) SEC analysis of IgG-Fc-hC3Nb1. (FIG. 6C) SEC analysis of the binding of IgG-Fc-hC3Nb1 to C3. (FIG. 6D) SEC analysis of C3. (FIG. 6E) SDS-PAGE analysis of peak fractions from the indicated chromatograms shown in A and C.

FIGS. 7A-7B. The inhibitory effects of the nanobodies on AP C3 cleavage. hC3Nb1 (W102A) is a mutant of hC3Nb1 that does not bind to C3 or C3b. (FIG. 7A) Inhibition of C3 deposition using NHS diluted 1:9. (FIG. 7B) Inhibition of erythrocyte lysis using NHS diluted 1:6. The analysis includes measurement of the effect of Nbs on deposition of C3b on a surface of zymosan (FIG. 7A) or measurement of the effect of the Nbs on the lysis of rabbit erythrocytes (FIG. 7B) and is performed in a buffer eliminating the influence of CP and LP.

FIGS. 8A-8E: (FIG. 8A) SEC analysis of the interaction between C4 and hC4bNb6. (FIG. 8B) SEC analysis of the interaction between C4b and hC4bNb6. (FIG. 8C) SPR sensogram for apparent dissociation constant determination of C4: hC4bNb6. Full lines represent measured signal, dashed lines represent curve fit. (FIG. 8D) SPR sensogram for apparent dissociation constant determination of C4b: hC4bNb6. Full lines represent measured signal, dashed lines represent curve fit. (FIG. 8E) ka, kd and $k_D$ values±S.E.

FIGS. 9A-9C: (FIG. 9A) SEC analysis of the interaction between C4 and hC4Nb8. (FIG. 9B) SEC analysis of the interaction between C4b and hC4bNb8. (FIG. 9C) SDS-PAGE analysis of the SEC analysis experiment between C4 and hC4Nb8 shown in panel (A) suggesting that hC4Nb8 binds weaker to C4 as compared to C4b since the nanobody is not apparent in the fractions containing C4.

(FIG. 10A) SEC analysis of the interaction between C4b and C2 in the presence of hC4bNb6 and SDS-PAGE of fractions. (FIG. 10B) SEC analysis of the interaction between C4b and C2 in the presence of hC4Nb8 and SDS-PAGE of fractions.

(FIG. 11A) Inhibitory action of hC4bNb6 and hC4Nb8 on deposition of C4b in a CP activation assay on a surface of deposited IgG. 59IF75 is C1q inhibitor IF75 described above. None of the nanobodies inhibits C4 deposition. (FIG. 11B) Inhibitory action of hC4bNb6 and hC4Nb8 on deposition of C3b in a CP activation assay on a surface of deposited IgG. 59IF75 is C1q inhibitor IF75 described above. Two additional C4/C4b specific Nbs, hC4bNb4 and hC4bNb5 are also inhibitory, but with lower efficacy as compared to hC4bNb6 and hC4Nb8. The C2 specific hC2NbG5 used here has little effect on CP C3 deposition FIGS. 12A-12E. Bispecific C1q nanobodies and their ability to recruitment C1q and activate complement. (FIG. 12A) Constructs used in experiments. (FIG. 12B) Flow cytometry measurement of recruitment of C1q from human serum to Raji cells by BiCE161 (left). Incubation with BiCE161 results in complement activation and C3 deposition (right). Data are normalized. (FIG. 12C) Complement activation and C3 deposition by indicated bispecific nanobodies on EGFR expressing MDA-MB-468 cells. (FIG. 12D) Updated comprehensive version of FIG. 12B. (FIG. 12E) Updated comprehensive version of FIG. 12C.

FIGS. 13A-13H. Ability of DF85 and BiCE128 to recruit C1q and activate complement on different tumor cell lines. (FIG. 13A) Recruitment of C1q from human serum to MDA-MB-468, A431 and A1207 cells by DF85. (FIG. 13B) C3 deposition on MDA-MB-468, A431 and A1207 cells by DF85. (FIG. 13C) Recruitment of C1q from human serum to A431 and A1207 cells by BiCE161. (FIG. 13D) C3 deposition on A431 and A1207 cells by BiCE161. (FIG. 13E) Updated comprehensive version of FIG. 13A. (FIG. 13F) Updated comprehensive version of FIG. 13B. (FIG. 13G) Updated comprehensive version of FIG. 13C. (FIG. 13H) Updated comprehensive version of FIG. 13D.

(FIG. 23A) C3d deposition in the presence of control nb, D121 and hC3nb2 upon activation of the alternative pathway. D121 inhibits C3d deposition in a concentration dependent manner and DI62 inhibits at 10 µg/ml. (FIG. 23B) C3d deposition in the presence of control nb, D121 and hC3nb2 upon activation of the classical pathway. DI62 inhibit C3d deposition upon activation of the classical pathway while D121 and control nanobody have no effect on C3d deposition.

DETAILED DESCRIPTION

Figure 1:
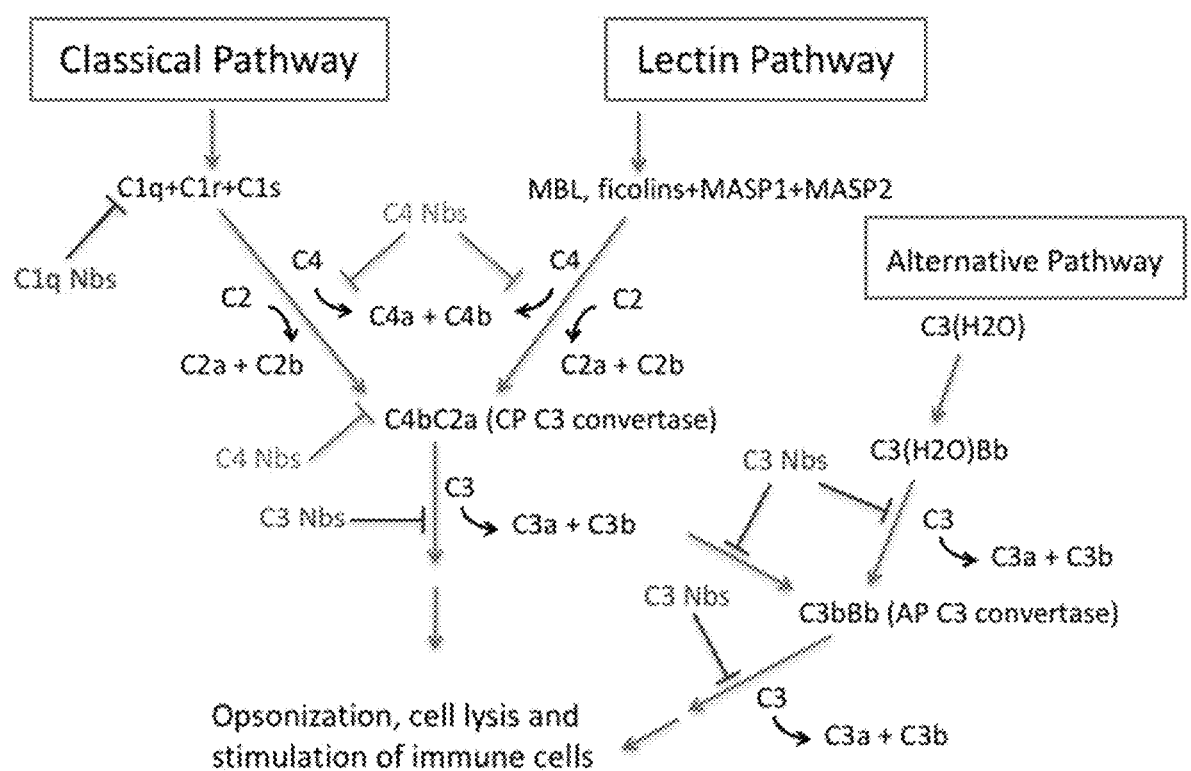
FIG. 1. Activation of the complement system and indications of where the identified Nbs (Nanobodies) inhibit complement.

Here, single domain antibodies, also called nanobodies (Nbs), are provided, which are derived from heavy-chain only camelid antibodies. The single domain antibodies disclosed herein are able to inhibit one or more complement pathways by specific binding to complement proteins. In order to facilitate the understanding of the invention, a number of important concepts are defined below

Definitions

An "antibody" is a polypeptide or protein capable of recognising and binding an antigen comprising at least one antigen binding site. Said antigen binding site preferably comprises at least one complementarity determining region (CDR). The present disclosure relates primarily to single domain antibodies.

The "single domain antibodies", as referred to herein, comprises only one single domain or fragment of a domain of a whole antibody. The single domain may be a heavy chain constant region ($C_H$), a heavy chain variable region ($V_H$), a light chain constant region ($C_L$) or a light chain variable region ($V_L$) or a fragment thereof. In a preferred embodiment the single domain is a heavy chain variable region ($V_H$). The single domain antibody is preferably derived from llama.

An "antigen" is a molecule comprising at least one epitope. The antigen may for example be a polypeptide, nucleic acid, polysaccharide, protein, lipoprotein or glycoprotein.

A "complementarity determining region" or "CDR" is a hypervariable region of the antigen-binding region of an antibody. The CDRs are interspersed between regions that are more conserved, termed framework regions (FRs). The antigen-binding region of an antibody may thus comprise one or more CDRs and FRs, usually in each variable domain three CDRs and four FRs arranged from amino-terminus to carboxy-terminus in the following order: FR1, CDR1, FR2, CDR2, FR3, CDR3, FR4.

An "epitope" is a determinant capable of specific binding to an antibody. Epitopes may for example be comprised within polypeptides or proteins. Epitopes may be continuous or discontinuous, wherein a discontinuous epitope is a conformational epitope on an antigen which is formed from at least two separate regions in the primary sequence of the protein, nucleic acid or polysaccharide.

Affinity: The strength of binding between receptors and their ligands, for example between an antibody and its antigen. The affinity of an antibody can be defined in terms of the dissociation constant, $K_D$, which is an equilibrium constant that measures the propensity of a molecular complex to separate (dissociate) reversibly into the molecules forming the complex. In one aspect, $K_D$ is defined as the ratio $k_{off}/k_{on}$, where $k_{off}$ and $k_{on}$ are the rate constants for association and dissociation of the molecular complex. Preferably affinity is determined by calculating the dissociation constant $K_D$ based on $IC_{50}$ values. Thus, the affinity is measured as an apparent affinity.

The term "residues", as used herein, generally refers to single monomers collectively making one polymer. More specifically, the monomers combined in making the single-domain antibodies provided herein, consist of amino acids making up a polypeptide or protein.

The term "linker", as used herein, refers to a molecular moiety used to covalently bind two molecules to one another. The linker may be of varying length and structure and may comprise different anchoring groups. In one embodiment, the anchoring group may be selected from the group consisting of amine, carboxylic acid, acid chloride, N-hydroxysuccinimide ester, maleimide, thiol or a polypeptide.

The term "treatment", as used herein, refers to any process, action, application, therapy, or the like, wherein a subject, including a human being, is subject to medical aid with the object of improving the animal's condition, directly or indirectly. Thus, a treatment may involve curative treatment, ameliorating treatment and/or prophylactic treatment, where prophylactic treatment can result in complete prevention of a clinical and/or physiological condition or reduce the severity, such as reducing the number of and severity of any symptom associated with the clinical and/or physiological condition.

The Complement System

The present invention relates to single domain antibodies targeting one or more human complement factors and thereby being able to modulate activation of the complement system.

The complement system is part of the innate immune system and plays an important role in protection against invading microorganisms and in maintenance of homoeostasis. The innate immune system is not adaptable and does not change over the course of an individual's lifetime. More than 50 proteins and protein fragments make up the complement system, including serum proteins, serosal proteins, and cell membrane bound receptors and regulatory proteins. A subset of the complement proteins circulates as inactive precursors (pro-proteins). When stimulated by one of several triggers, proteases in the system cleave specific proteins to initiate an amplifying cascade of further cleavages. The end-result of this activation cascade includes massive amplification of the response, enhanced phagocytosis and pathogen lysis, clearance of immune complexes and apoptotic cells, inflammation, stimulation of adaptive immune responses and assembly of the cell-killing membrane attack complex.

Uncontrolled activation or lack of proper regulation of complement is involved in a range of diseases and the present invention therefore provides means for pharmacological regulation of the complement cascade in order to ameliorate disease outcome.

More specifically, the complement system is activated by three different proteolytic pathways: The classical pathway (CP), the lectin pathway (LP) and the alternative pathway (AP) (FIG. 1). Activation of the complement system results in cleavage of the complement proteins C3 (all pathways) and C4 (the classical and lectin pathway) into C3a and C3b, and C4a and C4b, respectively. After a certain threshold of C3b density is reached on the complement activating surface activation of the terminal pathway (TP) results in cleavage of complement C5.

The CP is activated by the C1 complex formed by the pattern recognition molecule C1q and the serine proteases C1r and C1s. C1 recognizes several different ligands including antigen bound antibodies, which leads to activation of the C1 complex, but may also directly recognize danger-associated molecular patterns (DAMPs) and pathogen associated molecular patterns (PAMPs). C1 cleaves C4 into C4a and C4b, and C2 can now bind to C4b, and C2 is then cleaved by the C1 complex into C2a and C2b. C4bC2a is the CP C3 convertase that cleaves C3 into C3a and C3b.

The LP is initiated by recognition of carbohydrate or acetylated pathogen-associated molecular patterns (PAMPs) by mannose binding lectin (MBL), the collectin CL-LK and three ficolins, respectively. MBL. CL-LK and the ficolins are associated with MBL-associated serine proteases (MASP)-1 and -2 that are activated upon binding of MBL, CL-LK and ficolins to DAMPs and PAMPs. MASP-1 and MASP-2 activation triggers the same proteolytic cascade as the classical pathway and also leads to assembly of the CP C3 convertase.

The AP may be activated by a spontaneous hydrolysis of an internal thioester in C3, resulting in formation of C3 ($H_2O$). C3 ($H_2O$) associates with the protease factor B (FB), which is cleaved by factor D into Bb and Ba. The complex between C3 ($H_2O$) and Bb is the fluid phase AP C3 convertase that cleaves C3 into C3a and C3b. C3b reacts with nearby nucleophiles on surfaces and become covalently attached to these resulting in activator bound C3b. Such C3b associates with FB that is cleaved and the AP C3 convertase, C3bBb is formed. The AP C3 convertase cleaves C3 into C3b and C3a and more AP convertase is formed in an amplification loop (FIG. 1). The activator bound C3b may also originate from C3 cleavage conducted by the CP C3 convertase, and indeed the AP C3 convertase strongly amplifies the initial C3 cleavage taking place in the CP and LP.

The single domain antibodies provided herein target human complement factors, in particular a human complement factor selected from the group consisting of C1q, C3, C4 and/or the proteolytic derivatives C3b and C4b.

Binding of one or more of the single domain antibodies to any of the complement factors affects the activity of the complement system. In a preferred embodiment, the single domain antibody is capable of inhibiting activation of the complement system.

For example, antibodies targeting C1q are capable of inhibiting interaction with C1r and/or C1s or prevent C1q interaction with a CP activator and thereby inhibit assembly and/or activation of the C1 complex in the classical pathway.

Antibodies targeting C3 and/or C3b are capable of inhibiting interaction between C3b and the zymogen FB or the active Bb and thereby inhibit assembly of the C3bBb convertase complex and/or the activity of the C3bBb convertase, and/or are able to prevent binding of C3 to the C3 convertases of the alternative pathway and the classical pathway which in turn inhibits C3 cleavage.

Antibodies targeting C4 and/or C4b are capable of inhibiting interaction between the zymogen C2 or the active C2a with C4b and thereby inhibit assembly of the C4bC2a complex and/or the activity of the C4bC2a complex, which in turn inhibits activation of the classical and lectin pathways.

In the context of the present disclosure, it is understood that complement factor C4 includes both native allotypes, C4A and C4B; cf. SEQ ID NO: 6 and 80.

Single-Domain Antibodies

Naturally occurring human antibodies are heterotetramers. The antibodies provided herein in one aspect comprise an antigen binding site in a single polypeptide. The antibodies are therefore herein referred to as "single domain antibodies". Single domain antibodies are also known as nanobodies. The single antibodies disclosed herein may, though, in certain embodiment be bispecific or multispecific single domain antibodies as described elsewhere herein, where to single domain antibodies are coupled.

A single domain antibody is an antibody fragment consisting of a single monomeric variable antibody domain. Like a whole antibody, it is able to bind selectively to a specific antigen. Single domain antibodies typically have molecular weights in the range of 12-15 kDa, i.e. much lower than common antibodies, ranging typically from 150 to 160 kDa. Single domain antibodies are also smaller than Fab fragments (~50 kDa) of heterotetrameric antibodies comprising one light chain and half a heavy chain.

Single domain antibodies can derive from antibodies found in nature, for example in camelids ($V_HH$) and cartilaginous fishes ($V_{NAR}$). New or Nurse Shark Antigen Receptor (NAR) protein exists as a dimer of two heavy chains with no associated light chains. Each chain is composed of one variable (V) and five constant domains. The NAR proteins thus constitute a single immunoglobulin variable-like domain. Single heavy-chain antibodies are also found in camelids, such as such as dromedaries, camels, llamas and alpacas, where the heavy chain has lost one of its constant domains and underwent modifications in the variable domain, both of which are structural elements necessary for the binding of light chains.

However, single domain antibodies can also be engineered by recombinant methods. One approach is to split the dimeric variable domains from common immunoglobulin G (IgG) from humans or mice into monomers. Single domains, which are derived from light chains, also bind specifically to target epitopes. Thus, the single domain antibody may be derived from any suitable organism.

Single domain camelid antibodies are equal to regular antibodies in terms of specificity. Single domain antibodies are easily isolated, for example by using phage panning procedures. The smaller size and single domain architecture make these antibodies easier to express as proteins in bacterial cells for large scale production, making them ideal for commercial exploitation. The antibodies of the present invention are therefore single domain antibodies, preferably derived from camelid antibodies, preferably llama antibodies, including functional homologs, fragments thereof and fusion macromolecules containing VHH covalently linked to glycan, nucleic acid, protein, or chemical groups not being a macromolecule.

The single domain VHH antibodies of the present invention preferably comprise one or more CRDs. In particular, the CDRs may identify the specificity of the antibody and accordingly it is preferred that the antigen binding site comprises one or more CDRs, preferably at least 1, more preferably at least 2, yet more preferably 3 or more CDRs. In one specific embodiment, the single domain antibody comprises 3 CDRs.

Thus, the single-domain antibodies provided herein are preferably derived from natural antibodies, such as camelid antibodies, most preferred llama antibodies. The single-domain antibodies provided herein also include functional variants thereof. The term "functional variant" is meant to include those variants, which retain some or essentially all the ability of an antibody to selectively binding its antigen or ligand, such as any of the ligands mentioned herein below. Functional variants include any variant, which is at least 75% identical to a single-domain antibodies provided herein, such as at least 80, 81, 82, 83, 84, 85, 86, 87, 88, 89, such as 90, 91, 92, 93, 94, 95, 96, such as 97, such as 98, such as 99, such as at least 99.5% identical to a single-domain antibody provided herein, such as any of those identified by SEQ ID NOs: 9, 13, 17, 21, 25, 29, 33, 37, 41, 45, 49, 53, 57 and 61.

In particular, functional variants include any variant antibody comprising one or more CDR, which is at least 75% identical to a CDR of a single-domain antibodies provided herein, such as at least 80, 81, 82, 83, 84, 85, 86, 87, 88, 89, such as 90, 91, 92, 93, 94, 95, 96, such as 97, such as 98, such as 99, such as at least 99.5% identical to said CDR. The CDRs of the respective antibodies identified by SEQ ID NOs: 9, 13, 17, 21, 25, 29, 33, 37, 41, 45, 49, 53, 57 and 61 are indicated below as SEQ ID Nos: 10-12, 14-16, 18-20, 22-24, 26-28, 30-32, 34-36, 38-40, 42-44, 46-48, 50-52, 54-56, 58-60, and 62-64, respectively. Thus, single domain antibodies are provided, which comprise one or more region having at least 75%, such as at least 80, 81, 82, 83, 84, 85, 86, 87, 88, 89, such as 90, 91, 92, 93, 94, 95, 96, such as 97, such as 98, such as 99, such as at least 99.5% identity to one or more regions identified by any one of SEQ ID Nos: 10-12, 14-16, 18-20, 22-24, 26-28, 30-32, 34-36, 38-40, 42-44, 46-48, 50-52, 54-56, 58-60, and 62-64.

Any amino acid substitutions preferably do not include conservative amino acid substitutions, which refer to substitution of one amino acid with another amino acid residue having a side chain with similar properties. For example, a group of amino acids having aliphatic side chains is glycine, alanine, valine, leucine, and isoleucine; a group of amino acids having aliphatic-hydroxyl side chains is serine and threonine, a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

Within the meaning of the term "conservative amino acid substitution" as applied herein, one amino acid may be substituted for another within the groups of amino acids indicated herein below:
i) Amino acids having polar side chains (Asp, Glu, Lys, Arg, His, Asn, Gln, Ser, Thr, Tyr, and Cys)
ii) Amino acids having non-polar side chains (Gly, Ala, Val, Leu, Ile, Phe, Trp, Pro, and Met)
iii) Amino acids having aliphatic side chains (Gly, Ala Val, Leu, Ile)
iv) Amino acids having cyclic side chains (Phe, Tyr, Trp, His, Pro)
v) Amino acids having aromatic side chains (Phe, Tyr, Trp)
vi) Amino acids having acidic side chains (Asp, Glu)
vii) Amino acids having basic side chains (Lys, Arg, His)
viii) Amino acids having amide side chains (Asn, Gln)
ix) Amino acids having hydroxy side chains (Ser, Thr)
x) Amino acids having sulphur-containing side chains (Cys, Met),
xi) Neutral, weakly hydrophobic amino acids (Pro, Ala, Gly, Ser, Thr)
xii) Hydrophilic, acidic amino acids (Gln, Asn, Glu, Asp), and
xiii) Hydrophobic amino acids (Leu, Ile, Val)

Functional variants of antibodies may in one preferred embodiment be a fragment of an antibody, preferably an antigen-binding fragment or a variable region. Examples of antibody fragments useful with the present invention include fragments of $V_HH$ and $V_{NAR}$.

The single-domain antibodies may thus be obtained by immunization of any suitable organism, in particular camelids, sharks or the like.

However, the single domain antibodies could also be generated from a synthetic library with randomized or designed CDR's In one embodiment, a single domain antibody capable of specifically binding to an epitope of a human complement factor selected from the group consisting of C1q, C4 and/or the proteolytic derivative C4b, C3 and/or the proteolytic derivative C3b is provided.

In a preferred embodiment, the single-domain antibody comprises a variable region including a polypeptide consisting of the amino acid sequence represented by SEQ ID Nos: 10-12, 14-16, 18-20, 22-24, 26-28, 30-32, 34-36, 38-40, 42-44, 46-48, 50-52, 54-56, 58-60, and 62-64.

In addition, the single domain antibodies provided herein may be coupled to a tag, such as any purification tag or detectable label. In one embodiment, the single domain antibody is coupled to a histidine tag, such as a his6 tag at the N- or C-terminus of the polypeptide. In another embodiment, the single domain is coupled to an Fc-fragment at the N-terminal. N-terminal additions are particularly preferred, and in a preferred embodiment, the single domain antibody provided herein comprises an additional N-terminal region. The additional N-terminal region can be selected from any relevant additional moieties, depending on the contemplated application of the antibody and the desired functionalities to the final antibody product. Albumin may be added for increasing circulation time and protect the product from degradation. Other antigen binding fragments, single domain antibodies or fragments thereof may be added for introducing a second affinity/binding specificity to the antibody product.

In one embodiment, the single domain antibody is selected from the group consisting of EA57, IF75, IF78, IH31, IH33, IH35, IH37, IH39, hC4bNb6, hC4Nb8, D121, DI62, EWE-hC3Nb1 and IgG-Fc-hC3Nb1, identified by SEQ ID Nos: 9, 13, 17, 21, 25, 29, 33, 37, 41, 45, 49, 53, 57 and 61, respectively. In a preferred embodiment, the single domain antibody is selected from the group consisting of IF75, IH37 and EA57. In another preferred embodiment, the single domain antibody is EWE-hC3Nb1 or IgG-Fc-hC3Nb1. In another embodiment, the single domain antibody is selected from the group consisting of hC4bNb6, hC4Nb8, D121 and DI62.

Epitope

The single domain antibodies provided herein are capable of specifically binding to an epitope of a human complement factor. In a preferred embodiment, the antibody is capable of specifically binding to an epitope of a human complement factor selected from the group consisting of C1q, C3, C4 and/or the proteolytic derivatives C3b and C4b. Thus, the single domain antibody is capable of specifically binding to an epitope in a region in any of the polypeptide sequence identified by SEQ ID Nos: 1-8, 74-75 and 80-82.

In a preferred embodiment, the antibody is capable of specifically binding an epitope selected from
- an epitope, wherein at least a part of the epitope is situated in the region of
  - i) human C1q chain a identified by SEQ ID NO: 3,
  - ii) human C1q chain b identified by SEQ ID NO: 4,
  - iii) human C1q chain c identified by SEQ ID NO: 5 and/or
- an epitope, wherein at least a part of the epitope is situated in the region of
  - i) human C3 identified by SEQ ID NO: 1,
  - ii) mouse C3 identified by SEQ ID NO: 2,
  - iii) mouse C3 identified by SEQ ID NO: 74,
  - iv) mouse C3 identified by SEQ ID NO: 75.
- an epitope, wherein at least a part of the epitope is situated in the region of
  - i) human C4A or C4B alpha chain,
  - ii) human C4A or C4B beta chain and/or
  - iii) human C4A or C4B gamma chain.
- an epitope, wherein at least a part of the epitope is situated in the region of
  - i) mouse C4 alpha chain identified by SEQ ID NO: 84,
  - ii) mouse C4 beta chain identified by SEQ ID NO: 83, and/or
  - iii) mouse C4 gamma chain identified by SEQ ID NO: 85.

The term "situated" as used in this context, means that the epitope is located or positioned in the specified region of the human C1q, C3, C3b, C4 or C4b.

It is preferred that the single domain antibodies as described herein binds their target complement factor with an affinity corresponding to a $K_D$ of about $10^{-4}$ M or less, such as about $10^{-5}$ M or less, such as about $10^{-6}$ M or less, $10^{-7}$ M or less, such as about $10^{-8}$ M or less, such as about $10^{-9}$ M or less, about $10^{-10}$ M or less, or about $10^{-11}$ M or even less, when measured based on apparent affinities based on $EC_{50}$ values (the effective concentration achieving 50% of maximal binding) in an ELISA assay. In one embodiment, the antibody binds said complement factor with an affinity corresponding to a $K_D$ of about $10^{-6}$ M or less, such as $10^{-6}$ to $10^{-18}$ M.

The antibody may also or alternatively bind their target complement factor with an affinity corresponding to a $K_D$ that is at least ten-fold lower, such as at least 100-fold lower, such as at least 1000-fold lower than its affinity for binding to a non-specific antigen (e.g., BSA or casein).

The single domain antibody (or nanobody) may in some embodiment be cross-reactive. By cross-reactive is herein understood that the antibody reacts with an antigen from two or more species. Thus, it is an embodiment of the present invention that a single domain antibody binds one or more complement factors from one or more species. By way of example, the antibody may bind the human and mouse C4. Preferably the cross reactivity is between human and another mammalian species such as but not limited to mouse, rabbit, sheep, goat, pig, llama and horse. It is an object of the present invention to provide a single domain antibody, optionally an antibody which is bispecific, which binds human and mouse C3, human and mouse C3b, human and mouse C1q, human and mouse C4, and/or human and mouse C4b. The antibody may bind complement factors and/or their (proteolytic) derivatives from one or more species, preferably human and mouse.

TABLE 1

Overview of single domain antibodies and their antigens.

| Antibody | hC3 | hC3b | mC3 | mC3b | hC4 | hC4b | mC4 | mC4b | hC1q |
|---|---|---|---|---|---|---|---|---|---|
| DI62 | + | + | + | + | | | | | |
| D121 | + | + | + | + | | | | | |
| EWE-hC3Nb1 | | + | | + | | | | | |
| IgG-Fc-hC3Nb1 | | + | | + | | | | | |
| hC4bNb6 | | | | | | + | | + | |
| hC4Nb8 | | | | | | + | | | |
| hC4Nb4 | | | | | | + | | + | |
| hC4Nb5 | | | | | | + | | + | |
| pNSL270 | | | | | | | + | + | |
| EA57 | | | | | | | | | + |
| IF75 | | | | | | | | | + |
| IF78 | | | | | | | | | + |
| IH31 | | | | | | | | | + |
| IH33 | | | | | | | | | + |
| IH35 | | | | | | | | | + |
| IH39 | | | | | | | | | + |

+ indicates binding.

All the antibodies listed in Table 1 are object of the present invention.

TABLE 2

Binding Constants - DI62.

| | $K_D$ | $k_a$ (1/Ms) | $k_d$ (1/s) |
|---|---|---|---|
| Nat C3 | 5.5 nM | 1.0 * 10^5 | 5.7 * 10^−4 |
| C3b | 4.7 nM | 6.2 * 10^4 | 2.9 * 10^−4 |
| C3MA | 3.2 nM | 8 * 10^4 | 2.6 * 10^−4 |

Table 2 depicts the binding constants of the interaction between DI62 and native C3, C3b and C3MA.

Bispecific Single Domain Antibodies and Fusion Macromolecules

The single domain antibody may also be a bispecific antibody, e.g. a single peptide chain comprising two antigen-binding regions, which may each be separated by a linker sequence. The single domain antibody may also be a multivalent antibody, e.g. a single peptide chain comprising multiple antigen-binding regions, which may each be separated by linkers. The antigen-binding regions may be identical or different, yielding monospecific or heterospecific antibodies, respectively.

Thus, in one embodiment, a single domain antibody provided herein is coupled to another single domain antibody, yielding a bispecific antibody, which consists of or comprises
  i) one single domain antibody capable of specifically binding to an epitope of a human complement factor selected from the group consisting of C1q, C3, C4 and/or the proteolytic derivatives C3b and C4b and
  ii) one single domain antibody capable of specifically binding to an epitope of a second target.

The two or more single domain antibodies are coupled by a linker region. The linker can be chosen from any suitable linkers, such as polypeptide linkers. In one embodiment, the peptide linker comprises 5-50 amino acids, such as 5-30 amino acids, such as 5-20 amino acids, such as 5-10 amino acids. In one specific embodiment, the linker comprises 10 amino acids, for example GGGGSGGGGS.

In one embodiment, the second target is another complement factor. However, in preferred embodiments, the second target is a cancer-specific marker, such as any marker that is differentially expressed in cancer cells compared to non-malignant cells, where the marker is over-expressed on cancer cells. The second target is in another embodiment a pathogenic marker, in particular a microbial pathogen. In another embodiment, the second marker is a tissue-specific marker, an organ-specific marker, such as a marker specific for lung, eye, brain or kidney.

Single domain antibodies, which are capable of specifically binding to an epitope of a human complement factor selected from the group consisting of C1q, C3, C4 and/or the proteolytic derivatives C3b and C4b, are described elsewhere herein.

Single domain antibodies, which are capable of specifically binding to an epitope of a of a second target, include antibodies binding any target, for which the recruitment of a complement factor selected from C1q, C3, C4 and/or the proteolytic derivatives C3b and C4b is relevant.

For example, the coupling a single domain antibody specifically binding a complement factor to a cancer-specific target enables recruitment of complement factors and complement activation to the cancer target and consequently a targeted immunological response directed towards the cancer cells.

Similarly by coupling a single domain antibody specifically binding a complement factor to a single domain antibody specifically binding a pathogenic marker enables recruitment of complement factors and complement activation to the pathogen and consequently a targeted immunological response directed towards the pathogen. Coupling to the single domain antibody to another single domain antibody targeting specific tissues or organs could also be used to recruit complement factors to those specific tissues or organs leading to either activation or inhibition of the complement system at these tissues or organs.

Cancer-specific markers are for example EGFR and/or CD38, both cell bound receptors, which are upregulated in several cancer forms. Another group comprises cell specific marker proteins for example CD19 and CD20 both membrane proteins presented by B lymphocytes and validated targets for treatment of B cell lymphomas. Other examples of suitable markers are cMET, CD33, CD22, CD52, VEGF, PSMA, EpCam, HER, GD3, Erb2 and CD30.

Pathogenic markers include markers of bacterial, viral and fungal infections. These include for example the structures making up the membrane of gram negative bacteria like LPS or conserved proteins and structures in the membrane. Relevant markers could be part of the peptidoglycan cell wall of Gram positive bacteria like teichoic acid lipoteichoic acid. Suitable markers for viral infections include surface proteins on viral particles like influenza hemagglutinin or HIV-1 envelope trimer. Fungal infections can be targeted via conserved fungal surface antigens.

Bispecific single domain antibodies can be used to recruit and activate the complement cascade to specific targets, such as cancer sites or sites of infections, and thereby specifically activate an innate immune response at a specific target.

Such bispecific antibodies are therefore particularly useful in medicine for use as a medicament, and particularly for use in treatment of cancer and/or microbial infections.

In one aspect, the single domain antibodies provided herein, which are capable of specifically binding to an epitope of a human complement factor selected from the group consisting of C1q, C3, C4 and/or the proteolytic derivatives C3b and C4b are fused to another entity or moiety. For example, the single domain antibody may be covalently linked to a glycan, PEG, nucleic acid, protein, such as albumin, Fc-fusion or linked other chemical groups, such as small chemical molecules.

Antibody Modifications

The single domain antibodies disclosed herein above, may in preferred embodiments comprise modifications, which improve the function of the antibody.

For example, it is not always desirable to use non-human antibodies for human therapy, and accordingly the single domain antibodies provided herein may be a humanized antibody.

The antibody according to the invention may be a humanized antibody. A human antibody as used herein is an antibody, which is obtained from a system using human immunoglobulin sequences. Human antibodies may for example be antibodies isolated from an animal (e.g., a mouse) that is transgenic or transchromosomal for human immunoglobulin genes or a hybridoma prepared therefrom. Human antibodies may also be isolated from a host cell transformed to express the antibody, e.g., from a transfectoma. Human antibodies may also be isolated from a recombinant, combinatorial human antibody library or directly cloned from human B cells.

Human antibodies have variable and constant regions derived from human germline immunoglobulin sequences. In certain embodiments, however, such recombinant human antibodies can be subjected to in vitro mutagenesis or in vivo somatic mutagenesis and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

A human antibody is preferably at least 90%, more preferably at least 95%, even more preferably at least 96%, 97%, 98%, or 99% identical in amino acid sequence to the amino acid sequence encoded by a wild type human immunoglobulin gene.

Said transgenic of transchromosomal animal may contain a human immunoglobulin gene miniloci that encodes unrearranged human heavy (μ and/or γ) and κ light chain immunoglobulin sequences. Furthermore, the animal may contain one or more mutations that inactivate the endogenous heavy and light chain loci.

The single domain antibody of the invention may be a chimeric antibody, i.e. an antibody comprising regions derived from different species. The chimeric antibody may for example comprise variable regions from one species of animal and constant regions from another species of animal. For example, a chimeric antibody can be an antibody having variable regions which derive from a lama monoclonal antibody and constant regions which are human. Such antibodies may also be referred to as humanized antibodies. The single domain antibodies can advantageously be humanized in order to prevent immunological reactions of the human organism against the antibody.

Thus, the single domain antibodies provided herein may be a humanized antibody, which is encoded partly by sequences obtained from human germline immunoglobulin sequences and partly from other sequences. Said other sequences are preferably germline immunoglobulines from other species, which produce single domain antibodes, most preferably from camelidae species, such as llama. In particular a humanized antibody may be an antibody in which the antigen binding site is derived from an immunoglobulin from lama, whereas some or all of the remaining immunoglobulin-derived parts of the molecule is derived from a human immunoglobulin. The antigen binding site from said lama may for example consist of a complete VHH or one or more CDRs grafted onto appropriate human framework regions. Thus, in a humanized antibody, the CDRs can be from camelids or cartilaginous fishes, preferably lama, and the other regions of the antibody are of human origin.

In other embodiments, the single domain antibodies are modified by codon optimization or other modifications introduced in order to enhance the function of the antibody.

Composition

One aspect of the present invention relates to a composition comprising one or more of the single domain antibodies provided herein. In one preferred embodiment, the composition is a pharmaceutical composition.

A pharmaceutical composition is a composition comprising one or more substances that have medicinal properties, together with a pharmaceutical acceptable carrier. Details of pharmaceutical compositions are provided herein below.

The single domain antibodies can be formulated as pharmaceutical compositions and administered to a mammalian host, such as a human patient in a variety of forms adapted to the chosen route of administration. Routes for administration include, for example, intravenous, intra-arterial, subcutaneous, intramuscular, intraperitoneal, intravitreal and other routes selected by one of skill in the art. Administration can also be achieved by nebulization. In another approach, the single domain antibodies may be administered as DNA by AAV and then expressed from the vector Administration forms are described elsewhere herein.

Solutions of the antibodies can for example be prepared in water or saline, and optionally mixed with a nontoxic surfactant. Composition for intravenous or intra-arterial administration may include sterile aqueous solutions that may also contain buffers, liposomes, diluents and other suitable additives. The pharmaceutical composition may also comprise or include serum.

The pharmaceutical dosage forms suitable for injection or infusion can include sterile aqueous solutions or dispersions comprising the active ingredient that are adapted for administration by encapsulation in liposomes. In all cases, the ultimate dosage form must be sterile, fluid and stable under the conditions of manufacture and storage.

Sterile injectable solutions are prepared by incorporating the antibodies in the required amount in the appropriate solvent with various of the other ingredients enumerated above, as required, followed by filter sterilization.

Methods and Uses of the Antibody

The single domain antibodies and compositions provided herein can be used for both in vivo and in vitro methods as well as medical and non-medical procedures.

In one aspect, the single domain antibodies and compositions provided herein are provided for use as a medicament. In a preferred embodiment the single domain antibodies and compositions are provided for treatment of a disorder, a clinical or physiological condition associated with complement activity. The single domain antibodies and compositions can also be applied for use in the preparation of a medicament, for example for the treatment of a disorder, a clinical or physiological condition associated with complement activity.

Another aspect relates to a method of treating a disorder, a clinical or physiological condition associated with complement regulation, such as complement activation, said method comprising administering a therapeutically effective amount of a single domain antibody or composition as defined in any of the preceding claims to s subject in need thereof.

The antibodies can be used alone or coupled to, or combined with, therapeutically useful agents. Antibodies can be administered to mammals suffering from any disease caused by dysregulation or over activation of the complement system or any of the diseases or clinical conditions mentioned herein. Such administration can provide therapeutic and curative treatments, as well as prophylactic, preventative and/or ameliorating measures.

One aspect of the present invention relates to a method of modulating the activity of the complement system using the antibody according to the present invention. Thus, a method is provided of modulating the activity of the complement system, said method comprising
 a) providing a composition comprising a human complement factor selected from the group consisting of C1q, C3, C4 and/or the proteolytic derivatives C3b and C4b,
 b) contacting said composition with single domain antibody capable of specifically binding to an epitope of a human complement factor selected from the group consisting of C1q, C3, C4 and/or the proteolytic derivatives C3b and C4b, as defined elsewhere herein.

Thus, the methods and uses provided herein may involve the provision of a single domain antibody of the present invention for modulating the activity of the complement system, which means that some of the single domain antibodies are capable of inhibiting the activity of the complement system and other single domain antibodies are capable of activating or increasing the activity of the complement system. In particular, where the single domain antibody is administered locally or is coupled to an agent, which promotes a localized accumulation, the complement system can be targeted to a specific region of interest, for example a tumour site or a site of microbial infection.

The methods and uses provided herein are in certain embodiments capable of inhibiting the initiation of the classical pathway, the lectin pathway, and/or the alternative pathway.

In other embodiments, the methods and uses provided herein are capable of activating the classical pathway and thereby the alternative pathway.

For example, the single domain antibodies EA57, IF75 and IH37 are capable of specifically binding to an epitope of the human C1q thereby inhibiting C1q interaction with IgG. However, the same antibodies may be capable of activating the C1 complex when the antibody is bound to a surface.

Single domain antibodies D121, EWE-hC3Nb1 and IgG-Fc-hC3Nb1 bind C3b and C3 (H2O) thereby being capable of inhibiting assembly and/or the activity of the C3bBb convertase and the $C_3$ (H2O) convertase, which in turn inhibits the alternative pathway For this purpose, the single domain antibody hC3Nb1 comprising an additional N-terminal region is generally capable of specifically binding C3b and prevents binding of C3 to the C3 convertases. While any N-terminal addition is contemplated, specifically relevant additions include albumin, antigen-binding regions, such as other single domain antibodies and fragments thereof.

In particular, EWE-hC3Nb1 and IgG-Fc-hC3Nb1 specifically binds C3b and not C3. These antibodies are particularly useful in vivo setting, since C3 is present in high concentrations (>4 µM in serum) while C3b is only located locally at sites of complement activation. Furthermore, single domain antibodies also binding C3 may in certain in vivo applications lead to formation of large immune complexes, if formulated into a dimeric format such as an N-terminal Fc-fusion protein. The C3b specific antibodies therefore allow a highly specific targeting of C3b as compared to C3 and have fewer adverse effects during in vivo applications.

Single domain antibody DI62 binds C3 and C3b and prevents binding of C3 and C3b to the C3 convertases.

In one aspect, a method is provided of modulating the activity of the complement system. This method comprises a composition comprising a human complement factor selected from the group consisting of C1q, C3, C4 and/or the proteolytic derivatives C3b and C4b, and contacting the composition with a single domain antibody capable of specifically binding to an epitope of a human complement factor selected from the group consisting of C1q, C3, C4 and/or the proteolytic derivatives C3b and C4b, i.e. a single domain antibody as defined herein above.

The composition is typically a bodily fluid or a cell culture. In preferred embodiments, the composition is serum, plasma, blood or cerebrospinal fluid.

In one embodiment, the method is an in vitro method. An in vitro method, as referred to herein, is a method performed outside a living organism or outside the body of a living organism or an individual. The method may for example be performed in laboratory containers, such as in a test tube, an incubation vessel, petri dishes, flasks or the like. The single domain antibodies can thus be used in vitro for modulation of complement activation in cell cultures of any kind.

The in vitro method may comprise the steps of i) providing a composition comprising a human complement factor selected from the group consisting of C1q, C3, C4 and/or the proteolytic derivatives C3b and C4b; and ii) contacting said composition with said single domain antibody, thereby modulating the activity of the complement factors.

When contacting the composition with the single domain antibody, the antibody will bind and either block or stimulate the functional activity of the complement factor.

The composition may comprise any protein or one or more proteins involved in the complement system, including serum proteins, serosal proteins, and cell membrane receptors. Proteins involved in the complement system include for example C2, C4, C5, C3b, C3a, C4a, C4bC2a, C5a, C3bBb, factor B, factor D, germline-encoded pattern recognition receptors (PRR's) (such as mannose-binding lectin (MBL) or ficolins), MBL-associated serine proteases (MASPs)-1 or -2, properdin, C1q, C1r or C1s, The composition may also comprise other proteins with a function equivalent to the function of one or more complement proteins, e.g. CVF.

PRRs bind to conserved structures present in large groups of microorganisms popularly referred to as pathogen-associated molecular patterns (PAMPs). Thus, the composition as described above may also comprise PAMPs. Examples of PAMPs include endotoxin or lipopolysaccharide of Gram-negative bacteria, lipoteichoic acid of Gram-positive bacteria and beta-glucan of fungi.

The composition may also comprise pathogenic and/or cancer-specific markers.

The composition may comprise components such as therapeutically useful agents as described elsewhere herein.

In an alternative embodiment the method is an in vivo method.

The in vivo method may comprise the steps of administering to an individual the single domain antibody and thereby modulating the activity of the complement system in said individual.

Preferably, the single domain antibody at least partially inhibits the activity of the complement system in said individual. However, in other embodiments, specific activating or recruiting antibodies can activate the complement system or stimulate the activity of the complement system, either in general (systemically) or by recruiting the relevant complement factor to which it binds to a specific target region, e.g. where the single domain antibody is a bispecific antibody, as described above.

In particular, the in vivo method may comprise the steps of administering to an individual the single domain antibody according to the invention in an amount sufficient to modulate, i.e. inhibit or increase the activity of the classical pathway, the lectin pathway and/or the alternative pathway in said individual.

The in vivo method may comprise the steps of administering to an individual suffering from a disorder or clinical or physiological associated with increased activity of the complement system a therapeutically effective amount of one or more of the single domain antibodies provided herein.

In another embodiment, the in vivo method comprises the steps of administering to an individual suffering from a disorder or clinical or physiological condition, which is treatable by increasing and/or recruiting the activity of the complement system, a therapeutically effective amount of one or more of the single domain antibodies provided herein, including bispecific antibodies.

The in vivo method may be any of the method of treating any of the clinical or physiological conditions mentioned herein.

Disorder, Clinical and Physiological Conditions

The composition or the single domain antibodies according to the invention may be used as a medicament for treatment of disorders, clinical or physiological conditions caused by a defect in the complement system or more specifically an increased activity of the complement system or lack of (sufficient) complement activation. Such disorders, clinical or physiological conditions that involve the complement system are described below. The pharmaceutical composition may be used for the treatment of any of those.

The single domain antibodies and compositions provided herein can be provided for treatment of any disorder selected from the group consisting of ocular diseases, neurological diseases, autoimmune and inflammatory disorders, cancers and infectious diseases.

Thus, in one preferred embodiment, the composition or the single domain antibodies are provided for use in treatment of ocular diseases. Ocular diseases may be selected from the group consisting of Occular, acute closed angle glaucoma, all stages of age-related macular degeneration (wet and dry), Behcet's retinopathy, Central Retinal Vein Occlusion (CRVO), choroidal neovascularization (CNV), Chronic open-angle glaucoma, corneal neovascularization, diabetic and other ischemia-related retinopathies, diabetic macular edema, diabetic retinopathy, endophthalmitis, Geographic atrophy, histoplasmosis of the eye, ischemia-related retinopathy, ischemic optic neuropathy, Leber's hereditary optic neuropathy, macular degenerative diseases, Neuromyelitis Optica (NMO), pathological myopia, Purtscher retinopathy, retinal neovascularization, Sjogren's dry eye disease Uveitis.

In another preferred embodiment, the composition or the single domain antibodies are provided for use in treatment of neurological diseases, such as diseases selected from the group consisting of Alzheimer's disease, schizophrenia, amyotrophic lateral sclerosis, Guillain-Barre syndrome, Huntington's disease, multiple sclerosis and Parkinson's disease.

In yet another preferred embodiment, the composition or the single domain antibodies are provided for use in treatment of autoimmune and inflammatory disorders, such as disorders selected from ANCA vasculitis, anti-nuclear cytoplasmic antigen-associated pauci-immune vasculitis (Wegener's syndrome), anti-phospholipid syndrome (APS), astma, atypical hemolytic uremic syndrome (aHUS), autoimmune hemolytic anemias, Bullous Pemphigoid, C3 glomerulonephritis, Coeliac disease, Cold agglutinin disease, Crohn's disease, cryogbulemia, dense deposit disease, dermatomyositis, diabetes, Diabetes mellitus type 1, epidermolysis bullosa, Hashimoto's thyroiditis, hyperacute rejection. hypocomplementemic urticarial vasculitis (HUV), IgA nephropathy, intestinal and renal ischemia-reperfusion (IR) injury, lupus nephritis and resultant glomerulonephritis and vasculitis, Myasthenia Gravis, myositis, optic neuritis, paraneoplastic syndromes, paroxysomal nocturnal hemoglobinuria (PNH), pemphigus including Pemphigus vulgaris, polyarteritis nodosa, polymyalgia rheumatic, post-traumatic shock, acute renal failure, remote tissue injury after ischemia and reperfusion retinal vasculitis, rheumatoid arthritis (RA), sarcoidosis, sepsis, stroke, systemic lupus erythematosus (SLE), temporal arteritis, traumatic brain and spinal cord injury, type II membranoproliferative glomerulonephritis, vasculitis disease, vitiligo, acute respiratory distress syndrome (ARDS), chronic occlusive pulmonary distress syndrome (COPD), atherosclerosis, cardioplegia-induced coronary endothelial dysfunction, spontaneous and recurrent pregnancy loss, Addison's disease.

In another preferred embodiment, the composition or the single domain antibodies are provided for use in treatment of cancers such as carcinomas, sarcomas, lymphomas, leukaemia's, germ cell tumor, blastoma.

In another preferred embodiment, the composition or the single domain antibodies are provided for use in treatment of infectious diseases such as infections with bacteria, viruses, parasites or fungi.

Administration Forms

As described herein above, the single domain antibodies and/or compositions provided herein can be used for medical/therapeutic treatment. In these aspects, the single domain antibodies and/or compositions are administered to a subject in need of treatment, and any suitable route of administration may be chosen, depending on the circumstances. Preferred routes of administration are described herein below.

Systemic Treatment

The main route of administration is parenteral in order to introduce single domain antibodies according to the invention into the blood stream to ultimately target the sites of desired action.

Appropriate dosage forms for such administration may be prepared by conventional techniques.

Parenteral Administration

Parenteral administration is any administration route not being the oral/enteral route whereby the medicament avoids first-pass degradation in the liver. Accordingly, parenteral administration includes any injections and infusions, for example bolus injection or continuous infusion, such as intravenous administration, intramuscular administration, subcutaneous administration. Furthermore, parenteral administration includes inhalations and topical administration.

Accordingly, the single domain antibodies or compositions may be administered topically to cross any mucosal membrane of an animal to which the biologically active substance is to be given, e.g. in the nose, vagina, eye, mouth, genital tract, lungs, gastrointestinal tract, or rectum, preferably the mucosa of the nose, or mouth, and accordingly, parenteral administration may also include buccal, sublingual, nasal, rectal, vaginal and intraperitoneal administration as well as pulmonal and bronchial administration by inhalation or installation. Also, the agent or antibody may be administered topically to cross the skin.

The subcutaneous and intramuscular forms of parenteral administration are generally preferred.

Pharmaceutical Composition

Whilst it is possible for the single domain antibodies provided herein to be administered in raw form, it is preferred to present them in the form of a pharmaceutical composition. Accordingly, the present invention further provides a pharmaceutical composition, which comprises a single domain antibody of the present invention and a pharmaceutically acceptable carrier therefore. The pharmaceutical compositions may be prepared by conventional techniques, e.g. as described in Remington: The Science and Practice of Pharmacy 2005, Lippincott, Williams & Wilkins.

The pharmaceutically acceptable carriers can be either solid or liquid. Solid form preparations include powders, tablets, pills, capsules, cachets, suppositories, and dispersible granules. A solid carrier can be one or more excipients which may also act as diluents, flavoring agents, solubilizers, lubricants, suspending agents, binders, preservatives, wetting agents, tablet disintegrating agents, or an encapsulating material.

The single domain antibodies of the present invention may be formulated for parenteral administration and may be presented in unit dose form in ampoules, pre-filled syringes, small volume infusion or in multi-dose containers, optionally with an added preservative. The compositions may take such forms as suspensions, solutions, or emulsions in oily or aqueous vehicles, for example solutions in aqueous polyethylene glycol. Examples of oily or non-aqueous carriers, diluents, solvents or vehicles include propylene glycol, polyethylene glycol, vegetable oils (e.g., olive oil), and injectable organic esters (e.g., ethyl oleate), and may contain agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The single domain antibodies of the invention may be administered in the form of an alkali metal or earth alkali metal salt thereof, concurrently, simultaneously, or together with a pharmaceutically acceptable carrier or diluent, especially and preferably in the form of a pharmaceutical composition thereof, whether by rectal or parenteral (including subcutaneous) route, in an effective amount.

Examples of pharmaceutically acceptable acid addition salts for use in the present inventive pharmaceutical composition include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic acids, and arylsulphonic, for example.

Dosages and Dosing Regimes

The dosage requirements will vary with particular composition employed, the route of administration and the subject being treated. It will also be recognized by one of skill in the art that the optimal quantity and spacing of individual dosages of the single domain antibody will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of the antibody given per day for a defined number of days, may be ascertained using conventional course of treatment determination tests.

The daily oral dosage regimen may range from about 0.01 to about 80 mg/kg of total body weight. The daily parenteral dosage regimen may range from about 0.001 to about 80 mg/kg of total body weight. The daily topical dosage regimen will preferably be from 0.1 mg to 150 mg, administered one to four, preferably two or three times daily.

The daily inhalation dosage regimen will preferably be from about 0.01 mg/kg to about 1 mg/kg per day.

The single domain antibodies may be provided and/or administered as a unit dosage form. The term "unit dosage form" as used herein refers to physically discrete units suitable as unitary dosages for human and animal subjects, each unit containing a predetermined quantity of the single domain antibody, alone or in combination with other agents, calculated in an amount sufficient to produce the desired effect in association with a pharmaceutically acceptable diluent, carrier, or vehicle. The specifications for the unit dosage forms of the present invention depend on the particular antibody or antibodies employed and the effect to be achieved, as well as the pharmacodynamics associated with each antibody in the host. The dose administered should be an "effective amount" or an amount necessary to achieve an "effective level" in the individual patient.

When the "effective level" is used as the preferred endpoint for dosing, the actual dose and schedule can vary, depending on inter-individual differences in pharmacokinetics, drug distribution, and metabolism. The "effective level" can be defined, for example, as the blood or tissue level desired in the patient that corresponds to a concentration of one or more antibodies according to the invention.

The antibodies of the present invention may be formulated in a wide variety of compositions for parenteral administration.

For injections and infusions the compositions may take such forms as suspensions, solutions, or emulsions in oily or aqueous vehicles, for example solutions in aqueous polyethylene glycol. Alternatively, the single domain antibodies may be in powder form, obtained by aseptic isolation of sterile solid or by lyophilisation from solution for constitution before use with a suitable vehicle, e.g., sterile, pyrogen-free water. The compositions can be presented in unit dosage form or multi-dose sealed containers, such as ampoules, vials, pre-filled syringes, infusion bags, or can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Examples of oily or non-aqueous carriers, diluents, solvents or vehicles include propylene glycol, polyethylene glycol, vegetable oils, and injectable organic esters, and may contain formulatory agents such as preserving, wetting, emulsifying or suspending, stabilizing and/or dispersing agents.

The compositions for injection will typically contain from about 0.5 to about 25% by weight of the active ingredient in solution.

The compositions of the present embodiment may also include other agents useful for pH maintenance, solution stabilization, or for the regulation of osmotic pressure.

The compositions of the present embodiment may also include other agents useful for pH maintenance, solution stabilization, or for the regulation of osmotic pressure.

Method of Producing a Single Domain Antibody

One aspect of the present disclosure relates to methods of producing single domain antibodies as defined herein, i.e. single domain antibodies capable of specifically binding to an epitope of a human complement factor selected from the group consisting of C1q, C3, C4 and/or the proteolytic derivatives C3b and C4b. The single-domain antibodies may be obtained by immunization of any suitable organism. In particular, single-domain antibodies provided herein may be derived by immunization of any organism known to naturally possess immunoglobulins consisting of heavy chain only, such as camelids, sharks or the like.

Thus, one aspect relates to a method of producing a single domain antibody, said method comprising immunizing a camelid, such as such as a dromedary, camel, llama or an alpaca, with peptide comprising an epitope of a human complement factor selected from the group consisting of the human C1q, C3, C4 and/or the proteolytic derivatives C3b and C4b. The camelid is preferably a llama The relevant epitopes are epitopes are described herein above, and includes for example
  an epitope, wherein at least a part of the epitope is situated in the region of
    iv) human C1q chain a identified by SEQ ID NO: 3,
    v) human C1q chain b identified by SEQ ID NO: 4,
    vi) human C1q chain c identified by SEQ ID NO: 5 and/or.
  an epitope, wherein at least a part of the epitope is situated in the region of human C3 identified by SEQ ID NO: 1.
  an epitope, wherein at least a part of the epitope is situated in the region of
    i) human C4A or C4B alpha chain identified by SEQ ID NO: 6 or 80,
    ii) human C4A or C4B beta chain identified by SEQ ID NO: 7 and/or
    iii) human C4A or C4B gamma chain identified by SEQ ID NO: 8.

The method preferably involves immunization of the animal, such as camelid, such as lama, with the desired epitope/antigen, is followed by isolating the mRNA encoding heavy-chain antibodies. Subsequently, the mRNA can be reverse transcribed and amplified by polymerase chain reaction (PCR), thereby producing a gene library of single-domain antibodies clones. Specific clones, which are capable of specifically binding to an epitope of a human complement factor selected from the group consisting of C1q, C3, C4 and/or the proteolytic derivatives C3b and C4b, can then be identified using screening techniques, such as phage display or ribosome display.

Upon identification of the most specific and high affinity single domain antibodies, their protein sequence can be optimized, for example to improve their stability towards enzymes. The relevant antibodies may also be humanized as described herein above to prevent immunological reactions of the human organism against the antibody. Camelid antibodies are easily humanized due to a large degrees of the homology between camelid VHH and human VH fragments. The single-domain antibody may be produced in cells of host organisms such as *Escherichia coli, Saccharomyces cerevisiae, Pichia pastoris, Spodoptera frugiperda, Trichoplusia ni, Homo sapiens*, CHO, or other suitable organisms by transferring the gene encoding the single domain antibody to said host organism and allowing the gene to be expressed in sufficient amounts for the resulting single domain antibody to be isolated. Such methods of heterologous gene expression are generally known in the art.

Method of Detecting the Presence of a Complement Factor

A number of highly specific and high affinity single domain antibodies are provided herein, which are capable of specifically binding to an epitope of a human complement factor selected from the group consisting of C1q, C3, C4 and/or the proteolytic derivatives C3b and C4b. Such antibodies can be used for detection of said complement factors as well as their interaction partners. Thus, in one aspect, a method is provided for detecting the presence of a complement factor, preferably a complement factor selected from the group consisting of the human C1q, C3, C4 and/or the proteolytic derivatives C3b and C4b. In this method, a single domain antibody as defined herein above is used as a detection agent. The single domain antibody is therefore preferably coupled to a detectable label.

The method for detecting the presence of a complement factor is in one embodiment an in vitro method. For example, such as in vitro method comprise the steps of
a. Providing a biological sample,
b. Providing a single domain antibody as defined herein above,
c. Bringing said single domain antibody into contact with said biological sample, and
d. Detecting the binding of said single domain antibody to one or more complement factors in said biological sample.

The method may preferably involve additional steps of washing away unbound single domain antibody from the sample and/or addition of secondary antibodies or other detection agents followed by detection of bound secondary antibodies or other detection agents.

In another embodiment, the method is an in vivo method, wherein said single domain antibody is administered to a subject followed by detection of the presence of the antibody in said subject.

The method for detecting the presence of a complement factor is in one preferred embodiment a diagnostic method, comprising administering the single domain antibody to a subject suffering or at risk of suffering of a disorder associated with complement activation and detecting the presence of the antibody in said subject.

The method may be applied for detecting concentration of complement factors in specific tissues of a subject.

In one embodiment, the diagnostic method is applied for determining the presence or risk of a disorder selected from the group consisting of Autoimmune and inflammatory disorders, such as disorders selected from ANCA vasculitis, anti-nuclear cytoplasmic antigen-associated pauci-immune vasculitis (Wegener's syndrome), anti-phospholipid syndrome (APS), astma, atypical hemolytic uremic syndrome (aHUS), autoimmune hemolytic anemias, Bullous Pemphigoid, C3 glomerulonephritis, Coeliac disease, Cold agglutinin disease, Crohn's disease, cryoglobulemia, dense deposit disease, dermatomyositis, diabetes, Diabetes mellitus type 1, epidermolysis bullosa, Hashimoto's thyroiditis, hyperacute rejection. hypocomplementemic urticarial vasculitis (HUV), IgA nephropathy, intestinal and renal ischemia-reperfusion (IR) injury, lupus nephritis and resultant glomerulonephritis and vasculitis, Myasthenia Gravis, myositis, optic neuritis, paraneoplastic syndromes, paroxysomal nocturnal hemoglobinuria (PNH), pemphigus including Pemphigus vulgaris, polyarteritis nodosa, polymyalgia rheumatic, post-traumatic shock, acute renal failure, remote tissue injury after ischemia and reperfusion retinal vasculitis, rheumatoid arthritis (RA), sarcoidosis, sepsis, stroke, systemic lupus erythematosus (SLE), temporal arteritis, traumatic brain and spinal cord injury, type II membranoproliferative glomerulonephritis, vasculitis disease, vitiligo, acute respiratory distress syndrome (ARDS), chronic occlusive pulmonary distress syndrome (COPD), atherosclerosis, cardioplegia-induced coronary endothelial dysfunction, spontaneous and recurrent pregnancy loss, Addison's disease.

In another embodiment, the diagnostic method is applied for determining the presence of complement activation during or after transplantation.

In another embodiment, the diagnostic method is applied for in-body/in vivo detection of activated C3b or C4b.

EXAMPLES

Example 1

Single Domain Antibodies Against C1q that Inhibit C1 Activation.

For selection of single domain C1q was purified by the protocol described by Tenner et al., 1981. Immunization and selection was performed using 0.4 mg of human C1q essentially as described by Jensen et al., 2018 for C3. Nanobodies were expressed in *E. coli* using 2×TY media overnight. Pelleted cells were resuspended in 20 mM Tris pH 8.0, 500 mM NaCl, 0.5 mM EDTA, 20 mM imidazole, sonicated and subjected to His-Trap crude FF (GE Healthcare) column. The nanobody was eluted by imidazole supplemented resuspension buffer. The eluted protein was dialyzed overnight against 20 mM acetic acid (pH 5.5), 50 mM NaCl, then applied to 1 mL Source 15S (GE Healthcare) column and eluted by a linear gradient from 50-500 NaCl. The eluted protein was subjected to size exclusion chromatography using Superdex 75 (GE Healthcare) column.

For CP deposition assays, 96-well Optical Bottom Microwell® Plates were coated with normal human IgG (nhIgG) diluted in carbonate buffer pH=9.6 (AmpliqON) to 15 µg/mL. The plates were incubated in humidity box at room temperature overnight, after which they were blocked by addition of human serum albumin (HSA) at 1 mg/mL diluted in TBS, 0.05% w/w Tween 20, 5 mM Ca2+ (TBS/Tween/Ca2+) and incubated at room temperature for 1 hour. The plates were washed three times with TBS/Tween/Ca2+ (wash step). The samples containing the desired nanobody were added to the wells in duplicates and incubated for 1 hour at 37° C. in humidity box, followed by a wash step. The assay was developed by adding biotin kahC4c (Dako 0.78 mg/mL) at 0.5 µg/mL concentration, diluted in TBS/Tween/Ca2+. The plates were incubated at 4° C. in humidity box overnight, followed by a wash step. Europium3+-streptavidin (1244-360; PerkinElmer, Waltham, MA) diluted to 0.1 mg/ml in TBS/Tween/25 µM EDTA was added to each well and protein deposition levels were quantified as the fluorescent signal from Eu3+, after addition of 200 µl enhancement buffer (AmpliqON) to each well. The signals were measured by time-resolved fluorometry using a VICTOR X5 plate reader (PerkinElmer), with an excitation and an emission wavelength of 350 nm and 610 nm, respectively.

The globular head of C1q (hC1gGH) was generated as described by Moreau et al. 2016, but now including a C-terminal his-tag. The protein was expressed by stably transfected HEK293F cells and loaded on a 1 ml HisTrap excel column. The column was washed in 50 ml PBS and eluted with PBS supplemented with 250 mM imidazole pH 8.0. The eluted protein was diluted in PBS containing 500 mM NaCl and loaded on a 1 ml HisTrap crude column. The column was washed with PBS containing 500 mM NaCl and 20 mM imidazole pH 8.0 and eluted with PBS supplemented with 250 mM imidazole pH 8.0. The eluted protein was concentrated and loaded on a Superdex 200 Increase column equilibrated in 20 mM hepes, 150 mM NaCl pH 7.5. To analyse complex formation between C1qGH and IF75, IF75 was mixed with C1qGH in a two-fold molar excess and loaded on an ENrich70 SEC 70 10×300 column equilibrated in 20 mM hepes, 150 mM NaCl pH 7.5. The eluted protein was analysed by SDS-PAGE.

Figure 2A:
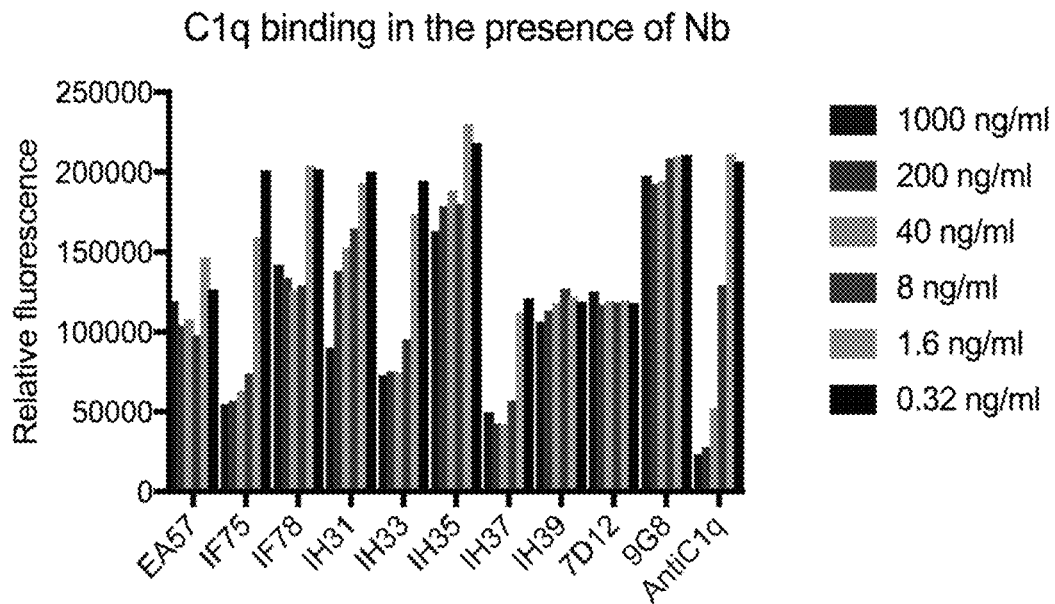
Figure 2B:
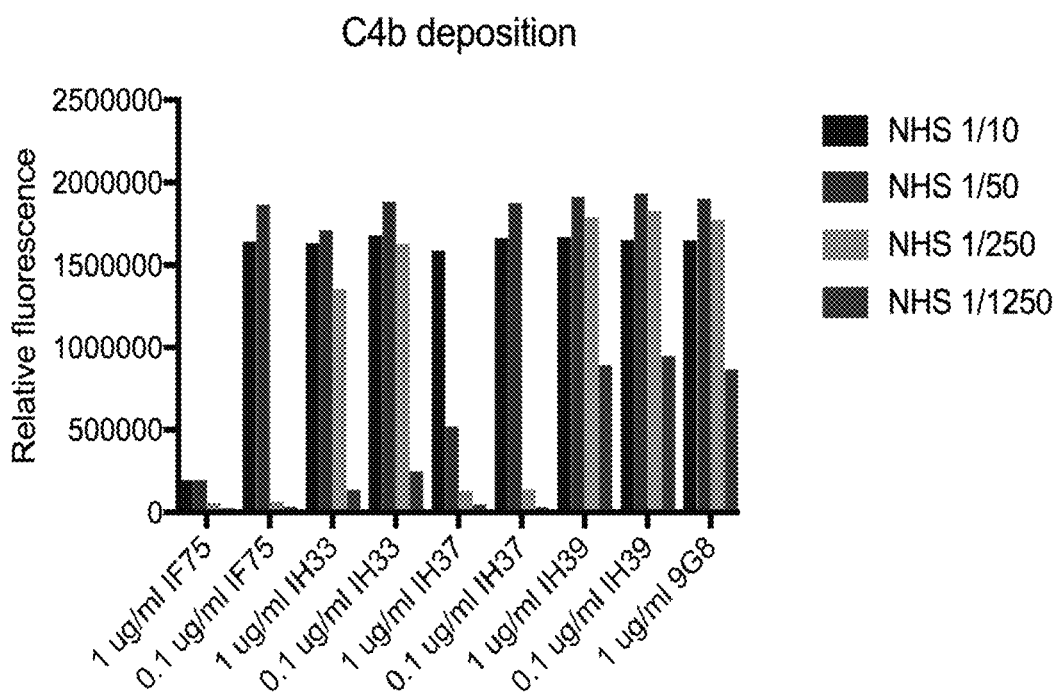

FIGS. 2A-2D show binding of C1q to wells coated with IgG in the presence of increasing amount of C1q nanobodies (FIG. 2A) and the inhibitory effects of nanobodies on CP activation (FIG. 2B). As observed in FIG. 2A, IF75, IH33 and IH37 potently prevents the interaction with IgG while EA57, IF78, IH31 are less potent. IH35 and IH39 do not inhibit binding of C1q to IgG. As demonstrated in FIG. 2B, IH75, IH33 and IH37 inhibits C1 activation by IgG in a dose dependent manner.

Figure 17:
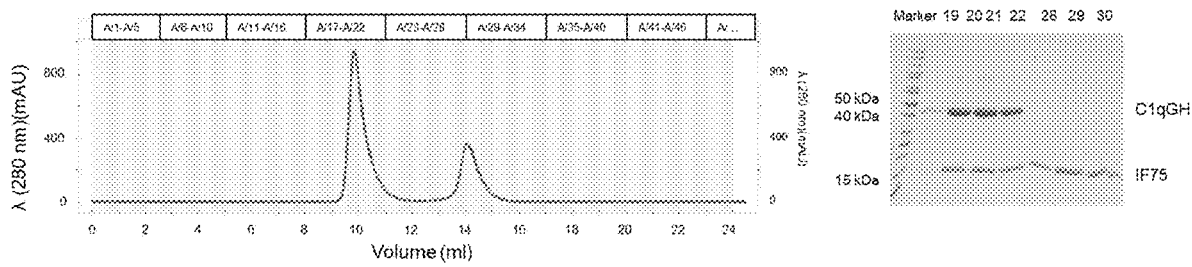
FIG. 17. SEC of the complex between the globular head of human C1q (hC1qGH) and IF75 on a ENrich 70 10/300 column (left). SDS-PAGE of indicated fractions (right). As seen from the SDS-PAGE IF75 interacts specifically with the head region of hC1q.
Figure 18:
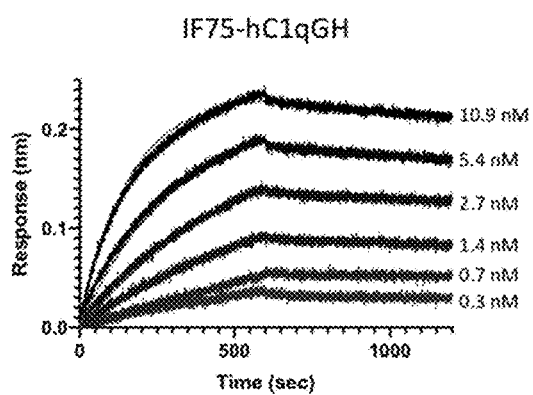
FIG. 18. Bio-layer interferometry (BLI) measurements of the interaction between hC1qGH and IF75. IF75 was immobilized on the sensors and numbers are concentrations of hC1qGH. Global fitting to the data shows that hC1qGH binds to IF75 with a dissociation constant of 0.5 nM.
Figure 19:
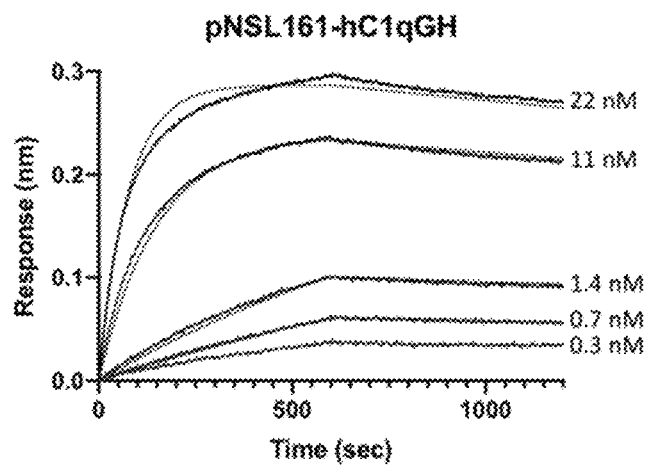
FIG. 19. Bio-layer interferometry (BLI) measurements of the interaction between hC1qGH and the bispecific nanobody pNSL161 composed IF75 linked to a CD38 specific nanobody. pNSL161 was immobilized on the sensors and numbers are concentrations of hC1qGH. Global fitting to the data shows that hC1qGH binds to pNSL161 with a dissociation constant of approximately 0.5 nM.

FIG. 17 shows that IF75 binds specifically to the globular head of C1q in SEC. The interaction was also measured by Bio-layer interferometry (BLI) as shown in FIG. 18. IF75 binds to hC1qGH with a dissociation constant (Kd) of 0.5 nM.

Example 2

Inhibitory Nanobodies Against C3 and C3b.

Native C3 was purified from outdated human plasma as descried elsewhere (Jensen et al., 2018). Similarly, C3b was generated from the purified native C3 as described elsewhere (Jensen et al., 2018). Immunization and selection of nanobodies D121 and DI62 were performed essentially as described by Jensen et al., 2018. Nanobodies were purified as described in Example 1. For negative stain electron microscopy, D121 was added in two fold molar excess to C3b followed by 5 min incubation on ice. The complex was purified using a Superdex 200 increase (GE Healthcare) size exclusion column equilibrated in 20 mM HEPES (pH 7.5), 150 mM NaCl. 3 μL complex from the early peak fractions were applied to glow-discharged carbon coated copper grid, followed by staining with 2% (w/V) uranyl formate. Image acquisition was performed on FEI Tecnai G2 Spirit transmission electron microscope operated at 120 kV. Automated image acquisition was performed using Leginon (Suloway et al., 2005), automated particle picking was performed using DoG picker (Voss et al., 2009). 2D and 3D classification was performed using RELION (Scheres, 2012).

For crystallization, D121 was added in 10% molar excess to mC3 C345c and subjected to size exclusion chromatography using a Superdex 75 (GE Healthcare) column equilibrated in 20 mM HEPES (pH 7.5), 150 mM NaCl. The complex was concentrated to 10 mg/mL and mixed in a 1:1 ratio with reservoir solution containing 17.5% PEG 4K, 33 mM NaOAc (pH 4.3), 66 mM NaOAc (pH 5.3), 0.2 M AmSO4 in a sitting drop crystallization setup at 19° C. Crystals were soaked in reservoir solution supplemented with 20% glycerol before being flash frozen in liquid nitrogen. Data was processed with XDS (Kabsch, 2010) and the structure was determined using the C345c and hC3nb1 for molecular replacement in Phaser (McCoy et al., 2007). The model was iteratively manually rebuilt in Coot (Emsley, 2007) and refined using Phenix.refine (Afonine, 2007). To assay inhibition of assembly of the AP C3 proconvertase, 50 μg C3b was added a 1.2-fold molar excess of FB (D279G S/A) and subjected to size exclusion chromatography either alone or in presence of a twofold molar excess of the indicated nanobody. The complexes were incubated for 5 min at 4° C. before being subjected to the size exclusion chromatography (SEC), which was performed at 4° C. on a Superdex 200 increase (GE Healthcare) equilibrated in 20 mM HEPES (pH 7.5), 150 mM NaCl, 3 mM MgCl2.

To assay cleavage by factor I, Factor H and Factor I was added to C3b and incubated 5 min on ice with a 1.2-fold molar excess of the nanobody. The reaction buffer was 150 mM NaCl, 20 mM HEPES (pH 7.5) and the Factor H and Factor I ratio was 1/500 and 1/100 mass ratio to C3b, respectively. The reaction mix was incubated at 37° C. Samples were obtained after 1, 2, 4, and 8 h, mixed with reducing SDS loading dye and boiled to prevent further cleavage.

To analyse cleavage by the CVFBb convertase, the CVFB proconvertase was prepared by mixing FB (D279A mutant) with a two-fold molar excess of CVF in 150 mM NaCl, 20 mM HEPES (pH 7.5), 2 mM MgCl2. 10% (w/w) FD was added to activate the convertase, and the mix was incubated for 15 min at RT, then 10 min on ice. For EWE-hC3nb1 and D121, a 10-fold molar excess of C3 to FB was added and the reaction was incubated on ice, either in presence or absence of a two-fold molar excess (to C3) of the nanobody. For hC3nb2, a 10-fold molar excess of C3 to FB was added and the reaction was incubated at 37° C. in either the presence or absence of a two-fold molar excess (to C3) of the nanobody. Samples were obtained after 0.5, 1, 2, 4, 8, and 24 h, mixed with reducing SDS loading dye and boiled to prevent further cleavage.

To measure the interaction between nanobodies and C3 or C3b Bio-layer interferometry (BLI) experiments were performed in 20 mM HEPES (pH 7.5), 150 mM NaCl, 0.05% (v/v) Tween 20 on an Octet RED96 instrument (FORTÉBIO Pall Corporation). Biotinylated nanobody, at 5 μg/mL, was immobilized on streptavidin biosensor (FORTEBIO Pall Corporation). Nanobody coated biosensors were transferred to native C3 or C3b at concentration 6.25, 12.5, 25, and 50 nM with an association time of 600 sec. Upon association, a 1400 sec dissociation step was performed.

For the D121/FP/miniFH competition assay, miniFH was immobilized on amine reactive sensors (AR2G, ForteBio). The sensors were equilibrated in $H_2O$ for 5 min before being activated in a mixture of 20 mM 1-ethyl-3-(3-dimethylaminopropyl)-carbodiimide) and 10 mM N-hydroxysuccinimide for 5 min. MiniFH was then loaded at 20 μg/mL in 10 mM sodium acetate, 100 mM NaCl pH 5.0 for 10 min before the sensors were quenched with 1 M ethanolamine for 5 min. The sensors were equilibrated in the assay buffer (PBS supplemented with 1 mg/mL BSA and 0.05% Tween 20) for 5 min. The association of either C3b (280 nM), FP (94 nM), D121 (714 nM), C3b+FP (280 nM and 94 nM, respectively), C3b+D121 (280 nM and 714 nM, respectively) and C3b+FP+D121 (280 nM, 94 nM and 714 nM, respectively) were assessed for 60 s followed by a 60 s dissociation step in assay buffer. The assay was repeated twice after regeneration of the sensors using PBS supplemented with 4 M of NaCl. The FP used for the assay was approximately 90% dimer and 10% trimer as judged by SEC analysis performed on a 24 mL Superdex200 Increase column.

EWE-hC3Nb1 was generated by cloning a glutamate, tryptophan, glutamate (EWE) motif into the N-terminal of hC3nb1 (Jensen et al., 2018) and purified as in example 1. IgG-Fc-hC3Nb1 was generated by fusing the hC3nb1 nanobody to the C-terminal of the hIgG1 insert in pFUSE-N (Invitrogen) using overlap extension PCR. HEK 293f cells were transfected with the plasmid in a DNA:polyethylenimine ratio of 1:2.5. The conditioned media was harvested 5 days after transfection. The pH of the media was adjusted by application of 20 mM Tris:HCl (pH 8.5) and the media was applied to His-trap Excel (GE Healthcare). The protein was eluted by imidazole, concentrated and applied to Superdex 200 increase (GE Healthcare) column. To analyze binding of IgG-Fc-hC3Nb1 and EWE-hC3Nb1 to C3 and C3b, 140 µg C3b or native C3 was mixed 1:1 molar ratio to the IgG-Fc-hC3Nb1/EWE-hC3Nb1. The complex was incubated 5 min on ice, then applied to Superdex 200 increase (GE Healthcare) column equilibrated in 20 mM HEPES (pH 7.5), 150 mM NaCl for size exclusion chromatography.

AP and LP disposition assays were performed as described by Jensen et al., 2018.

Figure 3A:
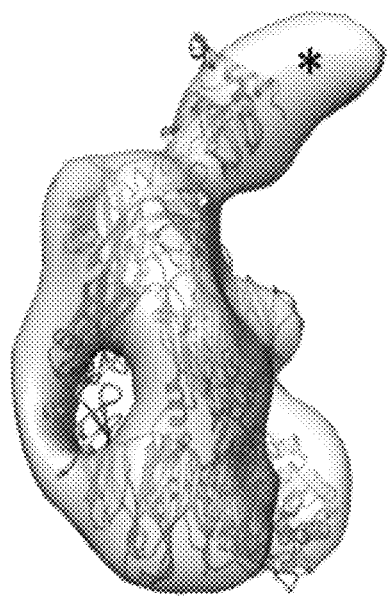
FIGS. 3A-3E.
Figure 3B:
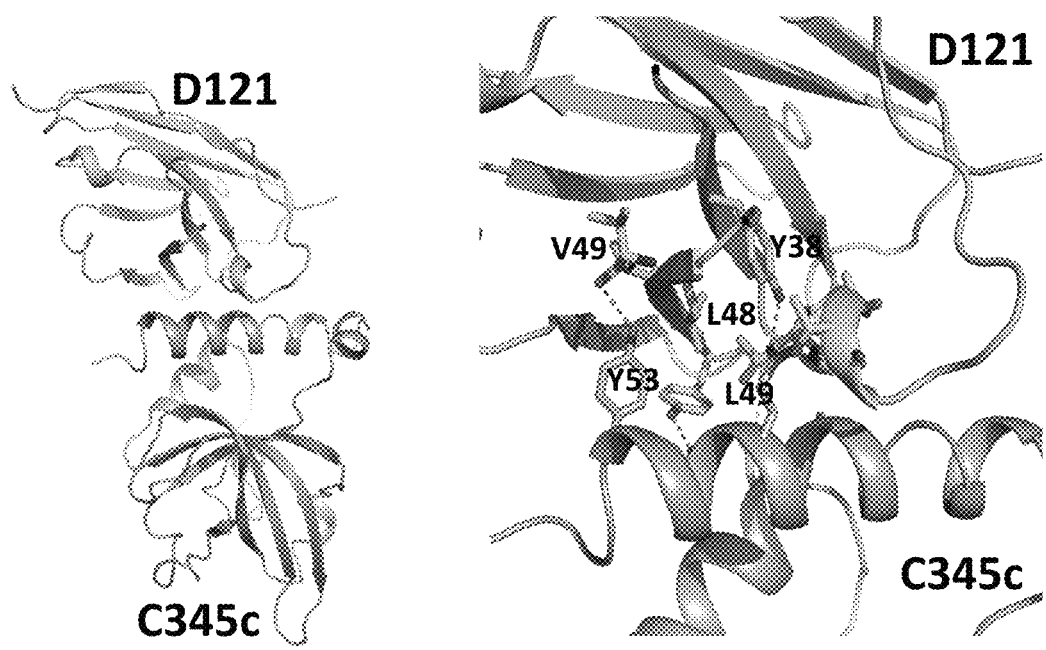
Figure 3C:
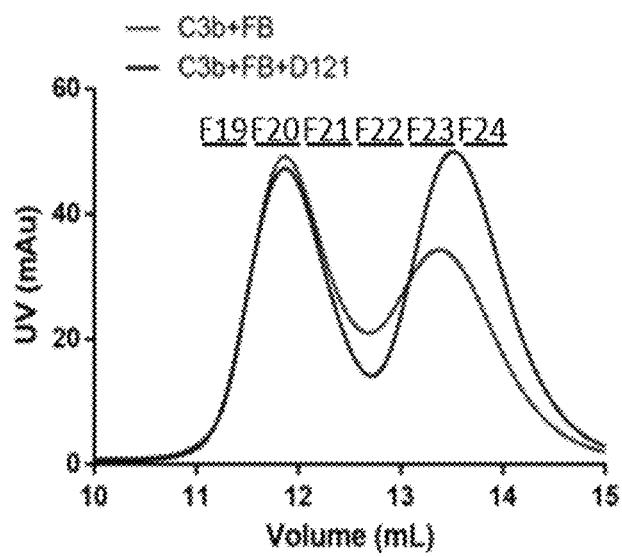
Figure 3D:
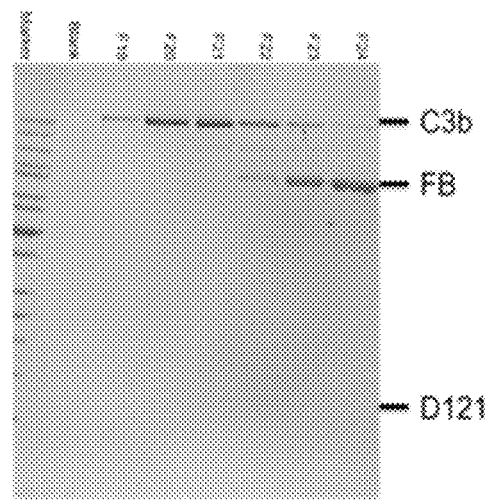
Figure 3E:
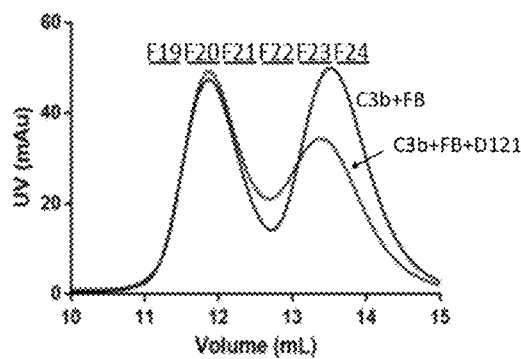

FIG. 3A shows that excess density corresponding to D121 (indicated by *) is present at the C-terminal C345c domain of C3b suggesting that D121 binds the C345c domain. FIG. 3B shows the crystal structure of D121 bound to the C345c domain of C3, confirming that the epitope of D121 is in the C345c domain of C3. As demonstrated in FIG. 3C and FIG. 3D, D121 prevents assembly of the AP C3 proconvertase C3bFB in SEC.

Figure 23A:
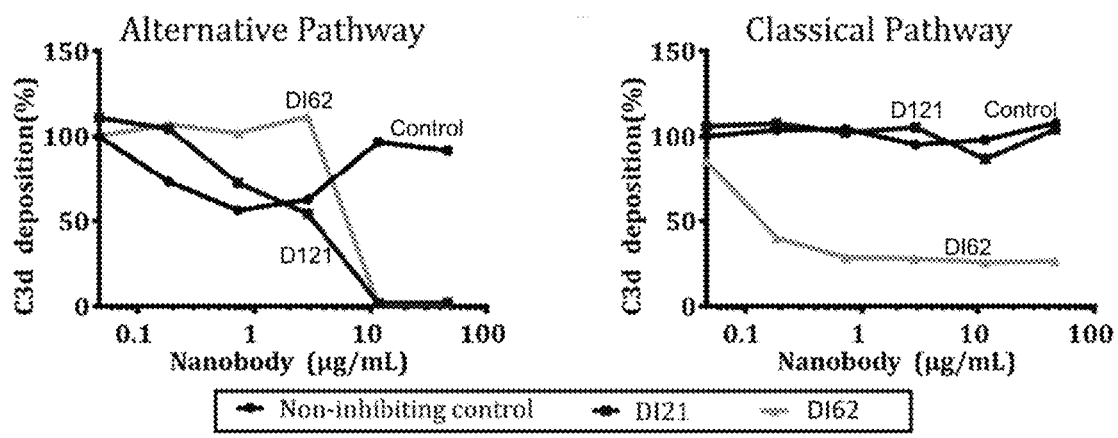
FIGS. 23A-23B. Effect of D121 and DI62 on C3d deposition in the alternative and classical pathways.
Figure 23B:
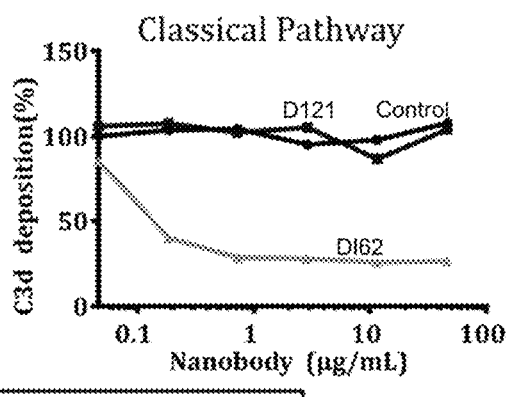
Figure 24:
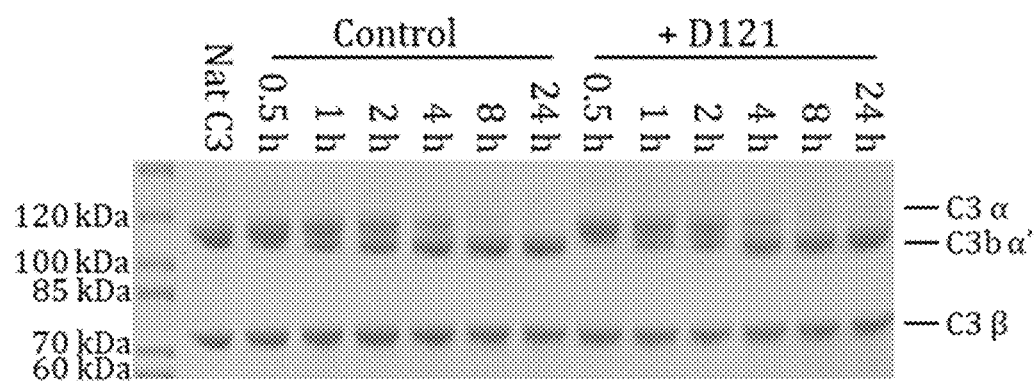
FIG. 24. CVF-Bb mediated cleavage of native C3. Cleavage of C3 into C3b in the presence or absence of D121. D121 does not inhibit the cleavage of C3 into C3b (generation of C3b alpha' chain).
Figure 25:
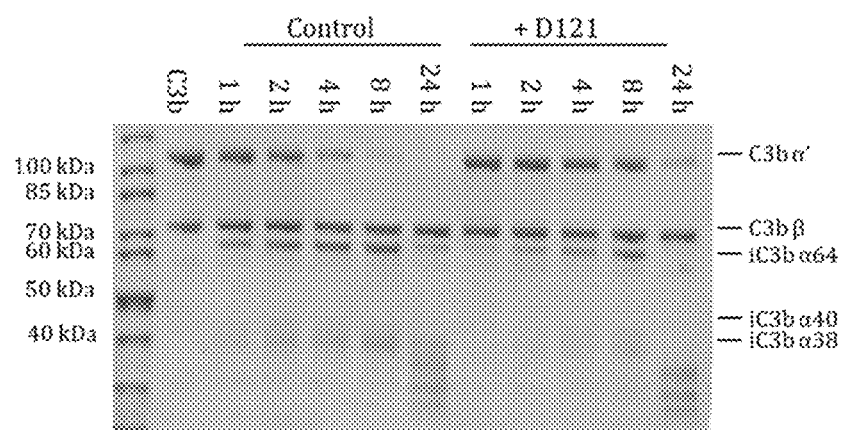
FIG. 25. FI mediate C3b cleavage assay. Cleavage of C3b by FI in the presence or absence of D121. D121 inhibits FI mediated C3b cleavage.
Figure 26:
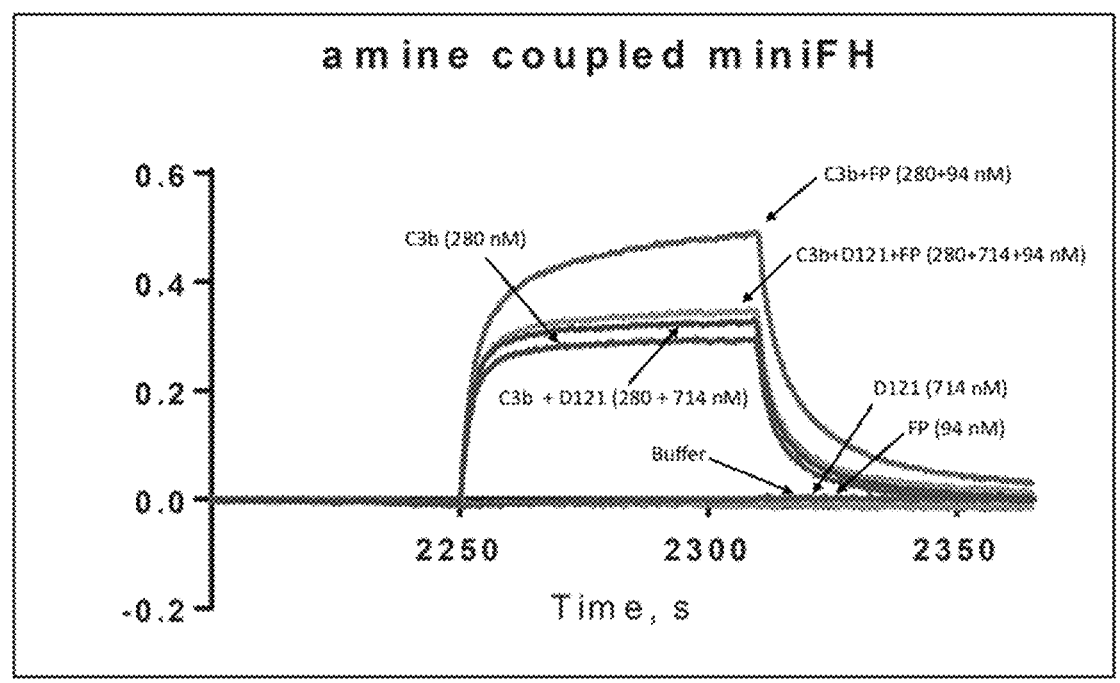
FIG. 26. BLI competition experiment with between D121, mini-FH and FP for binding to C3b. D121 inhibits binding of hFP but not mini-FH to hC3b.

D121 was tested for competition with human properdin (hFP) and human mini-FH for binding to human C3b (hC3b) using BLI. As shown in FIG. 26, D121 inhibits binding of hFP but not mini-FH to hC3b. FIG. 24 shows that D121 does not inhibit the cleavage of C3 into C3b by the CVF-Bb convertase. As shown in FIG. 25, D121 inhibits FI mediated C3b cleavage in the presence of factor H. D121 inhibits the alternative pathway (as assayed by C3d deposition) in a concentration dependent manner (FIG. 23A) but not the classical pathway (FIG. 23B), DI62 do not prevent binding of C3b to FB and assembly of the AP C3 proconvertase C3bFB in SEC as demonstrated in FIG. 4A. FIGS. 4B and 4C shows that DI62 inhibits activation of the AP in a dose dependent manner using human and mouse serum. DI62 also inhibits activation of the LP using human serum as demonstrated in FIG. 4D and activation of the LP using human serum as shown in FIG. 4E.

Figure 27:
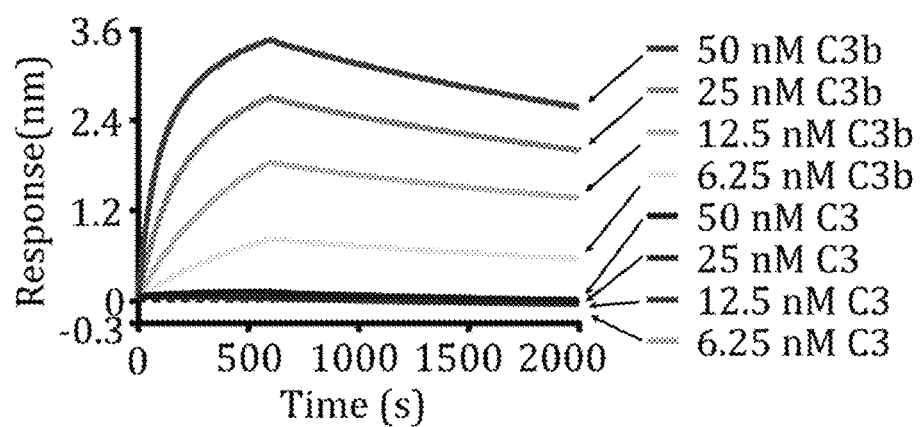
FIG. 27. BLI measurements of the interaction between EWE-hC3nb1, C3 and C3b. EWE-hC3nb1 binds to hC3b but not hC3.

FIG. 5 shows that EWE-hC3bNb1 is specific for C3b as it binds C3b but not C3 in SEC. Binding of EWE-hC3nb1 to hC3b, but not to hC3, was also demonstrated by BLI as shown in FIG. 27. FIG. 6 demonstrates that IgG-Fc-hC3bNb1 is specific for C3b as it binds C3b but not C3 in SEC. EWE-hC3bNb1 and IgG-Fc-hC3bNb1 both inhibits activation of the AP as shown in a C3 deposition assay (FIG. 7A) and in an erythrocyte lysis assay (FIG. 7B).

Figure 28:
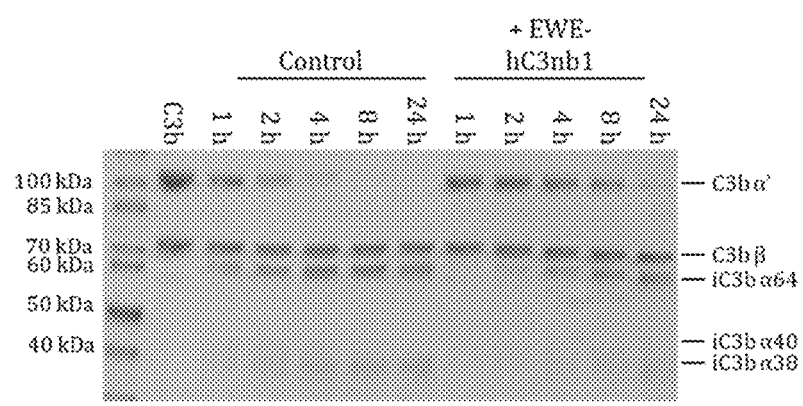
FIG. 28. FI mediate C3b cleavage assay. Cleavage of C3b by FI in the presence or absence of EWE-hC3nb1. EWE-hC3nb1 inhibit FI mediated C3b cleavage.
Figure 29:
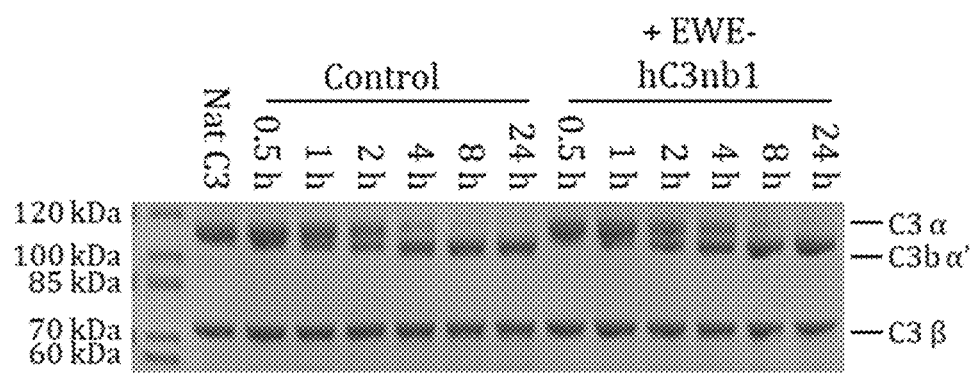
FIG. 29. CVF-Bb mediated cleavage of native C3. Cleavage of C3 into C3b in the presence or absence of EWE-hC3nb1. EWE-hC3nb1 does not inhibit the cleavage of C3 into C3b.

EWE-hC3nb1 was tested for its ability to inhibit cleavage of C3b by factor I (FI) in the presence of factor H (FH) (FIG. 28). As shown in FIG. 28, EWE-hC3nb1 inhibits FI mediated C3b cleavage. EWE-hC3nb1 was tested to assay the inhibitory activity on C3 cleavage by the CVF-Bb convertase (FIG. 29). As shown in FIG. 29, EWE-hC3nb1 does not inhibit the cleavage of C3 into C3b by the CVF-Bb convertase.

Figure 20:
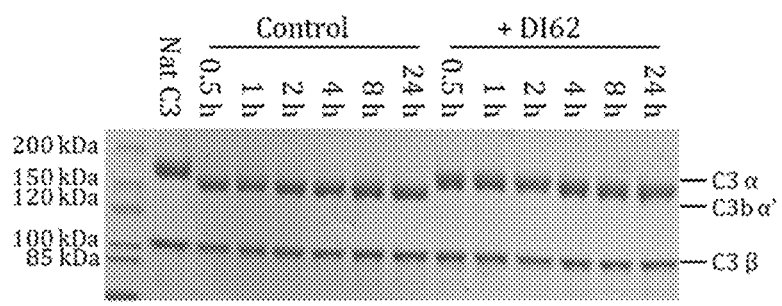
FIG. 20. CVF-Bb cleavage assay. Cleavage of C3 into C3b in the presence or absence of DI62. DI62 inhibits the cleavage of C3 into C3b (generation of C3b alpha' chain) while the C3 is rapidly cleaved in the absence of the nanobody.
Figure 21:
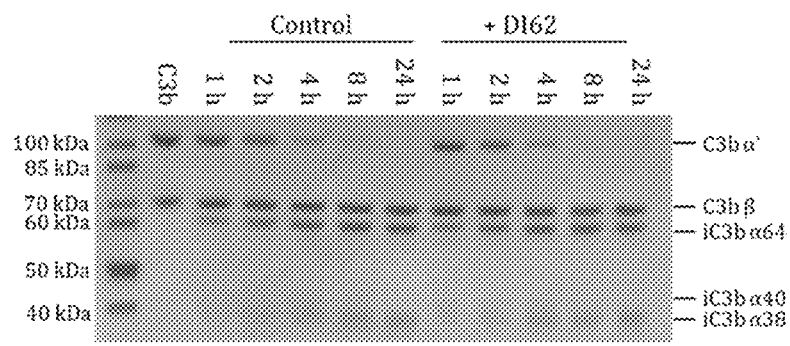
FIG. 21. FI mediate C3b cleavage assay. Cleavage of C3b by FI in the presence or absence of DI62. As shown, DI62 does not inhibit FI mediated C3b cleavage.

FIG. 20 shows that DI62 inhibits the cleavage of C3 into C3b by the CVF-Bb convertase while the C3 is rapidly cleaved in the absence of the nanobody. FIG. 21 shows that DI62 does not inhibit FI mediated C3b cleavage.

Figure 22:
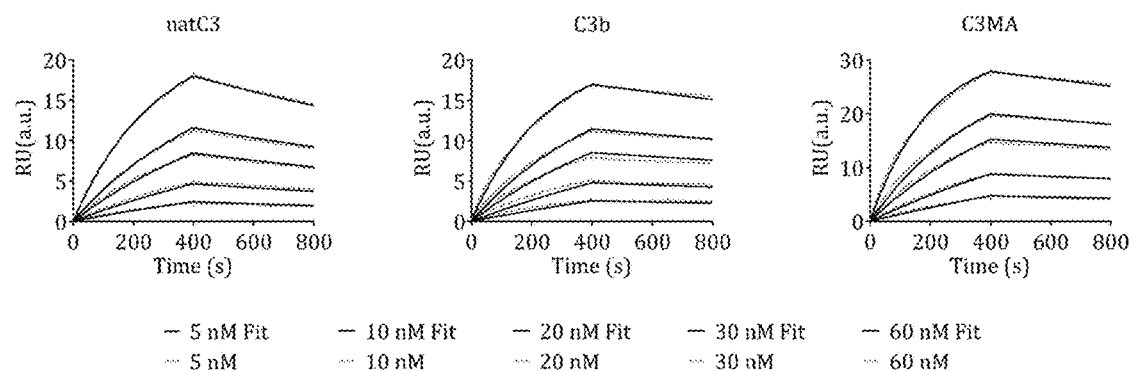
FIG. 22. Surface Plasmon Resonance measurements of the interaction between DI62 and native C3, C3b and C3MA. DI62 binds with high affinity to both native C3, C3b and C3MA.

DI62 binds with high affinity to both native C3, C3b and C3MA as shown in FIG. 22 and table 1.

Example 3

Generation of Inhibitory Nanobodies Specific for C4 and C4b.

Immunization and selection of nanobodies were performed essentially as described by Jensen et al., 2018 but using human C4 and human C4b. Nanobodies were expressed and purified as described in Example 1. C4 was purified from outdated human plasma. 300 mL of plasma were quickly thawed under tap water and 10 mM BZA, 3 µg/mL pancreatic trypsin inhibitor (PTI) and 1 mM PSMF were immediately added while stirring on ice. All the following purification steps were carried out either on ice or at 4° C. 60 mM BaCl2 and 25 mM trisodium citrate were dripped into the plasma while stirring and the precipitate was collected by centrifugation at 6000 rpm for 20 minutes. The supernatant was gaze filtered and loaded on a Q Sepharose FF 200 mL column equilibrated in 10 mM Tris-HCl, 100 mM NaCl, 50 mM EACA (5-amino caproic acid), 5 mM EDTA, 1 mM BZA and 0.5 mM PMSF, pH=7.5. The column was washed until baseline and eluted with a 1200 mL linear gradient from 100 to 600 mM NaCl at 20 mL/min flow rate. The fractions containing C4 were pooled and precipitated by slowly adding 12% w/w PEG6000 while stirring. After precipitation, the precipitate was collected at 4000 g for 30 minutes. The precipitate was resuspended in 100 mL 20 mM Tris-HCl, 200 mM NaCl, 1 mM BZA, 0.5 mM PMSF pH=7.5 (buffer 1A) and the resulting sample was filtered through 0.45 µm filters and applied to a Q Sepharose HP 50 mL column. The column was washed with buffer until baseline and eluted with a 600 mL linear gradient from 200 to 800 mM NaCl at 2 mL/min flow rate, while collecting 4 mL fractions. The fractions containing C4 were pooled and diluted three times with milliQ water. The sample was loaded on a Source15 Q 9 mL column equilibrated in 20 mM Tris-HCl, 200 mM NaCl, 100 µM BZA, 100 µM PMSF, pH=7.5 (buffer 2A). The column was washed until baseline with buffer and eluted with a 100 mL linear gradient from 200 to 400 mM NaCl at 1.5 mL/min flow rate. For C4b generation, C4 was diluted two times in milliQ water and loaded on a 9 mL MonoQ column equilibrated in 50 mM Tris, 200 mM NaCl PH=7.5 (buffer A). The column was washed with buffer A containing 300 mM NaCl and eluted with a 100 mL linear gradient from 300 to 600 mM NaCl at 1.5 mL/min flow rate. The fractions containing C4 were pooled, the concentration was measured and to generate C4b, the sample was supplemented with freshly made 10 mM iodoacetamide (IAA), 50 mM Tris-HCl PH=8.8, 30 mM glycine, followed by incubation with a 0.1% w/w ratio of C1s enzyme (Complement Technologies) for 12 hours at 37° C. To stop the reaction, the sample was added a 1% w/w ratio C1INH:C4 and incubated on ice for 1 hour. The generated C4b was repurified on a Source15 Q 9 mL column equilibrated in 20 mM HEPES, 200 mM NaCl PH=7.5. Elution was performed with an 80 mL linear gradient from 200 to 600 mM NaCl at 1.5 mL/min flow rate.

To crystallize C4b in complex with hC4Nb8, deglycosylated C4b was mixed in a 1:5 w/w ratio with nanobody hC4Nb8. The complex was purified by gel filtration on a Superdex200 increase column (GE Healthcare) equilibrated in 20 mM HEPES-NaOH, 150 mM NaCl, pH=7.5. The fractions containing the complex were concentrated to 8 mg/mL and used to set up crystallization trays where the drops contained 0.15 µL sample and 0.15 µL reservoir. Five days after dispensing the drops, plate crystals of the hC4b: hC4Nb8 complex appeared in 100 mM HEPES-NaOH pH=7, 10% w/w PEG4000, 10% v/v 2-propanol. The crystals were cryoprotected in 20% ethylene glycol for data collection. Datasets with highest resolution shell of 3.5 Å were collected at PETRA III P13 (EMBL Hamburg), at a wavelength of 0.98 Å and at 100 K. The diffraction data were processed using XDS (X-Ray Detector Software, Kabsch (2010)). C4b coordinates (PDB entry: 4XAM) without the C345c domain were used for initial structure determination by molecular replacement in Phenix (Adams, 2010).

pCEP4 plasmid encoding full length wild type C2 was purchased from Genscript and the stabilizing mutations Cys261Ala, Gln263Lys were introduced site using Quick-Change Lightning Site-Directed Mutagenesis Kit (Agilent Technologies) according to supplier's instructions. The DNA was purified using Qiagen Giga prep purification kit. DNA encoding C2 was transfected into HEK293f cells using a DNA: PEI (polyethyleneimine) ratio of 1:3. The conditioned medium was harvested 5 days after transfection and the pH was adjusted to 6.2 using 1 M NaOAc stock solution. The supernatant was supplemented with 0.5 mM PMSF, 1 mM BZA and 0.09% NaN3 and vacuum filtered through a 0.22 µm cellulose filter membrane prior to loading on an SP Sepharose FF 13 mL column, equilibrated in 50 mM NaOAc pH=6.2 (buffer A). All the purification steps were carried out at 4° C. The column was washed until baseline with buffer A and elution was performed with 100 mL linear gradient from 0 to 600 mM NaCl. The fractions containing C2 were concentrated and further purified by gel filtration on a Superdex 200 increase column (GE Healthcare) equilibrated in 20 mM HEPES, 150 mM NaCl PH=7.5. TRIFMA assay for CP was performed as described in Example 1.

To assay proconvertase formation in the presence of nanobodies, each nanobody was incubated with the proconvertase for 5 minutes at 4° C. at a C2:C4b:Nb 1.3:1:6 molar ratio and the sample was injected on a Superdex200 increase column (GE Healthcare) equilibrated in 20 mM HEPES-NaOH, 150 mM NaCl, 2 mM MgCl2 pH=7.5. Disruption of proconvertase formation was monitored by an increased OD (280 nm) intensity of the C4b (11.5 mL) and C2 (13 mL) peaks on the chromatograms.

Surface plasmon resonance measurements were conducted using a BIAcore T200 instrument (GE Healthcare). Streptavidin was diluted to 10 µg/mL in 10 mM sodium acetate pH=4.5 and immobilized to 100 RU on the carboxymethylated dextran surface of a CM5 sensor chip (GE Healthcare) using an amine coupling kit. The biotinylated nanobody was injected on the immobilized streptavidin at 30 µg/mL, giving 13 RU of captured nanobody. The binding measurements were performed in 20 mM HEPES, 150 mM NaCl, 3 mM MgCl2, 0.05% Tween 20 pH=7.5 at 30 µL/min flow rate. At the end of each concentration measurement the surface was regen-erated by injection of 100 mM glycine pH=2.7 for three cycles of 10 s contact time. Sensograms were recorded at concentrations 0.1, 5, 10, 25, 50 and 100 nM for C4, while at 0.1, 1, 5, 10, 25 nM for C4b. Fitting of the data was performed for all the measured concentrations simultaneously, using BIAevaluation software (GE Healthcare). The apparent equilibrium dissociation constants (KD) were calculated from the ratio between the association and dissociation constants. The presented data are the mean±S.E. from two (C4b) or three (C4) separate experiments.

Figure 10A:
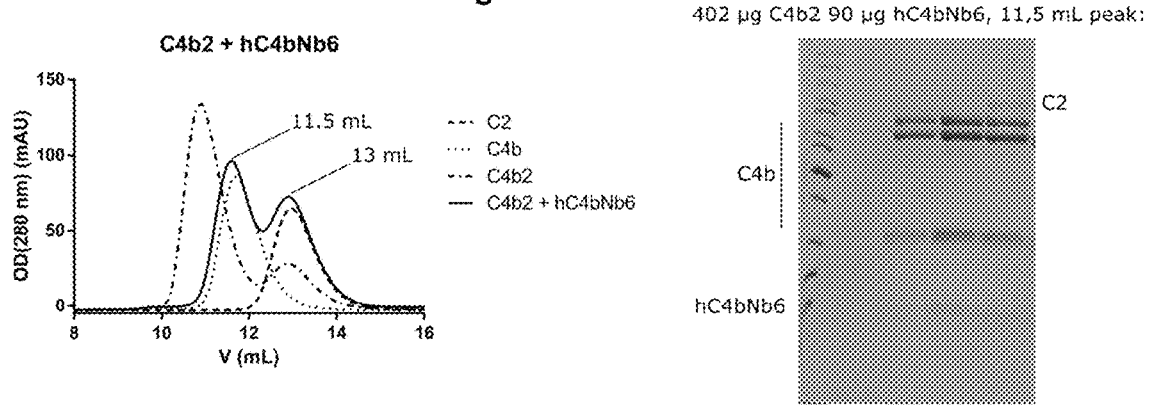
FIGS. 10A-10B.
Figure 10B:
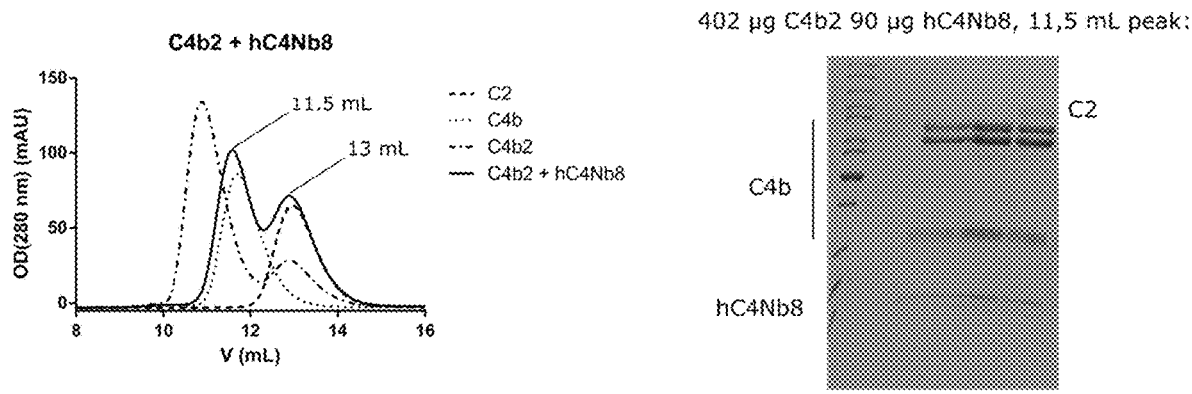
Figure 11A:
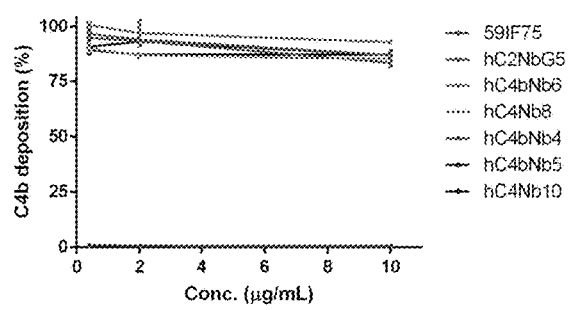
FIGS. 11A-11B.
Figure 11B:
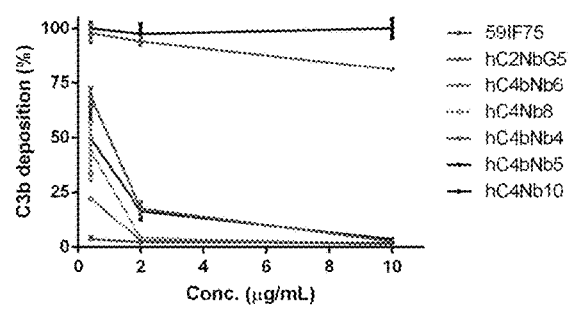

As demonstrated in FIGS. 8A and 8B hC4bNb6 binds to C4b and C4 in SEC. FIGS. 8C-8E shows that hC4bNb6 binds to C4 and C4b with high affinity as measured by SPR. FIG. 9 demonstrates that hC4Nb8 binds to C4b and C4 in SEC. hC4bNb6 and hC4Nb8 prevents formation of the CP C3 proconvertase C4b2 as evident from FIG. 10. hC4bNb6, hC4Nb8, hC4Nb4, hC4Nb5 and hC4Nb10 do not inhibit C4b deposition in a CP activation assay (FIG. 11A) but do inhibit C3b deposition in a dose dependent manner in a CP activation assay (FIG. 11B).

Figure 30:
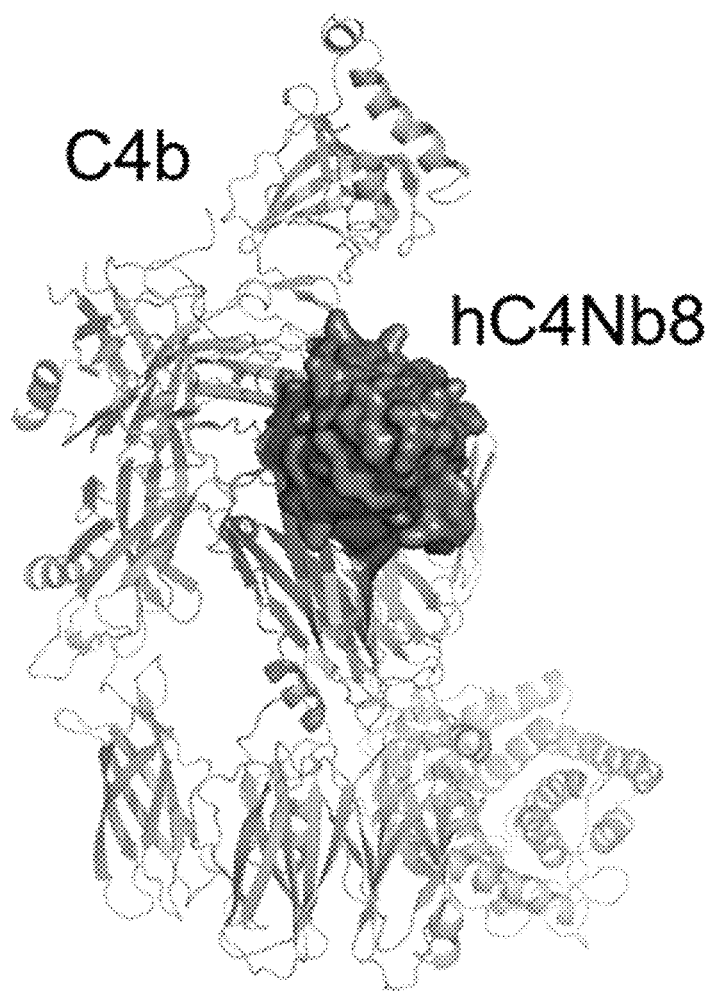
FIG. 30. Structure of human C4b in complex with hC4nb8. C4b is shown in cartoon representation and hC4bNb8 in surface representation. hC4bNb8 interacts with the MG6 domain and the 'NT region of C4b.
Figure 31:
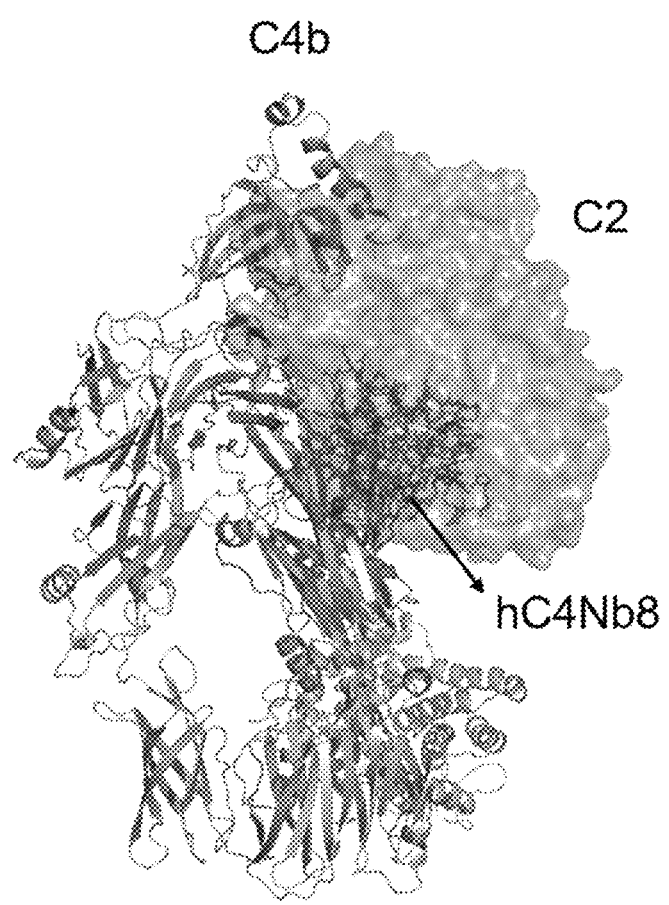
FIG. 31. Superposition of the structure of C4b-hC4nb8 and a model of C4bC2. C4b is shown in cartoon, C2 in surface and line representations. The structure shows that hC4nb8 and C2 cannot bind to C4b simultaneously and thus explains how hC4nb8 prevents assembly of the classical pathway C3 and C5 pro-convertases.

FIG. 30 shows the crystal structure of hC4nb8 in complex with hC4b. hC4bNb8 interacts with the MG6 domain and the α'NT region of C4b. FIG. 31 shows a superposition of the structure of C4b-hC4nb8 and a model of C4bC2. As evident from the figure hC4nb8 clashes C2 and thus inhibit assembly of the classical pathway C3 and C5 pro-convertases.

Figure 14:
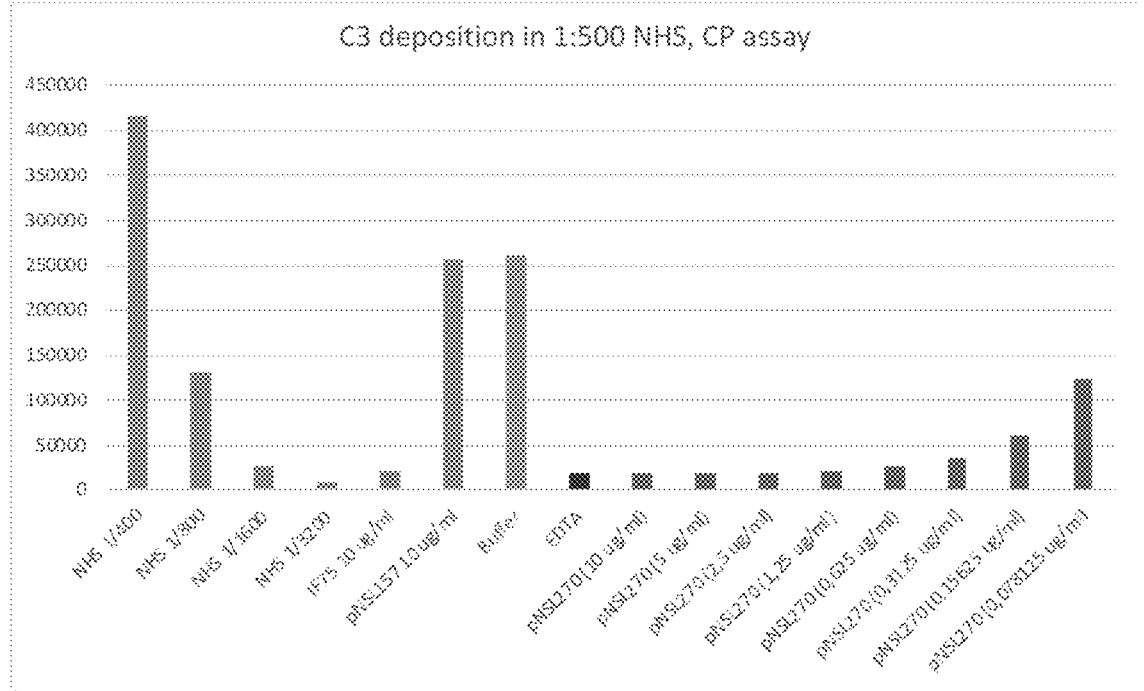
FIG. 14. Inhibitory action of pNSL270 on deposition of C3b in a CP activation assay on a surface of deposited IgG. IF75 is C1q inhibitor described above and pNSL157 is a control nanobody. As shown pNSL270 inhibits C3 deposition, and thus C3 cleavage, in a dose dependent manner upon activation of the classical pathway.
Figure 15:
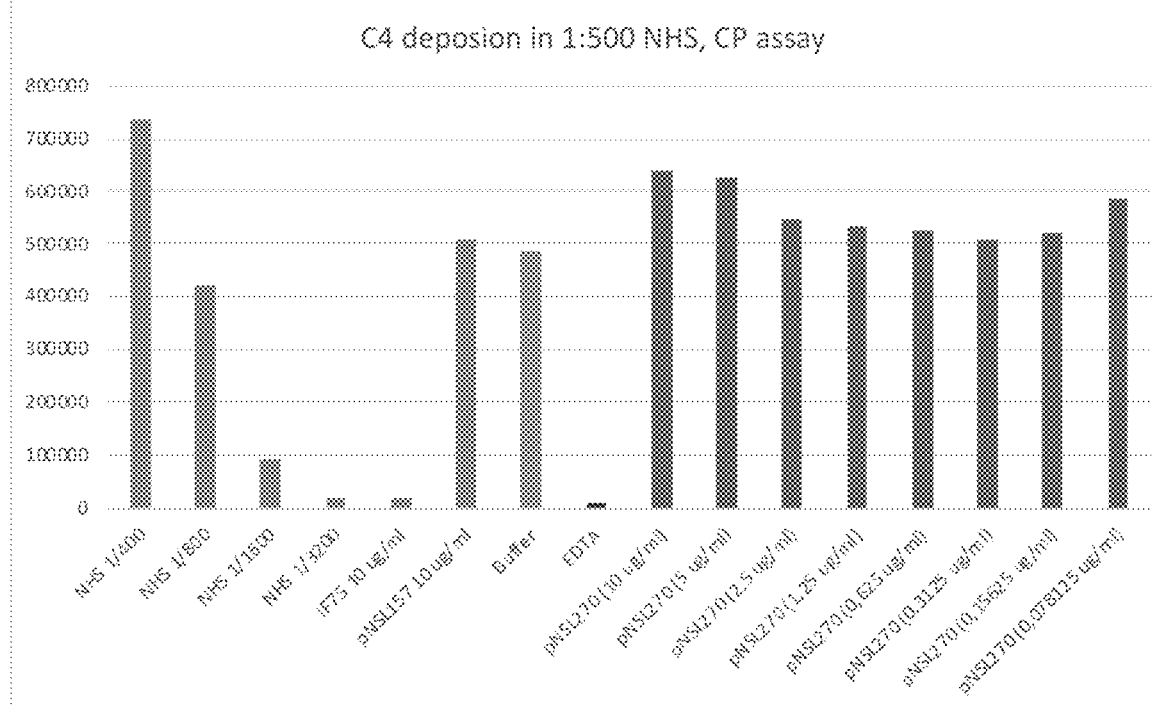
FIG. 15. Inhibitory action of pNSL270 on deposition of C4b in a CP activation assay on a surface of deposited IgG. IF75 is C1q inhibitor described above and pNSL157 is a control nanobody. As shown pNSL270 does not inhibit C4b deposition and thus C4 cleavage.
Figure 16:
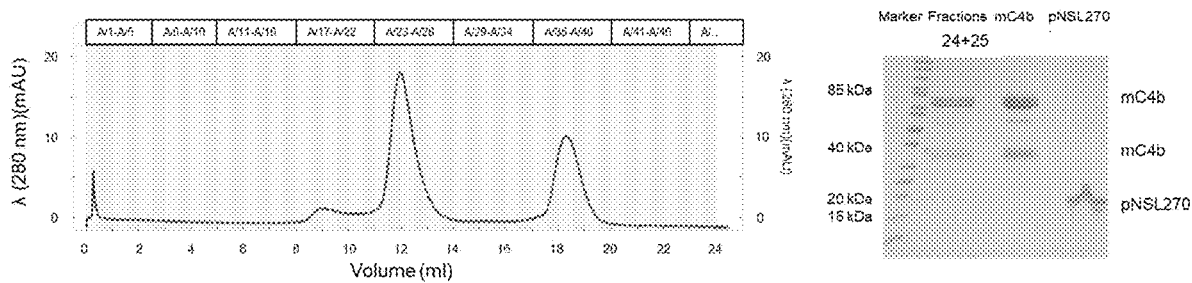
FIG. 16. SEC of the complex between mouse C4b (mC4b) and pNSL270 on a Superdex 200 Increase 10/300 column (left). SDS-PAGE of peak fractions 24+25 from run and pure mC4b and pNSL270 (right). As shown in the SDS-PAGE, pNSL270 binds to mouse C4b.

FIGS. 14 and 15 show classical pathway C3 and C4 deposition assays with normal human serum. As shown, pNSL270 inhibits C3 deposition (FIG. 14) in a dose dependent manner in a classical pathway assay but not C4 deposition (FIG. 15). Thus, pNSL270 prevents human C3 cleavage but not human C4 cleavage upon activation of the classical pathway. As demonstrated in FIG. 16 pNSL270 binds to mouse C4b in SEC.

Example 4

Bispecific C1q Nanobodies Activates Complement on Cancer Cells.

The genes for nanobodies 7D12, 9G8 and MU1053 were purchased from Genscript. For generation of bispecific nanobodies 7D12, 9G8 and MU1053 were genetically fused to C1q nanobodies using a 10 amino acid linker (GGGGSGGGGS) and expressed and purified as described above, Constructs are shown in FIG. 12A. A431, MDA-MB-468 and Raji cells were cultured in RPMI at 37° C. with 8% CO2. A1207 cells were cultured in DMEM at 37° C. with 8% CO2. All cells were supplemented with 10% fetal bovine serum and 0.1 mg/ml Penicillin-Streptomycin. Cells were detached by incubation with Accutase® (Sigma Aldrich) for 10 min at 37° C. Cells were harvested, washed 2 times in PBS and resuspended in veronal buffer saline (VBS). 1.0-0.5×10⁶ cells were incubated with or without Nbs and 10% NHS (final concentration) for 1 h at 37° C. Following cells were centrifuged at 300 g for 5 min and washed 2 times in 800 µl PBA (PBS containing 1% w/v BSA). Cells were resuspended in 100 µl PBA added 100 µl mouse anti C3c (diluted 1:100) or mouse anti C1q (diluted 1:100) and incubated for 1 h on ice. Cells were centrifuged and washed two times in 800 µl PBA, added 100 µl anti mouse-FITC (diluted 1:100) and incubated for 1 h on ice. Cells were centrifuged and washed two times in 800 µl PBA and resuspended in 200 µl PBA. Ten minutes prior to flow cytometry cells were added DAPI. Flow cytometry was performed using a NovoCyte flow cytometer. Cells used for analysis were gated as single cells and live cells. Data were analyzed with FCS express.

Incubation of BiCE161 (anti-C1q fused to anti-CD38) with 10% human serum and Raji cells, which expresses CD38, results in recruitment of C1q (FIG. 12B, left) and complement activation as shown by deposition of C3 on cells (FIG. 12B, right).

Addition of DH38 and DH38 to MDA-MB-468 cells expressing EGFR results in little C3 deposition when incubated with 10% human serum. Addition of IA74 results in a medium amount of deposited C3, while addition of DF85 results in a high amount of C3 deposition (FIG. 12C).

Figure 13A:
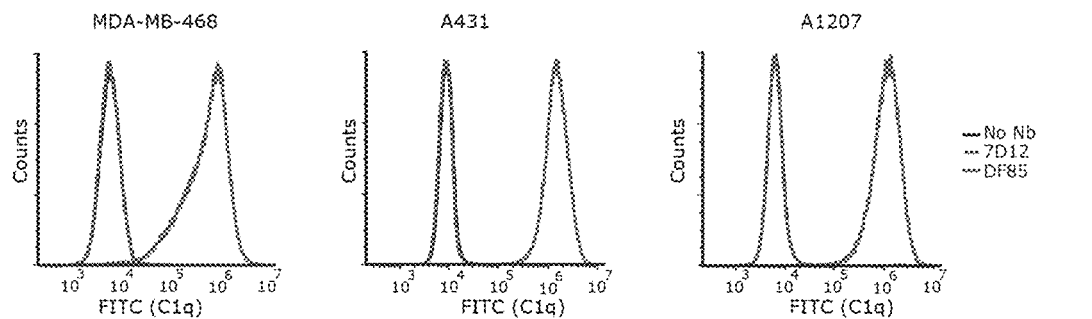
Figure 13B:
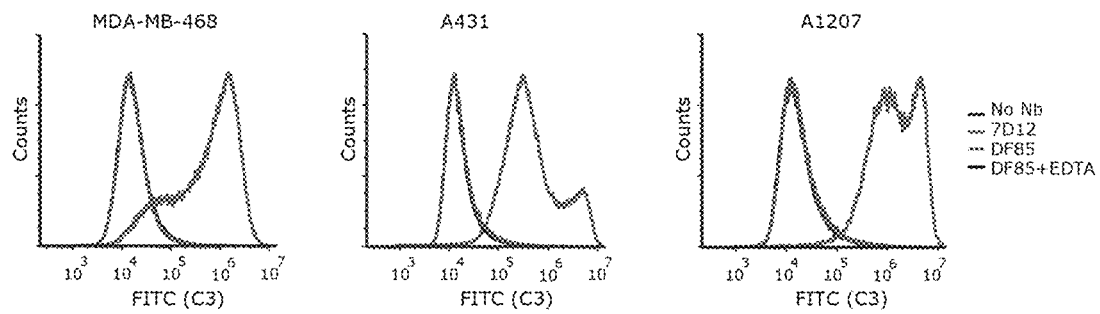
Figure 13C:
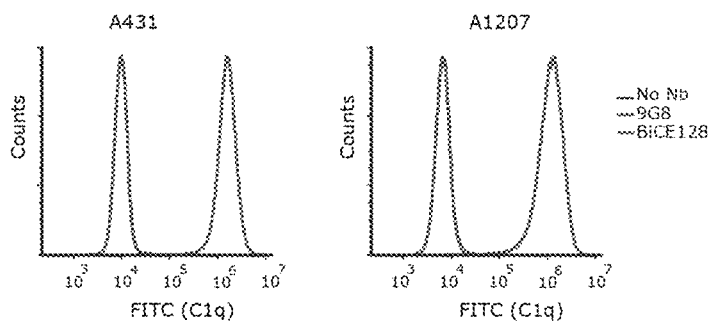
Figure 13D:
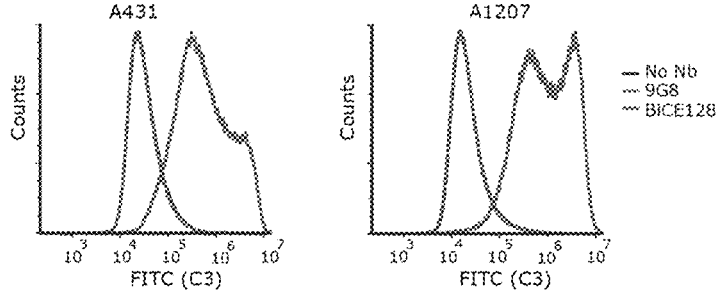

DF85 is able to recruit C1q from human serum to different tumor cell lines that expresses EGFR (FIG. 13A). C1q recruitment results in complement activation and C3 deposition on cells (FIG. 13B). Incubation with BiCE128 results in similar C1q recruitment and C3 deposition as incubation with DF85 (FIGS. 13C and 13D).

REFERENCES

Afonine P V, Grosse-Kunstleve R W, Echols N, Headd J J, Moriarty N W, Mustyakimov M, Terwilliger T C, Urzhumtsev A, Zwart P H, Adams P D. Towards automated crystallographic structure refinement with phenix.refine. Acta Crystallogr D Biol Crystallogr. 2012 April; 68 (Pt 4): 352-67.

Emsley P, Lohkamp B, Scott W G, Cowtan K. Features and development of Coot. Acta Crystallogr D Biol Crystallogr. 2010 April; 66 (Pt 4): 486-501.

Jensen R K, Pihl R, Gadeberg T A F, Jensen J K, Andersen K R, Thiel S, Laursen N S, Andersen G R. A potent complement factor C3-specific nanobody inhibiting multiple functions in the alternative pathway of human and murine complement. J Biol Chem. 2018 Apr. 27; 293 (17): 6269-6281.

Kabsch, W. (2010) Integration, scaling, space-group assignment and post-refinement. Acta Crystallogr. D Biol. Crystallogr. 66, 133-144.

McCoy A J, Grosse-Kunstleve R W, Adams P D, Winn M D, Storoni L C, Read R J. Phaser crystallographic software. J Appl Crystallogr. 2007 Aug. 1; 40 (Pt 4): 658-674. Epub 2007 Jul. 13.

Moreau C, Bally I, Chouquet A, Bottazzi B, Ghebrehiwet B, Gaboriaud C, Thielens N. Structural and Functional Characterization of a Single-Chain Form of the Recognition Domain of Complement Protein C1q. Front Immunol. 2016 Mar. 2; 7:79. doi: 10.3389/fimmu.2016.00079.

Scheres S H. RELION: implementation of a Bayesian approach to cryo-EM structure determination. J Struct Biol. 2012 December; 180 (3): 519-30

Suloway, C., Pulokas, J., Fellmann, D., Cheng, A., Guerra, F., Quispe, J., Stagg, S., Potter, C. S., and Carragher, B. (2005) Automated molecular microscopy: the new Leginon system. J. Struct. Biol. 151, 41-60.

Tenner A J, Lesavre P H, Cooper N R. Purification and radiolabeling of human C1q. J Immunol. 1981 August; 127 (2): 648-53.

Voss, N. R., Yoshioka, C. K., Radermacher, M., Potter, C. S., and Carragher, B. (2009) DoG Picker and TiltPicker: software tools to facilitate particle selection in single particle electron microscopy. J. Struct. Biol. 166, 205-213.

Sequences

Where relevant, the UniProt reference is provided for specific reference to the respective sequences. It is understood that the present disclosure relates to all variants disclosed in relation to the specific UniProt reference.

```
Human C3 UniProtKB - P01024 (CO3_HUMAN) residues 23-1663
                                                    SEQ ID NO: 1
SPMYSIITPNILRLESEETMVLEAHDAQGDVPVTVTVHDFPGKKLVLSSEKTVLTPATN
HMGNVTFTIPANREFKSEKGRNKFVTVQATFGTQVVEKVVLVSLQSGYLFIQTDKTIYT
PGSTVLYRIFTVNHKLLPVGRTVMVNIENPEGIPVKQDSLSSQNQLGVLPLSWDIPELV
NMGQWKIRAYYENSPQQVFSTEFEVKEYVLPSFEVIVEPTEKFYYIYNEKGLEVTITAR
FLYGKKVEGTAFVIFGIQDGEQRISLPESLKRIPIEDGSGEVVLSRKVLLDGVQNPRAE
DLVGKSLYVSATVILHSGSDMVQAERSGIPIVTSPYQIHFTKTPKYFKPGMPFDLMVFV
TNPDGSPAYRVPVAVQGEDTVQSLTQGDGVAKLSINTHPSQKPLSITVRTKKQELSEA
EQATRTMQALPYSTVGNSNNYLHLSVLRTELRPGETLNVNFLLRMDRAHEAKIRYYTY
LIMNKGRLLKAGRQVREPGQDLVVLPLSITTDFIPSFRLVAYYTLIGASGQREVVADSV
WVDVKDSCVGSLVVKSGQSEDRQPVPGQQMTLKIEGDHGARVVLVAVDKGVFVLNK
KNKLTQSKIWDVVEKADIGCTPGSGKDYAGVFSDAGLTFTSSSGQQTAQRAELQCPQ
PAARRRRSVQLTEKRMDKVGKYPKELRKCCEDGMRENPMRFSCQRRTRFISLGEAC
KKVFLDCCNYITELRRQHARASHLGLARSNLDEDIIAEEENIVSRSEFPESWLWNVEDLK
EPPKNGISTKLMNIFLKDSITTWEILAVSMSDKKGICVADPFEVTVMQDFFIDLRLPYSV
VRNEQVEIRAVLYNYRQNQELKVRVELLHNPAFCSLATTKRRHQQTVTIPPKSSLSVP
YVIVPLKTGLQEVEVKAAVYHHFISDGVRKSLKVVPEGIRMNKTVAVRTLDPERLGRE
GVQKEDIPPADLSDQVPDTESETRILLQGTPVAQMTEDAVDAERLKHLIVTPSGCGEQ
NMIGMTPTVIAVHYLDETEQWEKFGLEKRQGALELIKKGYTQQLAFRQPSSAFAAFVK
RAPSTWLTAYVVKVFSLAVNLIAIDSQVLCGAVKWLILEKQKPDGVFQEDAPVIHQEMI
GGLRNNNEKDMALTAFVLISLQEAKDICEEQVNSLPGSITKAGDFLEANYMNLQRSYT
VAIAGYALAQMGRLKGPLLNKFLTTAKDKNRWEDPGKQLYNVEATSYALLALLQLKDF
DFVPPVVRWLNEQRYYGGGYGSTQATFMVFQALAQYQKDAPDHQELNLDVSLQLPS
RSSKITHRIHWESASLLRSEETKENEGFTVTAEGKGQGTLSVVTMYHAKAKDQLTCN
KFDLKVTIKPAPETEKRPQDAKNTMILEICTRYRGDQDATMSILDISMMTGFAPDTDDL
KQLANGVDRYISKYELDKAFSDRNTLIIYLDKVSHSEDDCLAFKVHQYFNVELIQPGAV
KVYAYYNLEESCTRFYHPEKEDGKLNKLCRDELCRCAEENCFIQKSDDKVTLEERLDK
ACEPGVDYVYKTRLVKVQLSNDFDEYIMAIEQTIKSGSDEVQVGQQRTFISPIKCREAL
KLEEKKHYLMWGLSSDFWGEKPNLSYIIGKDTWVEHWPEEDECQDEENQKQCQDL
GAFTESMVVFGCPN Mouse C3 UniProtKB - P01027 (CO3_MOUSE) residues 25-1663
                                                    SEQ ID NO: 2
IPMYSIITPNVLRLESEETIVLEAHDAQGDIPVTVTVQDFLKRQVLTSEKTVLTGASGHL
RSVSIKIPASKEFNSDKEGHKYVTVVANFGETVVEKAVMVSFQSGYLFIQTDKTIYTPG
STVLYRIFTVDNNLLPVGKTVVILIETPDGIPVKRDILSSNNQHGILPLSWNIPELVNMGQ
WKIRAFYEHAPKQIFSAEFEVKEYVLPSFEVRVEPTETFYYIDDPNGLEVSIIAKFLYGK
NVDGTAFVIFGVQDGDKKISLAHSLTRVVIEDGVGDAVLTRKVLMEGVRPSNADALVG
KSLYVSVTVILHSGSDMVEAERSGIPIVTSPYQIHFTKTPKFFKPAMPFDLMVFVTNPD
GSPASKVLVVTQGSNAKALTQDDGVAKLSINTPNSRQPLTITVRTKKDTLPESRQATK
TMEAHPYSTMHNSNNYLHLSVSRMELKPGDNLNVNFHLRTDPGHEAKIRYYTYLVMN
KGKLLKAGRQVREPGQDLVVLSLPITPEFIPSFRLVAYYTLIGASGQREVVADSVWVD
VKDSCIGTLVVKGDPRDNHLAPGQQTTLRIEGNQGARVGLVAVDKGVFVLNKKNKLT
QSKIWDVVEKADIGCTPGSGKNYAGVFMDAGLAFKTSQGLQTEQRADLECTKPAASV
QLMERRRMDKAGQYTDKGLRKCCEDGMRDIPMRYSCQRRARLITQGENCIKAFIDCC
NHITKLREQHRRDHVLGLARSELEEDIIPEEDIISRSHFPQSWLWTIEELKEPEKNGIST
KVMNIFLKDSITTWEILAVSLSDKKGICVADPYEIRVMQDFFIDLRLPYSVVRNEQVEIR
AVLFNYREQEELKVRVELLHNPAFCSMATAKNRYFQTIKIPPKSSVAVPYVIVPLKIGQ
QEVEVKAAVFNHFISDGVKKTLKVVPEGMRINKTVAIHTLDPEKLGQGGVQKVDVPAA
```

-continued

```
DLSDQVPDTDSETRIILQGSPVVQMAEDAVDGERLKHLIVTPAGCGEQNMIGMTPTVI
AVHYLDQTEQWEKFGIEKRQEALELIKKGYTQQLAFKQPSSAYAAFNNRPPSTWLTA
YVVKVFSLAANLIAIDSHVLCGAVKWLILEKQKPDGVFQEDGPVIHQEMIGGFRNAKEA
DVSLTAFVLIALQEARDICEGQVNSLPGSINKAGEYIEASYMNLQRPYTVAIAGYALAL
MNKLEEPYLGKFLNTAKDRNRWEEPDQQLYNVEATSYALLALLLLKDFDSVPPVVRW
LNEQRYYGGGYGSTQATFMVFQALAQYQTDVPDHKDLNMDVSFHLPSRSSATTFRL
LWENGNLLRSEETKQNEAFSLTAKGKGRGTLSVVAVYHAKLKSKVTCKKFDLRVSIRP
APETAKKPEEAKNTMFLEICTKYLGDVDATMSILDISMMTGFAPDTKDLELLASGVDRY
ISKYEMNKAFSNKNTLIIYLEKISHTEEDCLTFKVHQYFNVGLIQPGSVKVYSYYNLEES
CTRFYHPEKDDGMLSKLCHSEMCRCAEENCFMQQSQEKINLNVRLDKACEPGVDYV
YKTELTNIELLDDFDEYTMTIQQVIKSGSDEVQAGQQRKFISHIKCRNALKLQKGKKYL
MWGLSSDLWGEKPNTSYIIGKDTWVEHWPEAEECQDQKYQKCEELGAFTESMVV
YGCPN

Human C1q chain A UniProtKB - P02745 (C1QA_HUMAN) residues 23-245
                                                      SEQ ID NO: 3
EDLCRAPDGKKGEAGRPGRRGRPGLKGEQGEPGAPGIRTGIQGLKGDQGEPGPSG
NPGKVGYPGPSGPLGARGIPGIKGTKGSPGNIKDQPRPAFSAIRRNPPMGGNVVIFDT
VITNQEEPYQNHSGRFVCTVPGYYYFTFQVLSQWEICLSIVSSSRGQVRRSLGFCDTT
NKGLFQVVSGGMVLQLQQGDQVWVEKDPKKGHIYQGSEADSVFSGFLIFPSA Human C1q chain B UniProtKB - P02746 (C1QB_HUMAN) residues 28-253
                                                      SEQ ID NO: 4
QLSCTGPPAIPGIPGIPGTPGPDGQPGTPGIKGEKGLPGLAGDHGEFGEKGDPGIPGN
PGKVGPKGPMGPKGGPGAPGAPGPKGESGDYKATQKIAFSATRTINVPLRRDQTIRF
DHVITNMNNNYEPRSGKFTCKVPGLYYFTYHASSRGNLCVNLMRGRERAQKVVTFC
DYAYNTFQVTTGGMVLKLEQGENVFLQATDKNSLLGMEGANSIFSGFLLFPDMEA Human C1q chain C UniProtKB - P02747 (C1QC_HUMAN) residues 29-245
                                                      SEQ ID NO: 5
NTGCYGIPGMPGLPGAPGKDGYDGLPGPKGEPGIPAIPGIRGPKGQKGEPGLPGHP
GKNGPMGPPGMPGVPGPMGIPGEPGEEGRYKQKFQSVFTVTRQTHQPPAPNSLIRF
NAVLTNPQGDYDTSTGKFTCKVPGLYYFVYHASHTANLCVLLYRSGVKVVTFCGHTS
KTNQVNSGGVLLRLQVGEEVWLAVNDYYDMVGIQGSDSVFSGFLLFPD Human C4A alpha chain UniProtKB - P0C0L4 (CO4_HUMAN) residues 680-1446
                                                      SEQ ID NO: 6
NVNFQKAINEKLGQYASPTAKRCCQDGVTRLPMMRSCEQRAARVQQPDCREPFLSC
CQFAESLRKKSRDKGQAGLQRALEILQEEDLIDEDDIPVRSFFPENWLWRVETVDRF
QILTLWLPDSLTTWEIHGLSLSKTKGLCVATPVQLRVFREPHLHLRLPMSVRRFEQLEL
RPVLYNYLDKNLTVSVHVSPVEGLCLAGGGGLAQQVLVPAGSARPVAFSVVPTAAAA
VSLKVVARGSFEFPVGDAVSKVLQIEKEGAIHREELVYELNPLDHRGRTLEIPGNSDP
NMIPDGDFNSYVRVTASDPLDTLSEGALSPGGVASLLRLPRGCGEQTMIYLAPTLAA
SRYLDKTEQWSTLPPETKDHAVDLIQKGYMRIQQFRKADGSYAAWLSRDSSTWLTAF
VLKVLSLAQEQVGGSPEKLQETSNWLLSQQQADGSFQDPCPVLDRSMQGGLVGND
ETVALTAFVTIALHHGLAVFQDEGAEPLKQRVEASISKANSFLGEKASAGLLGAHAAAI
TAYALTLTKAPVDLLGVAHNNLMAMAQETGDNLYWGSVTGSQSNAVSPTPAPRNPS
DPMPQAPALWIETTAYALLHLLLHEGKAEMADQASAWLTRQGSFQGGFRSTQDTVIA
LDALSAYWIASHTTEERGLNVTLSSTGRNGFKSHALQLNNRQIRGLEEELQFSLGSKI
NVKVGGNSKGTLKVLRTYNVLDMKNTTCQDLQIEVTVKGHVEYTMEANEDYEDYEYD
ELPAKDDPDAPLQPVTPLQLFEG Human C4A beta chain UniProtKB - P0C0L4 (CO4_HUMAN) residues 20-675
                                                      SEQ ID NO: 7
KPRLLLFSPSVVHLGVPLSVGVQLQDVPRGQVVKGSVFLRNPSRNNVPCSPKVDFTL
SSERDFALLSLQVPLKDAKSCGLHQLLRGPEVQLAHSPWLKDSLSRTTNIQGINLLF
SSRRGHLFLQTDQPIYNPGQRVRYRVFALDQKMRPSTDTITVMVENSHGLRVRKKEV
YMPSSIFQDDFVIPDISEPGTWKISARFSDGLESNSSTQFEVKKYVLPNFEVKITPGKP
YILTVPGHLDEMQLDIQARYIYGKPVQGVAYRFGLLDEDGKKTFFRGLESQTKLVNG
QSHISLSKAEFQDALEKLNMGITDLQGLRLYVAAAIIESPGGEMEEAELTSWYFVSSPF
SLDLSKTKRHLVPGAPPLLQALVREMSGSPASGIPVKVSATVSSPGSVPEVQDIQQNT
DGSGQVSIPIIIPQTISELQLSVSAGSPHPAIARLTVAAPPSGGPGFLSIERPDSRPPRV
GDTLNLNLRAVGSGATFSHYYYMILSRGQIVFMNREPKRTLTSVSVFVDHHLAPSFYF
VAFYYHGDHPVANSLRVDVQAGACEGKLELSVDGAKQYRNGESVKLHLETDSLALVA
LGALDTALYAAGSKSHKPLNMGKVFEAMNSYDLGCGPGGGDSALQVFQAAGLAFSD
GDQWTLSRKRLSCPKEKTT Human C4a gamma chain UniProtKB - P0C0L4 (CO4_HUMAN) residues 1454-
1744
                                                      SEQ ID NO: 8
EAPKVVEEQESRVHYTVCIWRNGKVGLSGMAIADVTLLSGFHALRADLEKLTSLSDRY
VSHFETEGPHVLLYFDSVPTSRECVGFEAVQEVPVGLVQPASATLYDYYNPERRCSV
FYGAPSKSRLLATLCSAEVCQCAEGKCPRQRRALERGLQDEDGYRMKFACYYPRVE
YGFQVKVLREDSRAAFRLFETKITQVLHFTKDVKAAANQMRNFLVRASCRLRLEPGKE
YLIMGLDGATYDLEGHPQYLLDSNSWIEEMPSERLCRSTRQRAACAQLNDFLQEYGT
QGCQV
```

-continued

EA57

QVQLVESGGGLVQPGGSLRLSCAASGFTLNQYAIGWFRQAPGKEREGVSCISNSDG
GLYYADSVKGRFTISRDNAKNTVYLQMNSLKPEDTAVYYCATDPGGPTMYGSRWCD
SRLFYSWGQGTQVTVSS
SEQ ID NO: 9

CDR1:

GFTLNQYAIG
SEQ ID NO: 10

CDR2:

CISNSDGGLY
SEQ ID NO: 11

CDR3:

DPGGPTMYGSRWCDSRLFYS
SEQ ID NO: 12

IF75

QVQLVETGGGLVQAGGSLRLSCAASGRTFNNDVMAWFRQAPGTEREFVALITAGGG
THYADSVKGRFVISRDNDKNMAYLQMNSLKSEDTAIYYCGADENPPGWPSRWSSAY
DYWGQGTQVTVSS
SEQ ID NO: 13

CDR1:

GRTFNNDVMA
SEQ ID NO: 14

CDR2:

LITAGGGTH
SEQ ID NO: 15

CDR3:

DENPPGWPSRWSSAYDY
SEQ ID NO: 16

IF78

QVQLVESGGGLVQDGDSLRLSCAGSGWTFRDSMYNMGWFRQAPGKEREFVAAISW
RGGSTLYADSVKGRFTISRDNAKNTVYLQMNSLKPEDTAVYQCAADTSARAALYSTG
YEYDHWGQGTQVTVSS
SEQ ID NO: 17

CDR1:

GWTFRDSMYNMG
SEQ ID NO: 18

CDR2:

AISWRGGSTLY
SEQ ID NO: 19

CDR3:

DTSARAALYSTGYEYDH
SEQ ID NO: 20

IH31

QVQLVESGGGLVQAGGSLRLSCAASGRTSSDHITAWFRQAPGKEREFVASINWSGS
RAYYADSDKRRFTISRDNAKNTVSLQTNSLKPEDTAVYYCAVKFADISDAYYHHQTDY
DYWGQGTQVTVSS
SEQ ID NO: 21

CDR1:

GRTSSDHITA
SEQ ID NO: 22

CDR2:

SINWSGSRAY
SEQ ID NO: 23

CDR3:

KFADISDAYYHHQTDYDY
SEQ ID NO: 24

IH33

QVQLVETGGGLVQTGGSLRLSCAASGSTDSIAAIIWYRQTPENEREFVAGITSGVNTN
YAAPVKGRFTISRDNAKNTVYLQMNSLKPEDTGVYYCKAAVVMGPSTTDYWGQGTQ
VTVSS
SEQ ID NO: 25

-continued

```
CDR1:                                                        SEQ ID NO: 26
GSTDSIAAII

CDR2:                                                        SEQ ID NO: 27
GITSGVN

CDR3:                                                        SEQ ID NO: 28
AVVMGPSTTDY

IH35                                                         SEQ ID NO: 29
QVQLVETGGGVAQAGGSLRLSCAASGFSFDDYAIGWLRQAPGKEREGVSCISAGDG
SPQYADSVKGRFTISSDNAKNTVYLQMNSLKPEDTAVYYCAVSRWSNCAWDYYGMD
PWGKGTLVTVSS

CDR1:                                                        SEQ ID NO: 30
GFSFDDYAIG

CDR2:                                                        SEQ ID NO: 31
CISAGDGSPQ

CDR3:                                                        SEQ ID NO: 32
SRWSNCAWDYYGMDP

IH37                                                         SEQ ID NO: 33
QVQLVESGGGLAQAGGSLRLSCQGSGRTFNNDVLAWFRQAPGKEREYVAMITSGG
NPFYADSVKGRFVISRDNDKNTVYLQMNSLKSEDTAIYYCAADENPPGWPSRWSSAY
DYWGQGTQVTVSS

CDR1:                                                        SEQ ID NO: 34
GRTFNNDVLA

CDR2:                                                        SEQ ID NO: 35
MITSGGNPF

CDR3:                                                        SEQ ID NO: 36
DENPPGWPSRWSSAYDY

IH39                                                         SEQ ID NO: 37
QVQLVESGGGLVQAGGSLRLSCVAYGVASVTTVMGWFRQSPGKEREFVAAIGPSGG
THYGDSAKGRFTISRDNAKNTVYLQMNSLKPEDTAVYDCAADLRGGGMWASSGRYE
YWGQGTQVTVSS

CDR1:                                                        SEQ ID NO: 38
GVASVTTVMG

CDR2:                                                        SEQ ID NO: 39
AIGPSGGTH

CDR3:                                                        SEQ ID NO: 40
DLRGGGMWASSGRYEY hC4bNb6                                                      SEQ ID NO: 41
QVQLVETGGGVVRAGGSLRLSCAASGRTLGRYSMAWFRQAPGKERQFVAAINWSG
GSTYYPDFAKDRFTISRDSAKNMVYLQMNSLKPEDTAVYYCAAGGMDIEITRANEYDY
WGQGTQVTVSS

CDR1:                                                        SEQ ID NO: 42
GRTLGRYSMA

CDR2:                                                        SEQ ID NO: 43
AINWSGGSTY
```

CDR3:
SEQ ID NO: 44
GGMDIEITRANEYDY hC4Nb8
SEQ ID NO: 45
QVQLVESGGGLVQTGDSLRLSCAASGRTFSRYAMGWFRQAPGKERELVAAINWSG
GSTYYADFAKGRFTISRDNAKNMLYLRMSSLKPEDTAVYYCAAGGPEVEITRANEYD
YWGQGTQVTVSS

CDR1:
SEQ ID NO: 46
GRTFSRYAMG

CDR2:
SEQ ID NO: 47
AINWSGGSTY

CDR3:
SEQ ID NO: 48
GGPEVEITRANEYDY

D121
SEQ ID NO: 49
QVQLVESGGGLVQAGGSLRLSCVVSGSTFSDYAMGWYRQAAGEQRELVAAIYSTGR
TNYIDSVKGRFTISRDNAKTTVYLQMNSLKPEDTAVYYCNLLGATTMINTKWGQGTQV
TVSS

CDR1:
SEQ ID NO: 50
SGSTFSDYAMG

CDR2:
SEQ ID NO: 51
AIYSTGRTN

CDR3:
SEQ ID NO: 52
LGATTMINTK

DI62
SEQ ID NO: 53
QVQLVESGGGLVQAGGSLRLSCAASGRTFSDYTMGWFRQAPGKEREFVAGLSTGG
SFTRYAASVEGRFTISRDNAKTTVYLQMNNLQPEDTAVYYCAADFTPYGTNWSRFRE
ARDHYWGQGTQVTVSS

CDR1:
SEQ ID NO: 54
SGRTFSDYTMG

CDR2:
SEQ ID NO: 55
GLSTGGSFTR

CDR3:
SEQ ID NO: 56
DFTPYGTNWSRFREARDHY

EWE-hC3Nb1
SEQ ID NO: 57
MEWEQVQLVETGGGLVQAGGSLRLSCAASGSIFSINAMGWFRQAPGKEREFVATIN
RSGGRTYYADSVKGRFTISRDNGKNMVYLQMHSLKPEDTAIYYCAAGTGWSPQTDN
EYNYWGQGTQVTVSS

CDR1:
SEQ ID NO: 58
SGSIFSINAMG

CDR2:
SEQ ID NO: 59
TINRSGGRTY

CDR3:
SEQ ID NO: 60
GTGWSPQTDNEYNY

IgG-Fc-hC3Nb1
SEQ ID NO: 61
APLEPKSSDKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYKCKVSNK
ALPAPIEKTISKAKGQPREPQVYTLPPSREEMTKNQVSLTCLVKGFYPSDIAVEWESN

-continued

```
GQPENNYKTTPPVLDSDGSFFLYSKLTVDKSRWQQGNVFSCSVMHEALHNHYTQKS
LSLSPGAQVQLVETGGGLVQAGGSLRLSCAASGSIFSINAMGWFRQAPGKEREFVAT
INRSGGRTYYADSVKGRFTISRDNGKNMVYLQMHSLKPEDTAIYYCAAGTGWSPQTD
NEYNYWGQGTQVTVSS
```

CDR1:
SEQ ID NO: 62

SGSIFSINAMG

CDR2:
SEQ ID NO: 63

TINRSGGRTY

CDR3:
SEQ ID NO: 64

GTGWSPQTDNEYNY

Polypeptide linker:
SEQ ID NO: 65

GGGGSGGGGS hC4Nb5
SEQ ID NO: 66

```
QVQLVETGGGLVQPGGSLRLSCAASGRTFNKNPMAWFRQPPGQERDLVAAISWSG
DSTNYANSVQGRFTISRNNAQRTVSLSMNNLKPEDTAVYYCAAVGRTDYSPNSLALT
AQNYDYWGQGTQVTVSS
```

CDR1:
SEQ ID NO: 67

GRTFNKNPMA

CDR2:
SEQ ID NO: 68

AISWSGDSTN

CDR3:
SEQ ID NO: 69

VGRTDYSPNSLALTAQNYD hC4Nb4
SEQ ID NO: 70

```
QVQLVETGGGLVEAGGSLRISCAASGRYAMGWFRQAPGNERDFVAAISRSGDSANY
ADTAWGRFTISRDNAQNTMTLQMNSLKPEDTAVYYCAAKAGLYSLNSLFLRSQEYTY
WGQGTQVTVSS
```

CDR1:
SEQ ID NO: 71

GRYAMG

CDR2:
SEQ ID NO: 72

AISRSGDSAN

CDR3:
SEQ ID NO: 73

KAGLYSLNSLFLRSQEYTY

Mouse C3 C345c domain UniProtKB - P01027 (CO3_MOUSE)
SEQ ID NO: 74

```
ENCFMQQSQEKINLNVRLDKACEPGVDYVYKTELTNIELLDDFDEYTMTIQQVIKSGS
DEVQAGGQQRKFISHIKCRNALKLQKGKKYLMWGLSSDLWGEKPNTSYIIGKDTWVEH
WPEAEECQDQKYQKQCEELGAFTESMVVYGCPN
```

Mouse C3, partial part of protein
SEQ ID NO: 75

EKINLNVRLDKAC
PEAEECQDQKYQKQCEELGAFTESMVVYGCPN pNSL270
SEQ ID NO: 76

```
QVQLVESGGGLVQAGGSLR
LSCVASASTLDIYTYAMAWF
RQAPGKRREFVAAISRNGYS
TYYADSVKGRFTISKLNAKN
TLYLQMNSLEPEDTAAYYCA
ADRTTEVVDREDDYGYWGQG
TQVTVSS
```

CDR1:
SEQ ID NO: 77

ASTLDIYTYAMA

CDR2:
SEQ ID NO: 78

AISRNGYSTY

CDR3:
SEQ ID NO: 79

DRTTEVVDREDDYGY

Human C4B alpha chain UniProtKB - P0C0L5 (CO4B_HUMAN) residues 680-1446
SEQ ID NO: 80
NVNFQKAINEKLGQYASPTAKRCCQDGVTRLPMMRSCEQRAARVQQPDCREPFLSC
CQFAESLRKKSRDKGQAGLQRALEILQEEDLIDEDDIPVRSFFPENWLWRVETVDRF
QILTLWLPDSLTTWEIHGLSLSKTKGLCVATPVQLRVFREFHLHLRLPMSVRRFEQLEL
RPVLYNYLDKNLTVSVHVSPVEGLCLAGGGGLAQQVLVPAGSARPVAFSVVPTAATA
VSLKVVARGSFEFPVGDAVSKVLQIEKEGAIHREELVYELNPLDHRGRTLEIPGNSDP
NMIPDGDFNSYVRVTASDPLDTLGSEGALSPGGVASLLRLPRGCGEQTMIYLAPTLAA
SRYLDKTEQWSTLPPETKDHAVDLIQKGYMRIQQFRKADGSYAAWLSRGSSTWLTAF
VLKVLSLAQEQVGGSPEKLQETSNWLLSQQQADGSFQDLSPVIHRSMQGGLVGNDE
TVALTAFVTIALHHGLAVFQDEGAEPLKQRVEASISKASSFLGEKASAGLLGAHAAAIT
AYALTLTKAPADLRGVAHNNLMAMAQETGDNLYWGSVTGSQSNAVSPTPAPRNPSD
PMPQAPALWIETTAYALLHLLLHEGKAEMADQAAAWLTRQGSFQGGFRSTQDTVIAL
DALSAYWIASHTTEERGLNVTLSSTGRNGFKSHALQLNNRQIRGLEEELQFSLGSKIN
VKVGGNSKGTLKVLRTYNVLDMKNTTCQDLQIEVTVKGHVEYTMEANEDYEDYEDE
LPAKDDPDAPLQPVTPLQLFEG Human C4b-A alpha chain UniProtKB - P0C0L4 (C04A_HUMAN) residues 757-
1446
SEQ ID NO: 81
ALEILQEEDLIDEDDIPVRSFFPENWLWRVETVDRFQILTLWLPDSLTTWEIHGLSLSKT
KGLCVATPVQLRVFREFHLHLRLPMSVRRFEQLELRPVLYNYLDKNLTVSVHVSPVEG
LCLAGGGGLAQQVLVPAGSARPVAFSVVPTAAAAVSLKVVARGSFEFPVGDAVSKVL
QIEKEGAIHREELVYELNPLDHRGRTLEIPGNSDPNMIPDGDFNSYVRVTASDPLDTLG
SEGALSPGGVASLLRLPRGCGEQTMIYLAPTLAASRYLDKTEQWSTLPPETKDHAVD
LIQKGYMRIQQFRKADGSYAAWLSRDSSTWLTAFVLKVLSLAQEQVGGSPEKLQETS
NWLLSQQQADGSFQDPCPVLDRSMQGGLVGNDETVALTAFVTIALHHGLAVFQDEG
AEPLKQRVEASISKANSFLGEKASAGLLGAHAAAITAYALTLTKAPVDLLGVAHNNLMA
MAQETGDNLYWGSVTGSQSNAVSPTPAPRNPSDPMPQAPALWIETTAYALLHLLLHE
GKAEMADQASAWLTRQGSFQGGFRSTQDTVIALDALSAYWIASHTTEERGLNVTLSS
TGRNGFKSHALQLNNRQIRGLEEELQFSLGSKINVKVGGNSKGTLKVLRTYNVLDMK
NTTCQDLQIEVTVKGHVEYTMEANEDYEDYEDELPAKDDPDAPLQPVTPLQLFEG Human C4b-B alpha chain UniProtKB - P0C0L5 (CO4B_HUMAN) residues 757-
1446
SEQ ID NO: 82
ALEILQEEDLIDEDDIPVRSFFPENWLWRVETVDRFQILTLWLPDSLTTWEIHGLSLSKT
KGLCVATPVQLRVFREFHLHLRLPMSVRRFEQLELRPVLYNYLDKNLTVSVHVSPVEG
LCLAGGGGLAQQVLVPAGSARPVAFSVVPTAATAVSLKVVARGSFEFPVGDAVSKVL
QIEKEGAIHREELVYELNPLDHRGRTLEIPGNSDPNMIPDGDFNSYVRVTASDPLDTLG
SEGALSPGGVASLLRLPRGCGEQTMIYLAPTLAASRYLDKTEQWSTLPPETKDHAVD
LIQKGYMRIQQFRKADGSYAAWLSRGSSTWLTAFVLKVLSLAQEQVGGSPEKLQETS
NWLLSQQQADGSFQDLSPVIHRSMQGGLVGNDETVALTAFVTIALHHGLAVFQDEGA
EPLKQRVEASISKASSFLGEKASAGLLGAHAAAITAYALTLTKAPADLRGVAHNNLMA
MAQETGDNLYWGSVTGSQSNAVSPTPAPRNPSDPMPQAPALWIETTAYALLHLLLHE
GKAEMADQAAAWLTRQGSFQGGFRSTQDTVIALDALSAYWIASHTTEERGLNVTLSS
TGRNGFKSHALQLNNRQIRGLEEELQFSLGSKINVKVGGNSKGTLKVLRTYNVLDMK
NTTCQDLQIEVTVKGHVEYTMEANEDYEDYEDELPAKDDPDAPLQPVTPLQLFEG Mouse Complement C4 beta chain - P01029 residues 20-673
SEQ ID NO: 83
KPRLLLFSPSVVNLGTPLSVGVQLLDAPPGQEVKGSVFLRNPKGGSCSPKKDFKLSS
GDDFVLLSLEVPLEDVRSCGLFDLRRAPHIQLVAQSPWLRNTAFKATETQGVNLLFSS
RRGHIFVQTDQPIYNPGQRVRYRVFALDQKMRPSTDFLTITVENSHGLRVLKKEIFTST
SIFQDAFTIPDISEPGTWKISARFSDGLESNRSTHFEVKKYVLPNFEVKITPWKPYILMV
PSNSDEIQLDIQARYIYGKPVQGVAYTRFALMDEQGKRTFLRGLETQAKLVEGRTHISI
SKDQFQAALDKINIGVRDLEGLRLYAATAVIESPGGEMEEAELTSWRFVSSAFSLDLS
RTKRHLVPGAHFLLQALVQEMSGSEASNVPVKVSATLVSGSDSQVLDIQQSTNGIGQ
VSISFPIPPTVTELRLLVSAGSLYPAIARLTVQAPPSRGTGFLSIEPLDPRSPSVGDTFIL
NLQPVGIPAPTFSHYYYMIISRGQIMAMGREPRKTVTSVSVLVDHQLAPSFYFVAYFY
HQGHPVANSLLINIQSRDCEGKLQLKVDGAKEYRNADMMKLRIQTDSKALVALGAVD
MALYAVGGRSHKPLDMSKVFEVINSYNVGCGPGGGDDALQVFQDAGLAFSDGDRLT
QTREDLSCPKEKKS -continued Mouse Complement C4 alpha chain - P01029 residues 678-1443
SEQ ID NO: 84
NVNFQKAVSEKLGQYSSPDAKRCCQDGMTKLPMKRTCEQRAARVPQQACREPFLS
CCKFAEDLRRNQTRSQAHLARNNHNMLQEEDLIDEDDILVRTSFPENWLWRVEPVDS
SKLLTVWLPDSMTTWEIHGVSLSKSKGLCVAKPTRVRVFRKFHLHLRLPISIRRFEQFE
LRPVLYNYLNDDVAVSVHVTPVEGLCLAGGGMMAQQVTVPAGSARPVAFSVVPTAA
ANVPLKVVARGVFDLGDAVSKILQIEKEGAIHREELVYNLDPLNNLGRTLEIPGSSDPNI
VPDGDFSSLVRVTASEPLETMGSEGALSPGGVASLLRLPQGCAEQTMIYLAPTLTASN
YLDRTEQWSKLSPETKDHAVDLIQKGYMRIQQFRKNDGSFGAWLHRDSSTWLTAFVL
KILSLAQEQVGNSPEKLQETASWLLAQQLGDGSFHDCPVIHRAMQGGLVGSDETVA
LTAFVVIALHHGLDVFQDDDAKQLKNRVEASITKANSFLGQKASAGLLGAHAAAITAYA
LTLTKASEDLRNVAHNSLMAMAEETGEHLYWGLVLGSQDKVVLRPTAPRSPTEPVPQ
APALWIETTAYALLHLLREGKGKMADKAASWLTHQGSFHGAFRSTQDTVVTLDALS
AYWIASHTTEEKALNVTLSSMGRNGLKTHGLHLNNHQVKGLEEELKFSLGSTISVKVE
GNSKGTLKILRTYNVLDMKNTTCQDLQIEVKVTGAVEYAWDANEDYEDYYDMPAADD
PSVPLQPVTPLQLFEGRRS SEQ ID NO: 85
EAPKVVEEQESRVQYTVCIWRNGKLGLSGMAIADITLLSGFHALRADLEKLTSLSDRY
VSHFETDGPHVLLYFDSVPTTRECVGFGASQEVVGLVQPSSAVLYDYYSPDHKCSV
FYAAPTKSQLLATLCSGDVCQCAEGKCPRLLRSLERRVEDKDGYRMRFACYYPRVE
YGFTVKVLREDGRAAFRLFESKITQVLHFRKDTMASIGQTRNFLSRASCRLRLEPNKE
YLIMGMDGETSDNKGDPQYLLDSNTWIEEMPSEQMCKSTRHRAACFQLKDFLMEFS
SRGCQV

---

The invention claimed is:

1. A polypeptide construct that comprises:
   (a) a $V_HH$ domain that binds to human C1q complement factor; and
   (b) a target binding moiety that binds to a target selected from the group consisting of:
      a cancer-specific marker; a pathogenic marker; a tissue-specific marker; and an organ-specific marker,
   wherein the target-binding moiety comprises a heavy chain constant region ($C_H$), a heavy chain variable region ($V_H$), a light chain constant region ($C_L$), a light chain variable region ($V_L$), a camelid $V_HH$ domain, or a cartilaginous fish $V_{NAR}$ domain, and wherein the polypeptide construct activates a classical complement system when the polypeptide construct is bound to a cell surface.

2. The polypeptide construct of claim 1, wherein the target binding domain binds to the cancer-specific marker.

3. The polypeptide construct of claim 1, wherein the target is EGFR, CD38, CD19, CD20, cMET, CD33, CD22, CD52, VEGF, PSMA, EpCam, Her, GD3, Erb2, or CD30.

4. The polypeptide construct of claim 3, wherein the target is EGFR.

5. The polypeptide construct of claim 3, wherein the target is CD38.

6. The polypeptide construct of claim 1, wherein the target-binding moiety binds to the pathogenic marker.

7. The polypeptide construct of claim 6, wherein the pathogenic marker is a bacterial marker, a viral marker, or a fungal marker.

8. The polypeptide construct of claim 1, wherein the target-binding moiety binds to the tissue-specific marker or the organ-specific marker.

9. The polypeptide construct of claim 1, wherein the $V_HH$ domain binds to the human C1q complement factor with a $K_D$ of about $10^{-4}$ M or less.

10. The polypeptide construct of claim 1, wherein the polypeptide construct further comprises a linker.

11. The polypeptide construct of claim 10, wherein the linker is between the $V_HH$ domain and the target-binding moiety.

12. The polypeptide construct of claim 1, wherein the $V_HH$ domain and the target-binding moiety are coupled to an Fc-fragment.

13. The polypeptide construct of claim 1, wherein the $V_HH$ domain or the target-binding moiety are covalently linked to a small chemical molecule.

14. The polypeptide construct of claim 1, wherein the target-binding variable region is a $V_HH$ domain.

15. A pharmaceutical composition that comprises:
(a) a polypeptide construct that comprises:
(i) a $V_HH$ domain that binds to human C1q complement factor; and
(ii) a $V_HH$ domain that binds to CD38,
wherein the polypeptide construct activates a classical complement system
when the polypeptide construct is bound to a cell surface; and
(b) a pharmaceutically acceptable carrier or diluent.

16. The pharmaceutical composition of claim 15, in the form of an injectable solution.

17. A method of treating a disease or condition associated with complement activity in a subject in need thereof, the method comprising administering to the subject the pharmaceutical composition of claim 15.

18. The pharmaceutical composition of claim 16, wherein the pharmaceutical composition is formulated for subcutaneous injection.

19. The pharmaceutical composition of claim 16, wherein the pharmaceutical composition is formulated for parenteral injection.

* * * * *